(12) United States Patent
Feder et al.

(10) Patent No.: US 7,259,002 B2
(45) Date of Patent: Aug. 21, 2007

(54) POLYNUCLEOTIDE ENCODING A NOVEL ACYL COENZYME A, MONOACYLGLYCEROL ACYLTRANSFERASE-3 (MGAT3), AND USES THEREOF

(75) Inventors: John N. Feder, Belle Mead, NJ (US); Thomas C. Nelson, Lawrenceville, NJ (US); Jian Chen, Princeton, NJ (US); Rupalie Meegalla, Boothwyn, PA (US); Michael Ramaker, Greenville, DE (US); Dong Cheng, Furlong, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 450 days.

(21) Appl. No.: 10/761,905

(22) Filed: Jan. 21, 2004

(65) Prior Publication Data

US 2004/0223959 A1  Nov. 11, 2004

Related U.S. Application Data

(60) Provisional application No. 60/441,567, filed on Jan. 21, 2003.

(51) Int. Cl.
*C12N 9/10* (2006.01)
*C12N 1/20* (2006.01)
*C12N 15/00* (2006.01)
*C07H 21/04* (2006.01)

(52) U.S. Cl. .............. 435/193; 435/252.3; 435/320.1; 536/23.2

(58) Field of Classification Search ................ 435/193, 435/252.3, 320.1; 536/23.2
See application file for complete search history.

(56) References Cited

U.S. PATENT DOCUMENTS

| | | | |
|---|---|---|---|
| 4,179,337 | A | 12/1979 | Davis et al. |
| 4,376,110 | A | 3/1983 | David et al. |
| 4,444,887 | A | 4/1984 | Hoffmann |
| 4,474,893 | A | 10/1984 | Reading |
| 4,631,211 | A | 12/1986 | Houghten |
| 4,676,980 | A | 6/1987 | Segal et al. |
| 4,714,681 | A | 12/1987 | Reading |
| 4,716,111 | A | 12/1987 | Osband et al. |
| 4,741,900 | A | 5/1988 | Alvarez et al. |
| 4,816,397 | A | 3/1989 | Boss et al. |
| 4,816,567 | A | 3/1989 | Cabilly et al. |
| 4,897,355 | A | 1/1990 | Eppstein et al. |
| 4,925,648 | A | 5/1990 | Hansen et al. |
| 4,946,778 | A | 8/1990 | Ladner et al. |
| 4,946,787 | A | 8/1990 | Eppstein et al. |
| 4,980,286 | A | 12/1990 | Morgan et al. |
| 5,010,175 | A | 4/1991 | Rutter et al. |
| 5,049,386 | A | 9/1991 | Eppstein et al. |
| 5,073,627 | A | 12/1991 | Curtis et al. |
| 5,112,946 | A | 5/1992 | Maione |
| 5,122,464 | A | 6/1992 | Wilson et al. |
| 5,139,941 | A | 8/1992 | Muzyczka et al. |
| 5,173,414 | A | 12/1992 | Lebkowski et al. |
| 5,205,290 | A | 4/1993 | Unger |
| 5,223,409 | A | 6/1993 | Ladner et al. |
| 5,225,539 | A | 7/1993 | Winter |
| 5,258,498 | A | 11/1993 | Huston et al. |
| 5,288,514 | A | 2/1994 | Ellman |
| 5,314,995 | A | 5/1994 | Fell, Jr. et al. |
| 5,336,603 | A | 8/1994 | Capon et al. |
| 5,349,053 | A | 9/1994 | Landolfi |
| 5,354,678 | A | 10/1994 | Lebkowski et al. |
| 5,359,046 | A | 10/1994 | Capon et al. |
| 5,403,484 | A | 4/1995 | Ladner et al. |
| 5,413,923 | A | 5/1995 | Kucherlapati et al. |
| 5,427,908 | A | 6/1995 | Dower et al. |
| 5,436,146 | A | 7/1995 | Shenk et al. |
| 5,441,050 | A | 8/1995 | Thurston et al. |
| 5,447,851 | A | 9/1995 | Beutler et al. |
| 5,459,127 | A | 10/1995 | Felgner et al. |
| 5,474,935 | A | 12/1995 | Chatterjee et al. |
| 5,474,981 | A | 12/1995 | Leder et al. |
| 5,478,745 | A | 12/1995 | Samulski et al. |
| 5,478,925 | A | 12/1995 | Wallach et al. |

(Continued)

FOREIGN PATENT DOCUMENTS

CA 2045869 12/1991

(Continued)

OTHER PUBLICATIONS

Sacher A et al: "Presteady-state and steady-state kinetics and turnover rate of the mouse gamma-aminobutyric acid transporter (mGAT3)." Journal of Membrane Biology, vol. 190, No. 1, Nov. 1, 2002, pp. 57-73.

(Continued)

*Primary Examiner*—Tekchand Saidha
(74) *Attorney, Agent, or Firm*—Brian C. Carey

(57) ABSTRACT

The present invention provides novel polynucleotides encoding MGAT3 polypeptides, fragments and homologues thereof. Also provided are vectors, host cells, antibodies, and recombinant and synthetic methods for producing MGAT3 polypeptides, fragments, and homologues thereof. The invention further relates to diagnostic and therapeutic methods for applying these novel MGAT3 polypeptides to the diagnosis, treatment, and/or prevention of various diseases and/or disorders related to these polypeptides, such as obesity. The invention further relates to screening methods for identifying agonists and antagonists of the polynucleotides and polypeptides of the present invention.

6 Claims, 11 Drawing Sheets

U.S. PATENT DOCUMENTS

| | | | |
|---|---|---|---|
| 5,506,337 A | 4/1996 | Summerton et al. | |
| 5,516,637 A | 5/1996 | Huang et al. | |
| 5,519,134 A | 5/1996 | Acevedo et al. | |
| 5,525,735 A | 6/1996 | Gallop et al. | |
| 5,530,101 A | 6/1996 | Queen et al. | |
| 5,539,083 A | 7/1996 | Cook et al. | |
| 5,545,806 A | 8/1996 | Lonberg et al. | |
| 5,545,807 A | 8/1996 | Surani et al. | |
| 5,549,974 A | 8/1996 | Holmes | |
| 5,565,332 A | 10/1996 | Hoogenboom et al. | |
| 5,569,588 A | 10/1996 | Ashby et al. | |
| 5,569,825 A | 10/1996 | Lonberg et al. | |
| 5,571,698 A | 11/1996 | Ladner et al. | |
| 5,573,920 A | 11/1996 | Randle | |
| 5,580,717 A | 12/1996 | Dower et al. | |
| 5,580,859 A | 12/1996 | Felgner et al. | |
| 5,585,089 A | 12/1996 | Queen et al. | |
| 5,589,377 A | 12/1996 | Lebkowski et al. | |
| 5,589,466 A | 12/1996 | Felgner et al. | |
| 5,593,853 A | 1/1997 | Chen et al. | |
| 5,593,972 A | 1/1997 | Weiner et al. | |
| 5,601,819 A | 2/1997 | Wong et al. | |
| 5,605,793 A | 2/1997 | Stemmer | |
| 5,622,929 A | 4/1997 | Willner et al. | |
| 5,625,126 A | 4/1997 | Lonberg et al. | |
| 5,633,425 A | 5/1997 | Lonberg et al. | |
| 5,641,670 A | 6/1997 | Treco et al. | |
| 5,652,224 A | 7/1997 | Wilson et al. | |
| 5,658,727 A | 8/1997 | Barbas et al. | |
| 5,661,016 A | 8/1997 | Lonberg et al. | |
| 5,661,106 A | 8/1997 | Baumann et al. | |
| 5,676,954 A | 10/1997 | Brigham | |
| 5,693,622 A | 12/1997 | Wolff et al. | |
| 5,698,426 A | 12/1997 | Huse | |
| 5,703,055 A | 12/1997 | Felgner et al. | |
| 5,733,743 A | 3/1998 | Johnson et al. | |
| 5,733,761 A | 3/1998 | Treco et al. | |
| 5,750,753 A | 5/1998 | Kimae et al. | |
| 5,780,225 A | 7/1998 | Wigler et al. | |
| 5,807,715 A | 9/1998 | Morrison et al. | |
| 5,811,097 A | 9/1998 | Allison et al. | |
| 5,811,238 A | 9/1998 | Stemmer et al. | |
| 5,814,318 A | 9/1998 | Lonberg et al. | |
| 5,821,047 A | 10/1998 | Garrard et al. | |
| 5,830,721 A | 11/1998 | Stemmer et al. | |
| 5,834,252 A | 11/1998 | Stemmer et al. | |
| 5,837,458 A | 11/1998 | Minshull et al. | |
| 5,837,832 A | 11/1998 | Chee et al. | |
| 5,856,104 A | 1/1999 | Chee et al. | |
| 5,856,174 A | 1/1999 | Lipshutz et al. | |
| 5,858,659 A | 1/1999 | Sapolsky et al. | |
| 5,874,219 A | 2/1999 | Rava et al. | |
| 5,885,793 A | 3/1999 | Griffiths et al. | |
| 5,914,123 A | 6/1999 | Arntzen et al. | |
| 5,916,771 A | 6/1999 | Hori et al. | |
| 5,939,598 A | 8/1999 | Kucherlapati et al. | |
| 5,969,108 A | 10/1999 | McCafferty et al. | |
| 5,985,660 A | 11/1999 | Galy | |
| 6,020,141 A | 2/2000 | Pantoliano et al. | |
| 6,028,066 A | 2/2000 | Unger | |
| 6,034,298 A | 3/2000 | Lam et al. | |
| 6,036,920 A | 3/2000 | Pantoliano et al. | |
| 6,822,141 B2 * | 11/2004 | Lardizabal et al. | 800/281 |
| 6,835,556 B2 * | 12/2004 | Attersand | 435/69.1 |
| 2003/0170691 A1 * | 9/2003 | Gimeno et al. | 435/6 |

FOREIGN PATENT DOCUMENTS

| | | |
|---|---|---|
| EP | 0 307 434 | 9/1983 |
| EP | 0 173 494 | 3/1986 |
| EP | 0 367 166 | 5/1990 |
| EP | 0 394 827 | 10/1990 |
| EP | 0 519 586 | 12/1992 |
| EP | 0 171 496 | 5/1993 |
| EP | 0 396 387 | 12/1993 |
| EP | 0 592 106 | 4/1994 |
| EP | 0 239 400 | 8/1994 |
| EP | 0 401 384 | 3/1996 |
| EP | 0 439 095 | 5/1998 |
| EP | 0 464 533 | 7/1998 |
| WO | WO84/03564 | 9/1984 |
| WO | WO86/01533 | 3/1986 |
| WO | WO86/05807 | 10/1986 |
| WO | WO87/01130 | 2/1987 |
| WO | WO87/02671 | 5/1987 |
| WO | WO88/09810 | 12/1988 |
| WO | WO89/01036 | 2/1989 |
| WO | WO89/10134 | 11/1989 |
| WO | WO89/12624 | 12/1989 |
| WO | WO90/02809 | 3/1990 |
| WO | WO90/11092 | 10/1990 |
| WO | WO90/11364 | 10/1990 |
| WO | WO91/00360 | 1/1991 |
| WO | WO91/06570 | 5/1991 |
| WO | WO91/09967 | 7/1991 |
| WO | WO91/10737 | 7/1991 |
| WO | WO91/10741 | 7/1991 |
| WO | WO91/14438 | 10/1991 |
| WO | WO91/15580 | 10/1991 |
| WO | WO91/19735 | 12/1991 |
| WO | WO92/00091 | 1/1992 |
| WO | WO92/01047 | 1/1992 |
| WO | WO92/05793 | 4/1992 |
| WO | WO92/06180 | 4/1992 |
| WO | WO92/08495 | 5/1992 |
| WO | WO92/08802 | 5/1992 |
| WO | WO92/18619 | 10/1992 |
| WO | WO92/20316 | 11/1992 |
| WO | WO92/20373 | 11/1992 |
| WO | WO92/22324 | 12/1992 |
| WO | WO92/22635 | 12/1992 |
| WO | WO93/08829 | 5/1993 |
| WO | WO93/11236 | 6/1993 |
| WO | WO93/14188 | 7/1993 |
| WO | WO93/17715 | 9/1993 |
| WO | WO93/20221 | 10/1993 |
| WO | WO93/20242 | 10/1993 |
| WO | WO93/21232 | 10/1993 |
| WO | WO94/08598 | 4/1994 |
| WO | WO94/10308 | 5/1994 |
| WO | WO94/12649 | 6/1994 |
| WO | WO94/12650 | 6/1994 |
| WO | WO95/15982 | 6/1995 |
| WO | WO95/20401 | 8/1995 |
| WO | WO96/04388 | 2/1996 |
| WO | WO96/22024 | 7/1996 |
| WO | WO96/29411 | 9/1996 |
| WO | WO96/33735 | 10/1996 |
| WO | WO96/34096 | 10/1996 |
| WO | WO96/40281 | 12/1996 |
| WO | WO97/00271 | 1/1997 |
| WO | WO97/33899 | 9/1997 |
| WO | WO97/34911 | 9/1997 |
| WO | WO98/16654 | 4/1998 |
| WO | WO98/24893 | 6/1998 |
| WO | WO98/46645 | 10/1998 |
| WO | WO98/49305 | 11/1998 |
| WO | WO98/50433 | 11/1998 |
| WO | WO99/04813 | 2/1999 |
| WO | WO99/07865 | 2/1999 |
| WO | WO99/23105 | 5/1999 |
| WO | WO99/32619 | 7/1999 |
| WO | WO 00/05391 | 2/2000 |
| WO | WO 01/29058 | 4/2001 |

| | | |
|---|---|---|
| WO | WO 01/57190 | 8/2001 |
| WO | WO 03/039341 | 5/2003 |
| WO | WO 03/053363 | 7/2003 |

OTHER PUBLICATIONS

Cheng et al., Identification of Acyl Coenzyme A: Monoacylglycerol Acyltransferase 3, an Intestinal Specific Enzyme Implicated in Dietary Fat Absorption. J. Biol. Chem., Apr. 18, 2003, vol. 278, No. 16 pp. 13611-13614. See GenBank Accession Nos. AY229854 and Q86VF5.

Database on GenBank, Sulston et al., Towards a complete human genome sequencing. May 1, 2000, Accession No. Q9UDW7.

Data base on GenBank, Voelker et al., Cloning of DGAT2, a Second Mammalian Diacylglycerol Acyltransferase, and Related Family Members, J. Biol. Chem. 276; 38870-38876, Oct. 1, 2001. Accession No. Q96PD7.

Cao, et al., Cloning and Functional Characterization of a Mouse Intestinal Acyl-CoA; Monoacylglycerol Acyltransferase, MGAT2, J. Biol. Chem., Apr. 18, 2003, vol. 278, No. 16, pp. 13860-13866.

Yen et al., Identification of a gene encoding MGAT1, a monoacylglyceral acyltransferase, PNAS, Jun. 25, 2002, vol. 99, No. 13, pp. 8512-8517.

Database GenBank, Tang et al. [(WO200157190) Aug. 9, 2001], Accession No. AAK53395.

Database GenBank, Gimeno et al. [WO2003053363-A2], Jul. 3, 2003, Accession No. AAD56887 and AAE37787.

Database GenBank, Logan et al., [WO2003039341-A1], May 15, 2003, Accession No. AAE37357.

NCBI Entrez Accession No. gi|AF384161, Cases, S. et al., Jan. 11, 2002.

NCBI Entrez Accession No. gi|AF384163, Cases, S. et al., Oct. 16, 2001.

Aldhous, M.C. et al., "Modification of enteral diets in inflammatory bowel disease", Proceedings of the Nutrition Society, vol. 60, pp. 457-461 (2001).

Ames, R.S. et al., "Conversion of murine Fabs isolated from a combinatorial phage display library to full length immunoglobulins", Journal of Immunological Methods, vol. 184, pp. 177-186 (1995).

Arenkov, P. et al., "Protein Microchips: Use for Immunoassay and Enzymatic Reactions", Analytical Biochemistry, vol. 278, pp. 123-131 (2000).

Arnon, R. et al., "Monoclonal Antibodies for Immunotargeting of Drugs in Cancer Therapy", Monoclonal Antibodies and Cancer Therapy, Proceedings of the Roche-UCLA Symposium, Park City, UT, Jan. 26-Feb. 2, 1985, Alan R. Liss, Inc., publ., Reisfeld, R.A. et al., eds., pp. 243-256 (1985).

Ashkenazi, A. et al., "Protection against endotoxic shock by a tumor necrosis factor receptor immunoadhesin", Proc. Natl. Acad. Sci. USA, vol. 88, pp. 10535-10539 (1991).

Ausubel, F.M. et al., eds., Current Protocols in Molecular Biology, vols. 1-4, John Wiley & Sons, Inc., publ., pp. 1-11 (table of contents) (2001).

Ausubel, F.M. et al., eds., Chapter 2: "Preparation and Analysis of DNA", Current Protocols in Molecular Biology, vol. 1, John Wiley & Sons, Inc., publ., pp. 1-3 (table of contents), 2.1.1-2.12.7 (1999).

Ausubel, F.M. et al., eds., Unit 6.3: "Using DNA Fragments as Probes", Current Protocols in Molecular Biology, vol. 1, John Wiley & Sons, Inc., publ., pp. 6.3.1-6.3.6 (1993).

Ausubel, F.M. et al., eds., Unit 10.8: "Immunoblotting and Immunodetection", Current Protocols in Molecular Biology, vol. 2, John Wiley & Sons, Inc., publ., pp. 10.8.1-10.8.21 (1997).

Ausubel, F.M. et al., eds., Unit 10.16: "Immunoprecipitation", Current Protocols in Molecular Biology, vol. 2, John Wiley & Sons, Inc., publ., pp. 10.16.1-10.16-29 (1999).

Ausubel, F.M. et al., eds., Unit 11.2: "Enzyme-Linked Immunosorbent Assays (ELISA)", Current Protocols in Molecular Biology, vol. 2, John Wiley & Sons, Inc., publ., pp. 11.2.1-11.2.22 (1991).

Bartlett, R.J. et al., "In vivo targeted repair of a point mutation in the canine dystrophin gene by a chimeric RNA/DNA oligonucleotide", Nature Biotechnology, vol. 18, pp. 615-622 (2000).

Bartůněk, P. et al., "Avian Stem Cell Factor (SCF): Production and Characterization of the Recombinant His-Tagged SCF of Chicken and Its Neutralizing Antibody", Cytokine, vol. 8, No. 1, pp. 14-20 (1996).

Baum, R., "Solid-phase synthesis of benzodiazepines", C&EN, pp. 33-34 (1993).

Bause, E., "Structural requirements of N-glycosylation of proteins", Biochem. J., vol. 209, pp. 331-336 (1983).

Beal, P.A. et al., "Second Structural Motif for Recognition of DNA by Oligonucleotide-Directed Triple-Helix Formation", Science, vol. 251, pp. 1360-1363 (1991).

Bell, R.M. et al., "Enzymes of Glycerolipid Synthesis in Eukaryotes", Ann. Rev. Biochem., vol. 49, pp. 459-487 (1980).

Belldegrun, A. et al., "Human Renal Carcinoma Line Transfected With Interleukin-2 and/or Interferon α Gene(s): Implications for Live Cancer Vaccines", Journal of the National Cancer Institute, vol. 85, No. 3, pp. 207-216 (1993).

Bennett, D. et al., "Kinetic Characterization of the Interaction of Biotinylated Human Interleukin 5 with an Fc Chimera of its Receptor α Subunit and Development of an ELISA Screening Assay using Real-Time Interaction Biosensor Analysis", Journal of Molecular Recognition, vol. 8, pp. 52-58 (1995).

Benoist, C. et al., "In vivo sequence requirements of the SV40 early promoter region", Nature, vol. 290, pp. 304-310 (1981).

Better, M. et al., "*Escherichia coli* Secretion of an Active Chimeric Antibody Fragment", Science, vol. 240, pp. 1041-1043 (1988).

Bird, R.E. et al., "Single-Chain Antigen-Binding Proteins", Science, vol. 242, pp. 423-426 (1988).

Bitter, G.A. et al., "Expression and Secretion Vectors for Yeast", Methods in Enzymology, vol. 153, pp. 516-544 (1987).

Boerner, P. et al., "Production of Antigen-Specific Human Monoclonal Antibodies from In Vitro-Primed Human Splenocytes", The Journal of Immunology, vol. 147, No. 1, pp. 86-95 (1991).

Boesen, J.J.B. et al., "Circumvention of chemotherapy-induced myelosuppression by transfer of the *mdr1* gene", Biotherapy, vol. 6, pp. 291-302 (1994).

Boulianne, G.L. et al., "Production of functional chimaeric mouse/human antibody", Nature, vol. 312, pp. 643-646 (1984).

Bout, A. et al., "Lung Gene Therapy: In Vivo Adenovirus-Mediated Gene Transfer to Rhesus Monkey Airway Epithelium", Human Gene Therapy, vol. 5, pp. 3-10 (1994).

Bowie, J.U. et al., "Deciphering the Message in Protein Sequences: Tolerance to Amino Acid Substitutions", Science, vol. 247, pp. 1306-1310 (1990).

Bradbury, A.F. et al., "Biosynthesis of the C-Terminal Amide in Peptide Hormones", Bioscience Reports, vol. 7, No. 12, pp. 907-916 (1987).

Brinkmann, U. et al., "Phage display of disulfide-stabilized Fv fragments", Journal of Immunological Methods, vol. 182, pp. 41-50 (1995).

Brinster, R.L. et al., "Regulation of metallothionein-thymidine kinase fusion plasmids injected into mouse eggs", Nature, vol. 296, pp. 39-42 (1982).

Brodeur, B.R. et al., Chapter 4: "Mouse-Human Myeloma Partners for the Production of Heterohybridomas", Monoclonal Antibody Production Techniques and Applications, Marcel Dekker, Inc., publ., Schnook, L.B., ed., pp. 51-63 (1987).

Buchwald, H. et al., "Long-term, continuous intravenous heparin administration by an implantable infusion pump in ambulatory patients with recurrent venous thrombosis", Surgery, vol. 88, No. 4, pp. 507-516 (1980).

Burchiel, S.W. et al., Chapter 13: "Immunopharmacokinetics of Radiolabeled Antibodies and Their Fragments", Tumor Imaging: The Radiochemical Detection of Cancer, Masson Publishing Inc., publ., Burchiel, S.W. et al., eds., pp. 125-139 (1982).

Burton, D.R. et al., "Human Antibodies from Combinatorial Libraries", Advances in Immunology, vol. 57, pp. 191-280 (1994).

Campbell, D.A. et al., "Phosphonate Ester Synthesis Using a Modified Mitsunobu Condensation", J. Org. Chem., vol. 59, No. 3, pp. 658-660 (1994).

Carlson, N.G. et al., "Identification of Amino Acids in the Glutamate Receptor, GluR3, Important for Antibody-binding and Receptor-specific Activation", The Journal of Biological Chemistry, vol. 272, No. 17, pp. 11295-11301 (1997).

Cases, S. et al., "Cloning of DGAT2, a Second Mammalian Diacylglycerol Acyltransferase, and Related Family Members", The Journal of Biological Chemistry, vol. 276, No. 42, pp. 38870-38876 (2001).

Chen, C. et al., "'Analogous' Organic Synthesis of Small-Compound Libraries: Validation of Combinatorial Chemistry in Small-Molecule Synthesis", J. Am. Chem. Soc., vol. 116, No. 6, pp. 2661-2662 (1994).

Chen, Z. et al., "Effects of Interleukin-1α, Interleukin-1 Receptor Antagonist, and Neutralizing Antibody on Proinflammatory Cytokine Expression by Human Squamous Cell Carcinoma Lines", Cancer Research, vol. 58, pp. 3668-3676 (1998).

Cheng, Z. et al., "Capacitive detection of glucose using molecularly imprinted polymers", Biosensors & Bioelectronics, vol. 16, pp. 179-185 (2001).

Cho, C.Y. et al., "An Unnatural Biopolymer", Science, vol. 261, pp. 1303-1305 (1993).

Chothia, C. et al., "Structural Determinants in the Sequences of Immunoglobulin Variable Domain", J. Mol. Biol., vol. 278, pp. 457-479 (1998).

Chow, M. et al., "Synthetic peptides from four separate regions of the poliovirus type 1 capsid protein VP1 induce neutralizing antibodies", Proc. Natl. Acad. Sci. USA, vol. 82, pp. 910-914 (1985).

Cleland, J.L. et al., "The Development of Stable Protein Formulations: A Close Look at Protein Aggregation, Deamidation, and Oxidation", Critical Reviews in Therapeutic Drug Carrier Systems, vol. 10, No. 4, pp. 307-377 (1993).

Cline, M.J. et al., "Perspectives for Gene Therapy: Inserting New Genetic Information Into Mammalian Cells by Physical Techniques and Viral Vectors", Pharmac. Ther., vol. 29, pp. 69-92 (1985).

Clowes, M.M. et al., "Long-Term Biological Response of Injured Rat Carotid Artery Seeded with Smooth Muscle Cells Expressing Retrovirally Introduced Human Genes", J. Clin. Invest., vol. 93, pp. 644-651 (1994).

Cockett, M.I. et al., "High Level Expression of Tissue Inhibitor of Metalloproteinases in Chinese Hamster Ovary Cells Using Glutamine Synthetase Gene Amplification", Bio/Technology, vol. 8, pp. 662-667 (1990).

Cohen, J.S., ed., Oligodeoxynucleotides: Antisense Inhibitors of Gene Expression, CRC Press, Inc., publ., pp. v-viii (table of contents) (1989).

Colbère-Garapin, F. et al., "A New Dominant Hybrid Selective Marker for Higher Eukaryotic Cells", J. Mol. Biol., vol. 150, pp. 1-14 (1981).

Cole, S.P.C. et al., "The EBV-Hybridoma Technique and Its Application to Human Lung Cancer", Monoclonal Antibodies and Cancer Therapy, Proceedings of the Roche-UCLA Symposium, Park City, UT, Jan. 26-Feb. 2, 1985, Alan R. Liss, Inc., publ., Reisfeld, R.A. et al., eds., pp. 77-96 (1985).

Coleman, R.A., "Diacylglycerol Acyltransferase and Monoacylglycerol Acyltransferase from Liver and Intestine", Methods in Enzymology, vol. 209, pp. 98-104 (1992).

Coleman, R.A. et al., "Selective Changes in Microsomal Enzymes of Triacylglycerol Phosphatidylcholine, and Phosphatidylethanolamine Biosynthesis during Differentiation of 3T3-L1 Preadipocytes", The Journal of Biological Chemistry, vol. 253, No. 20, pp. 7256-7261 (1978).

Cooney, M. et al., "Site-Specific Oligonucleotide Binding Represses Transcription of the Human c-myc Gene in Vitro", Science, vol. 241, pp. 456-459 (1988).

Cote, R.J. et al., "Generation of human monoclonal antibodies reactive with cellular antigens", Proc. Natl. Acad. Sci. USA, vol. 80, pp. 2026-2030 (1983).

Cotten, M. et al., "Receptor-Mediated Transport of DNA into Eukaryotic Cells", Methods in Enzymology, vol. 217, pp. 618-644 (1993).

Creighton, T.E., Proteins: Structures and Molecular Properties, Second Edition, W.H. Freeman and Company, publ., pp. v-x (table of contents) (1993).

Crouse, G.F. et al., "Expression and Amplification of Engineered Mouse Dihydrofolate Reductase Minigenes", Molecular and Cellular Biology, vol. 3, No. 2, pp. 257-266 (1983).

Cunningham, B.C. et al., "High-Resolution Epitope Mapping of hGH-Receptor Interactions by Alanine-Scanning Mutagenesis", Science, vol. 244, pp. 1081-1085 (1989).

Cutrona, G. et al., "Effects in live cells of a c-myc anti-gene PNA linked to a nuclear localization signal", Nature Biotechnology, vol. 18, pp. 300-303 (2000).

David, G.S. et al., "Protein Iodination with Solid State Lactoperoxidase", Biochemistry, vol. 13, No. 5, pp. 1014-1021 (1974).

Davis, L.G. et al., Basic Methods in Molecular Biology, Elsevier Science Publishing Co., Inc., publ., pp. v-viii (table of contents) (1986).

Deamer, D. et al., "Large Volume Liposomes by an Ether Vaporization Method", Biochimica et Biophysica Acta, vol. 443, pp. 629-634 (1976).

Debs, R.J. et al., "Regulation of Gene Expression in Vivo by Liposome-mediated Delivery of a Purified Transcription Factor", The Journal of Biological Chemistry, vol. 265, No. 18, pp. 10189-10192 (1990).

Deng, B. et al., "An Agonist Murine Monoclonal Antibody to the Human c-Mpl Receptor Stimulates Megakaryocytopoiesis", Blood, vol. 92, No. 6, pp. 1981-1988 (1998).

DeWitt, S.H. et al., "'Diversomers': An approach to nonpeptide, nonoligomeric chemical diversity", Proc. Natl. Acad. Sci. USA, vol. 90, pp. 6909-6913 (1993).

Dickert, F.L. et al., "Synthetic receptors as sensor coatings for molecules and living cells", The Analyst, vol. 126, pp. 766-771 (2001).

Döbeli, H. et al., "Role of the carboxy-terminal sequence on the biological activity of human immune interferon (IFN-γ)", Journal of Biotechnology, vol. 7, pp. 199-216 (1988).

Dracopoli, N.C. et al., eds., Chapter 12: "Vectors for Gene Therapy", Current Protocols in Human Genetics, vol. 3, John Wiley & Sons, Inc., publ., pp. 12.0.1-12.12.15 (1999).

Dracopoli, N.C. et al., eds., Chapter 13: "Delivery Systems for Gene Therapy", Current Protocols in Human Genetics, vol. 3, John Wiley & Sons, Inc., publ., pp. 13.0.1-13.10.7 (2000).

During, M.J. et al., "Controlled Release of Dopamine from a Polymeric Brain Implant: In Vivo Characterization", Annals of Neurology, vol. 25, No. 4, pp. 351-356 (1989).

Egholm, M. et al., "PNA hybridizes to complementary oligonucleotides obeying the Watson-Crick hydrogen-bonding rules", Nature, vol. 365, pp. 566-568 (1993).

Ellis, S.B. et al., "Isolation of Alcohol Oxidase and Two Other Methanol Regulatable Genes from the Yeast *Pichia pastoris*", Molecular and Cellular Biology, vol. 5, No. 5, pp. 1111-1121 (1985).

Engelhardt, J.F. et al., "Andenovirus-Mediated Transfer of the CFTR Gene to Lung of Nonhuman Primates: Biological Efficacy Study", Human Gene Therapy, vol. 4, pp. 759-769 (1993).

Enoch, H.G. et al., "Formation and properties of 1000-Å-diameter, single-bilayer phospholipid vesicles", Proc. Natl. Acad. Sci. USA, vol. 76, No. 1, pp. 145-149 (1979).

Erlich, H.A. et al., "Recent Advances in the Polymerase Chain Reaction", Science, vol. 252, pp. 1643-1650 (1991).

Evan, G.I. et al., "Isolation of Monoclonal Antibodies Specific for Human c-myc Proto-Oncogene Product", Molecular and Cellular Biology, vol. 5, No. 12, pp. 3610-3616 (1985).

Felgner, P.L. et al., "Lipofection: A highly efficient, lipid-mediated DNA-transfection procedure", Proc. Natl. Acad. Sci. USA, vol. 84, pp. 7413-7417 (1987).

Fell, H.P. et al., "Genetic Construction and Characterization of a Fusion Protein Consisting of a Chimeric F(ab') with Specificity for Carcinomas and Human IL-2", The Journal of Immunology, vol. 146, No. 7, pp. 2446-2452 (1991).

Ferrantini, M. et al., "α$_1$-Interferon Gene Transfer into Metastatic Friend Leukemia Cells Abrogated Tumorigenicity in Immunocompetent Mice: Antitumor Therapy by Means of Interferon-producing Cells", Cancer Research, vol. 53, pp. 1107-1112 (1993).

Ferrantini, M. et al., "IFN-α1 Gene Expression into a Metastatic Murine Adenocarcinoma (TS/A) Results in CD8+ T Cell-Mediated Tumor Rejection and Development of Antitumor Immunity: Comparative Studies with IFN-γ-Producing TS/A Cells", The Journal of Immunology, vol. 153, pp. 4604-4615 (1994).

Fishwild, D.M. et al., "High-avidity human IgGκ monoclonal antibodies from a novel strain of minifocus transgenic mice", Nature Biotechnology, vol. 14, pp. 845-851 (1996).

Foecking, M.K. et al., "Powerful and versatile enhancer-promoter unit for mammalian expression vectors", Gene, vol. 45, pp. 101-105 (1986).

Fountoulakis, M. et al., "Interferon γ Receptor Extracellular Domain Expressed as IgG Fusion Protein in Chinese Hamster Ovary Cells", The Journal of Biological Chemistry, vol. 270, No. 8, pp. 3958-3964 (1995).

Fraley, R. et al., "Introduction of Liposome-encapsulated SV40 DNA into Cells", The Journal of Biological Chemistry, vol. 255, No. 21, pp. 10431-10435 (1980).

Fraley, R.T. et al., "Entrapment of a bacterial plasmid in phospholipid vesicles: Potential for gene transfer", Proc. Natl. Acad. Sci. USA, vol. 76, No. 7, pp. 3348-3352 (1979).

Francis, M.J. et al., "Immunological Priming with Synthetic Peptides of Foot-and-Mouth Disease Virus", J. Gen. Virol., vol. 66, pp. 2347-2354 (1985).

Furka, A. et al., "General method for rapid synthesis of multicomponent peptide mixtures", Int. J. Peptide Protein Res., vol. 37, pp. 487-493 (1991).

Gautier, C. et al., "α-DNA IV: α-anomeric and β-anomeric tetrathymidylates covalently linked to intercalating oxazolopyridocarbazole. Synthesis, physicochemical properties and poly (rA) binding", Nucleic Acids Research, vol. 15, No. 16, pp. 6625-6641 (1987).

Gavel, Y. et al., "Sequence differences between glycosylated and non-glycosylated Asn-X-Thr/Ser acceptor sites: implications for protein engineering", Protein Engineering, vol. 3, No. 5, pp. 433-442 (1990).

Gayle, III, R.B. et al., "Identification of Regions in Interleukin-1α Important for Activity", The Journal of Biological Chemistry, vol. 268, No. 29, pp. 22105-22111 (1993).

Gentz, R. et al., "Bioassay for trans-activation using purified human immunodeficiency virus tat-encoded protein: Trans-activation requires mRNA synthesis", Proc. Natl. Acad. Sci. USA, vol. 86, pp. 821-824 (1989).

Geysen, H.M. et al., "Use of peptide synthesis to probe viral antigens for epitopes to a resolution of a single amino acid", Proc. Natl. Acad. Sci. USA, vol. 81, pp. 3998-4002 (1984).

Gillies, S.D. et al., "Antibody-targeted interleukin 2 stimulates T-cell killing of autologous tumor cells", Proc. Natl. Acad. Sci. USA, vol. 89, pp. 1428-1432 (1992).

Gillies, S.D. et al., "High-level expression of chimeric antibodies using adapted cDNA variable region cassettes", Journal of Immunological Methods, vol. 125, pp. 191-202 (1989).

Glover, D.M., ed., DNA Cloning, vol. III: a practical approach, IRL Press Limited, publ., pp. ix-xv (table of contents) (1987).

Goding, J.W., Chapter 3: "Production of Monoclonal Antibodies", Monoclonal Antibodies: Principles and Practice, Second Edition, Academic Press Limited, publ., pp. 59-103 (1986).

Goldspiel, B.R. et al., "Human gene therapy", Clinical Pharmacy, vol. 12, pp. 488-505 (1993).

Goodson, J.M., Chapter 6: "Dental Applications", Medical Applications of Controlled Release, vol. II: Applications and Evaluation, CRC Press, Inc. publ., Langer, R.S. et al., eds., pp. 115-138 (1984).

Grand, R.J.A., "Acylation of viral and eukaryotic proteins", Biochem J., vol. 258, pp. 625-638 (1989).

Green, M. et al., "Analysis of human tonsil and cancer DNAs and RNAs for DNA sequences of group C (serotypes 1,2,5, and 6) human adenoviruses", Proc. Natl. Acad. Sci. USA, vol. 76, No. 12, pp. 6606-6610 (1979).

Greenspan, N.S. et al., "Idiotypes: structure and immunogenicity", The FASEB Journal, vol. 7, pp. 437-444 (1993).

Gribskov, M. et al., eds., Sequence Analysis Primer, Stockton Press, publ., pp. vii-xi (table of contents) (1991).

Grossman, M. et al., "Retroviruses: delivery vehicle to the liver", Current Opinion in Genetics and Development, vol. 3, pp. 110-114 (1993).

Hagihara, M. et al., "Vinylogous Polypeptides: An Alternative Peptide Backbone", J. Am. Chem. Soc., vol. 114, No. 16, pp. 6568-6570 (1992).

Hämmerling, G.J. et al., eds., Appendix: "Production of Antibody-Producing Hybridomas in the Rodent Systems", Monoclonal Antibodies and T-Cell Hybridomas: Perspectives and technical advances, Elsevier/North-Holland Biomedical Press, publ., pp. 563-587 (1981).

Hansson, L.O. et al., "Evolution of Differential Substrate Specificities in Mu Class Glutathione Transferases Probed by DNA Shuffling", J. Mol. Biol., vol. 287, pp. 265-276 (1999).

Harayama, S. et al., "Artificial evolution by DNA shuffling", TIBTECH, vol. 16, pp. 76-82 (1998).

Harlow, E. et al., Antibodies: A Laboratory Manual, Cold Spring Harbor Laboratory, publ., pp. iii-ix (table of contents) (1988).

Harrop, J.A. et al., "Antibodies to TR2 (Herpesvirus Entry Mediator), a New Member of the TNF Receptor Superfamily, Block T Cell Proliferation, Expression of Activation Markers, and Production of Cytokines", The Journal of Immunology, vol. 161, pp. 1786-1794 (1998).

Hart, B.R. et al., "Synthetic Peptide Receptors: Molecularly Imprinted Polymers for the Recognition of Peptides Using Peptide-Metal Interactions", J. Am. Chem. Soc., vol. 123, No. 9, pp. 2072-2073 (2001).

Haseloff, J. et al., "Simple RNA enzymes with new and highly specific endoribonuclease activities", Nature, vol. 334, pp. 585-591 (1988).

Hellström, K.E. et al., Chapter 15: "Antibodies for Drug Delivery", Controlled Drug Delivery: Fundamentals and Applications, Second Edition, Marcel Dekker, Inc., publ., Robinson, J.R. et al., eds., pp. 623-653 (1987).

Hendrickson, B.A. et al., "Clinical Aspects and Pathophysiology of Inflammatory Bowel Disease", Clinical Microbiology Reviews, vol. 15, No. 1, pp. 79-94 (2002).

Higgins, D.G. et al., "CLUSTAL V: improved software for multiple sequence alignment", CABIOS, vol. 8, No. 2, pp. 189-191 (1992).

Higgins, D.G. et al., eds., Methods in Molecular Biology: Pichia Protocols, Humana Press Inc., publ., pp. vii-viii (table of contents) (1998).

Hirschmann, R. et al., "Nonpeptidal Peptidomimetics with a β-D-Glucose Scaffolding. A Partial Somatostatin Agonist Bearing a Close Structural Relationship to a Potent, Selective Substance P Antagonist", J. Am. Chem. Soc., vol. 114, pp. 9217-9218 (1992).

Hopp, T.P. et al., "A Short Polypeptide Marker Sequence Useful for Recombinant Protein Identification and Purification", Bio/Technology, vol. 6, pp. 1204-1210 (1988).

Hoppe, H.-J. et al., "A parallel three stranded α-helical bundle at the nucleation site of collagen triple-helix formation", FEBS Letters, vol. 344, pp. 191-195 (1994).

Houghton, R.A., "General method for the rapid solid-phase synthesis of large numbers of peptides: Specificity of antigen-antibody interaction at the level of individual amino acids", Proc. Natl. Acad. Sci. USA, vol. 82, pp. 5131-5135 (1985).

Houghton, R.A. et al., "Generation and use of synthetic peptide combinatorial libraries for basic research and drug discovery", Nature, vol. 354, pp. 84-86 (1991).

Howard III, M.A. et al., "Intracerebral drug delivery in rats with lesion-induced memory deficits", J. Neurosurg., vol. 71, pp. 105-112 (1989).

Hudson, P.J., "Recombinant antibody constructs in cancer therapy", Current Opinion in Immunology, vol. 11, pp. 548-557 (1999).

Hunkapiller, M. et al., "A microchemical facility for the analysis and synthesis of genes and proteins", Nature, vol. 310, pp. 105-111 (1984).

Hunter, W.M. et al., "Preparation of Iodine-131 Labelled Human Growth Hormone of High Specific Activity", vol. 194, No. 4827, pp. 495-496 (1962).

Huston, J.S. et al., "Protein engineering of antibody binding sites: Recovery of specific activity in an anti-digoxin single-chain Fv analogue produced in *Escherichia coli*", Proc. Natl. Acad. Sci. USA, vol. 85, 5879-5883 (1988).

Huston, J.S. et al., "Protein Engineering of Single-Chain Fv Analogs and Fusion Proteins", Methods in Enzymology, vol. 203, pp. 46-88 (1991).

Innis, M.A. et al., eds., PCR Protocols: A Guide to Methods and Applications, Academic Press, Inc., publ., pp. v-x (table of contents) (1990).

Inoue, H. et al., "Sequence-dependent hydrolysis of RNA using modified oligonucleotide splints and RNase H", FEBS Letters, vol. 215, No. 2, pp. 327-330 (1987).

Inoue, H. et al., "Synthesis and hybridization studies on two complementary nona(2'-O-methyl)ribonucleotides", Nucleic Acids Research, vol. 15, No. 15, pp. 6131-6148 (1987).

Inoue, S. et al., "Up-promoter mutations in the *lpp* gene of *Escherichia coli*", Nucleic Acids Research, vol. 13, No. 9, pp. 3101-3109 (1985).

Jalkanen, M. et al., "Cell Surface Proteoglycan of Mouse Mammary Epithelial Cells Is Shed by Cleavage of Its Matrix-binding Ectodomain from Its Membrane-associated Domain", The Journal of Cell Biology, vol. 105, No. 6, Pt. 2, pp. 3087-3096 (1987).

Jalkanen, M. et al., "Heparan Sulfate Proteoglycans from Mouse Mammary Epithelial Cells: Localization on the Cell Surface with a Monoclonal Antibody", The Journal of Cell Biology, vol. 101, pp. 976-984 (1985).

Janknecht, R. et al., "Rapid and efficient purification of native histidine-tagged protein expressed by recombinant vaccinia virus", Proc. Natl. Acad. Sci. USA, vol. 88, pp. 8972-8976 (1991).

Jenkins, A.L. et al., "Molecularly imprinted polymer sensors for pesticide and insecticide detection in water", The Analyst, vol. 126, pp. 798-802 (2001).

Jespers, L.S. et al., "Guiding the Selection of Human Antibodies from Phage Display Repertoires to a Single Epitope of an Antigen", Bio/Technology, vol. 12, pp. 899-903 (1994).

Johanson, K. et al., "Binding Interactions of Human Interleukin 5 with Its Receptor α Subunit", The Journal of Biological Chemistry, vol. 270, No. 16, pp. 9459-9471 (1995).

Joliot, A. et al., "Antennapedia homeobox peptide regulates neural morphogenesis", Proc. Natl. Acad. Sci. USA, vol. 88, pp. 1864-1868 (1991).

Jones, C. et al., "Current trends in molecular recognition and bioseparation", Journal of Chromatography A, vol. 707, pp. 3-22 (1995).

Jones, P.T. et al., "Replacing the complementarity-determining regions in a human antibody with those from a mouse", Nature, vol. 321, pp. 522-525 (1986).

Kaido, T. et al., "IFN-$\alpha_1$ Gene Transfection Completely Abolishes the Tumorigenicity of Murine B16 Melanoma Cells in Allogeneic DBA/2 Mice and Decreases Their Tumorigenicity in Syngeneic C57BL/6 Mice", Int. J. Cancer, vol. 60, pp. 221-229 (1995).

Kaneda, Y. et al., "Increased Expression of DNA Cointroduced with Nuclear Protein in Adult Rat Liver", Science, vol. 243, pp. 375-378 (1989).

Kastin, D.A. et al., "Malnutrition and gastrointestinal disease", Curr. Opin. Clin. Nutr. Metab. Care,. vol. 5, pp. 699-706 (2002).

Kettleborough, C.A. et al., "Isolation of tumor cell-specific single-chain Fv from immunized mice using phage-antibody libraries and the re-construction of whole antibodies from these antibody fragments", Eur. J. Immunol., vol. 24, pp. 952-958 (1994).

Kiem, H.-P. et al., "Retrovirus-Mediated Gene Transduction Into Canine Peripheral Blood Repopulating Cells", Blood, vol. 83, No. 6, pp. 1467-1473 (1994).

Kishimoto, A. et al., "Studies on the Phosphorylation of Myelin Basic Protein by Protein Kinase C and Adenosine 3':5'-Monophosphate-dependent Protein Kinase", The Journal of Biological Chemistry, vol. 260, No. 23, pp. 12492-12499 (1985).

Köhler, G., "Immunoglobulin chain loss in hybridoma lines", Proc. Natl. Acad. Sci. USA, vol. 77, No. 4, pp. 2197-2199 (1980).

Köhler, G. et al., "Continuous cultures of fused cells secreting antibody of predefined specificity", Nature, vol. 256, pp. 495-497 (1975).

Köhler, G. et al., "Derivation of specific antibody-producing tissue culture and tumor lines by cell fusion", Eur. J. Immunol., vol. 6, pp. 511-519 (1976).

Köhler, G. et al., "Fusion between immunoglobulin-secreting and nonsecreting myeloma cell lines", Eur. J. Immunol., vol. 6, pp. 292-295 (1976).

Kolanowski, J., "A Risk-Benefit Assessment of Anti-Obesity Drugs", Drug Safety, vol. 20, No. 2, pp. 119-131 (1999).

Koller, B.H. et al., "Inactivating the $\beta_2$-microglobulin locus in mouse embryonic stem cells by homologous recombination", Proc. Natl. Acad. Sci. USA, vol. 86, pp. 8932-8935 (1989).

Kostelny, S.A. et al., "Formation of a Bispecific Antibody by the Use of Leucine Zippers", The Journal of Immunology, vol. 148, No. 5, pp. 1547-1553 (1992).

Koutz, P. et al., "Structural Comparison of the *Pichia pastoris* Alcohol Oxidase Genes", Yeast, vol. 5, pp. 167-177 (1989).

Kozarsky, K.F. et al., "Gene therapy: adenovirus vectors", Current Opinion in Genetics and Development, vol. 3, pp. 499-503 (1993).

Kozbor, D. et al., "A Human Hybrid Myeloma for Production of Human Monoclonal Antibodies", The Journal of Immunology, vol. 133, No. 6, pp. 3001-3005 (1984).

Kozbor, D. et al., "The production of monoclonal antibodies from human lymphocytes", Immunology Today, vol. 4, No. 3, pp. 72-79 (1983).

Kreil, G. et al., "Occurrence, Detection, and Biosynthesis of Carboxy-Terminal Amides", Methods in Enzymology, vol. 106, pp. 218-223 (1984).

Kriegler, M., Gene Transfer and Expression: A Laboratory Manual, Stockton Press, publ., pp. vii-x (table of contents) (1990).

Kütemeier, G. et al., "Assembly of Humanized Antibody Genes from Synthetic Oligonucleotides Using a Single-Round PCR", BioTechniques, vol. 17, No. 2, pp. 242-246 (1994).

Kyte, J. et al., "A Simple Method for Displaying the Hydropathic Character of a Protein", J. Mol. Biol., vol. 157, pp. 105-132 (1982).

Landschulz, W.H. et al., "The Leucine Zipper: A Hypothetical Structure Common to a New Class of DNA Binding Proteins", Science, vol. 240, pp. 1759-1764 (1988).

Langer, R., "New Methods of Drug Delivery", Science, vol. 249, pp. 1527-1533 (1990).

Langer, R. et al., "Chemical and Physical Structure of Polymers as Carriers for Controlled Release of Bioactive Agents: A Review", JMS—Rev. Macromol. Chem. Phys., vol. C23, No. 1, pp. 61-126 (1983).

Langer, R.S. et al., eds., Medical Applications of Controlled Release, vol. I: Classes of Systems, CRC Press, Inc., publ. (1984) (table of contents).

Langer, R.S. et al., eds., Medical Applications of Controlled Release, vol. II: Applications and Evaluation, CRC Press, Inc., publ. (1984) (table of contents).

Lardizabal, K.D. et al., "DGAT2 Is a New Diacylglycerol Acyltransferase Gene Family: Purification, Cloning, and Expression in Insect Cells of Two Polypeptides from *Mortierella Ramanniana* with Diacylglycerol Acyltransferase Activity", The Journal of Biological Chemistry, vol. 276, No. 4, pp. 38862-38869 (2001).

Lee, J.S. et al., "Complexes formed by (pyrimidine)$_n$ • (purine)$_n$ DNAs on lowering the pH are three-stranded", Nucleic Acids Research, vol. 6, No. 9, pp. 3073-3091 (1979).

Lehner, R. et al., "Biosynthesis of Triacylglycerols", Prog. Lipid Res., vol. 35, No. 2, pp. 169-201 (1996).

Lemaitre, M. et al., "Specific antiviral activity of a poly(L-lysine)-conjugated oligodeoxyribonucleotide sequence complementary to vesicular stomatitis virus N protein mRNA initiation site", Proc. Natl. Acad. Sci. USA, vol. 84, pp. 648-652 (1987).

Lesk, A.M., ed., Computational Molecular Biology: Sources and Methods for Sequence Analysis, Oxford University Press, publ., pp. ix-x (table of contents) (1988).

Letsinger, R.L. et al., "Cholesteryl-conjugated oligonucleotides: Synthesis, properties, and activity as inhibitors of replication of human immunodeficiency virus in cell culture", Proc. Natl. Acad. Sci. USA, vol. 86, pp. 6553-6556 (1989).

Levy, E., "Selected aspects of intraluminal and intracellular phases of intestinal fat absorption", Can. J. Physiol. Pharmacol., vol. 70, pp. 413-419 (1992).

Levy, R.J. et al., "Inhibition of Calcification of Bioprosthetic Heart Valves by Local Controlled-Release Diphosphonate", Science, vol. 228, pp. 190-192 (1985).

Liang, R. et al., "Parallel Synthesis and Screening of a Solid Phase Carbohydrate Library", Science, vol. 274, pp. 1520-1522 (1996).

Liautard, J. et al., "Specific Inhibition of IL-6 Signalling with Monoclonal Antibodies Against the gp130 Receptor", Cytokine, vol. 9, No. 4, pp. 233-241 (1997).

Linenberger, M.L. et al., "In vivo Infection of Marrow Stromal Fibroblasts by Feline Leukemia Virus", Experimental Hematology, vol. 20, pp. 1022-1027 (1992).

Loeffler, J.-P. et al., "Gene Transfer into Primary and Established Mammalian Cell Lines with Lipopolyamine-Coated DNA", Methods in Enzymology, vol. 217, pp. 599-618 (1993).

Logan, J. et al., "Adenovirus tripartite leader sequence enhances translation of mRNAs late after infection", Proc. Natl. Acad. Sci. USA, vol. 81, pp. 3655-3659 (1984).

Lonberg, N. et al., "Antigen-specific human antibodies from mice comprising four distinct genetic modifications", Nature, vol. 368, pp. 856-859 (1994).

Lonberg, N. et al., "Human Antibodies from Transgenic Mice", Intern. Rev. Immunol., vol. 13, pp. 65-93 (1995).

Lopez-Berestein, G., "Treatment of Systemic Fungal Infections with Liposomal-Amphotericin B", Liposomes in the Therapy of Infectious Diseases and Cancer, Proceedings of a Ciba-Geigy-Squibb-UCLA Colloquium, Lake Tahoe, CA, Feb. 16-20, 1988, Alan R. Liss, Inc., publ., Lopez-Berestein, G. et al., eds., pp. 317-327 (1989).

Lorenzo, M.D.M. et al., "PCR-Based Method for the Introduction of Mutations in Genes Cloned and Expressed in Vaccinia Virus", BioTechniques, vol. 24, No. 2, pp. 308-313 (1998).

Lowy, I. et al., "Isolation of Transforming DNA: Cloning the Hamster aprt Gene", Cell, vol. 22, pp. 817-823 (1980).

Lucas, K.H. et al., "Orlistat—A Novel Weight Loss Therapy", The Annals of Pharmacotherapy, vol. 35, pp. 314-328 (2001).

Lutz-Freyermuth, C. et al., "Quantitative determination that one of two potential RNA-binding domains of the A protein component of the U1 small nuclear ribonucleoprotein complex binds with high affinity to stem-loop II of U1 RNA", Proc. Natl. Acad. Sci. USA, vol. 87, pp. 6393-6397 (1990).

Marks, J.D. et al., "By-Passing Immunization: Building High Affinity Human Antibodies by Chain Shuffling", Bio/Technology, vol. 10, pp. 779-783 (1992).

Marshall, R.D., "Glyproteins", Annu. Rev. Biochem., vol. 41, pp. 673-702 (1972).

Martin, G.A. et al., "GAP Domains Responsible for Ras p21-Dependent Inhibition of Muscarinic Atrial K$^+$Channel Currents", Science, vol. 255, pp. 192-194 (1992).

Martin-Esteban, A., "Molecularly imprinted polymers: new molecular recognition materials for selective solid-phase extraction of organic compounds", J. Anal. Chem., vol. 370, pp. 795-802 (2001).

Mashiba, H. et al., "Augumented Inhibition of Tumor Cell Proliferation in Combined Use of Electroporation with a Plant Toxin, Saporin", Annals New York Academy of Sciences, vol. 886, pp. 233-235 (1999).

Mastrangeli, A. et al., "Diversity of Airway Epithelial Cell Targets for In Vivo Recombinant Adenovirus-mediated Gene Transfer", J. Clin. Invest., vol. 91, pp. 225-234 (1993).

McGeoch, D.J., "On the predictive recognition of signal peptide sequences", Virus Research, vol. 3, pp. 271-286 (1985).

Miletich, J.P. et al., "β Protein C is Not Glycosylated at Asparagine 329", The Journal of Biological Chemistry, vol. 265, No. 19, pp. 11397-11404 (1990).

Miller, A.D., "Retrovirus Packaging Cells", Human Gene Therapy, vol. 1, pp. 5-14 (1990).

Miller, A.D. et al., "Use of Retroviral Vectors for Gene Transfer and Expression", Methods in Enzymology, vol. 217, pp. 581-599 (1993).

Milstein, C. et al., "Hybrid hybridomas and their use in immunohistochemistry", Nature, vol. 305, pp. 537-540 (1983).

Morgan, R.A. et al., "Human Gene Therapy", Annu. Rev. Biochem., vol. 62, pp. 191-217 (1993).

Morrison, S.J. et al., "Prospective Identification, Isolation by Flow Cytometry, and In Vivo Self-Renewal of Multipotent Mammalian Neural Crest Stem Cells", Cell, vol. 96, pp. 737-749 (1999).

Morrison, S.L., "Transfectomas Provide Novel Chimeric Antibodies", Science, vol. 229, pp. 1202-1207 (1985).

Morrison, S.L. et al., "Chimeric human antibody molecules: Mouse antigen-binding domains with human constant region domains", Proc. Natl. Acad. Sci. USA, vol. 81, pp. 6851-6855 (1984).

Muller, Y.A. et al., "VEGF and the Fab fragment of a humanized neutralizing antibody: crystal structure of the complex at 2.4 Å resolution and mutational analysis of the interface", Structure, vol. 6, No. 9, pp. 1153-1167 (1998).

Mulligan, R.C., "The Basic Science of Gene Therapy", Science, vol. 260, pp. 926-932 (1993).

Mulligan, R.C. et al., "Selection for animal cells that express the *Escherichia coli* gene coding for xanthine-guanine phosphoribosyltransferase", Proc. Natl. Acad. Sci. USA, vol. 78, No. 4, pp. 2072-2076 (1981).

Mullinax, R.L. et al., "Expression of a Heterodimeric Fab Antibody Protein in One Cloning Step", BioTechniques, vol. 12, No. 6, pp. 864-869 (1992).

Mullis, K. et al., "Specific Enzymatic Amplification of DNA In Vitro: The Polymerase Chain Reaction", Cold Spring Harbor Symposia on Quantitative Biology, vol. 51, pp. 263-273 (1986).

Munson, P.J. et al., "LIGAND: A Versatile Computerized Approach for Characterization of Ligand-Binding Systems", Analytical Biochemistry, vol. 107, pp. 220-239 (1980).

Muzyczka, N., "Use of Adeno-Associated Virus as a General Transduction Vector for Mammalian Cells", Current Topics in Microbiology and Immunology, vol. 158, pp. 97-129 (1992).

Naramura, M. et al., "Mechanisms of cellular cytotoxicity mediated by a recombinant antibody—IL2 fusion protein against human melanoma cells", Immunology Letters, vol. 39, pp. 91-99 (1994).

Neuberger, M., "Generating high-avidity human Mabs in mice", Nature Biotechnology, vol. 14, p. 826 (1996).

Neuberger, M.S. et al., "A hapten-specific chimaeric IgE antibody with human physiological effector function", Nature, vol. 314, pp. 268-270 (1985).

Neuberger, M.S. et al., "Recombinant antibodies possessing novel effector functions", Nature, vol. 312, pp. 604-608 (1984).

Nielsen, H. et al., "Identification of prokaryotic and eukaryotic signal peptides and prediction of their cleavage sites", Protein Engineering, vol. 10, No. 1, pp. 1-6 (1997).

Nielsen, H. et al., "Prediction of signal peptides and signal anchors by a hidden Markov model", ISMB, pp. 122-130 (1998).

Nielsen, P.E. et al., "Sequence-Selective Recognition of DNA by Strand Displacement with a Thymine-Substituted Polyamide", Science, vol. 254, pp. 1497-1500 (1991).

Nisonoff, A. et al., "Idiotypes: Concepts and Applications", The Journal of Immunology, vol. 147, No. 8, pp. 2429-2438 (1991).

Nygren, H., "Conjugation of Horseradish Peroxidase to Fab Fragments with Different Homobifunctional and Heterobifunctional Cross-Linking Reagents: A Comparative Study", The Journal of Histochemistry and Cytochemistry, vol. 30, No. 5, pp. 407-412 (1982).

Ogura, H. et al., "Implantation of Genetically Manipulated Fibroblasts into Mice as Antitumor α-Interferon Therapy", Cancer Research, vol. 50, pp. 5102-5106 (1990).

O'Hare, K. et al., "Transformation of mouse fibroblasts to methotrexate resistance by a recombinant plasmid expressing a prokaryotic dihydrofolate reductase", Proc. Natl. Acad. Sci. USA, vol. 78, No. 3, pp. 1527-1531 (1981).

Oi, V.T. et al., "Chimeric Antibodies", BioTechniques, vol. 4, No. 3, pp. 214-221 (1986).

Okano, H. et al., "Myelin Basic Protein Gene and the Function of Antisense RNA in Its Repression in Myelin-Deficient Mutant Mouse", Journal of Neurochemistry, vol. 56, No. 2, pp. 560-567 (1991).

Order, S.E., Chapter 15: "Analysis, Results, and Future Prospective of the Therapeutic Use of Radiolabeled Antibody in Cancer Therapy", Monoclonal Antibodies for Cancer Detection and Therapy, Academic Press Inc., publ., Baldwin, R.W. et al., eds., pp. 303-316 (1985).

Ostro, M.J. et al., "Incorporation of High Molecular Weight RNA into Large Artificial Lipid Vesicles", Biochemical and Biophysical Research Communications, vol. 76, No. 3, pp. 836-842 (1977).

Paborsky, L.R. et al., "Mammalian cell transient expression of tissue factor for the production of antigen", Protein Engineering, vol. 3, No. 6, pp. 547-553 (1990).

Paddison, P.J. et al., "Stable suppression of gene expression by RNAi in mammalian cells", Proc. Natl. Acad. Sci. USA, vol. 99, No. 3, pp. 1443-1448 (2002).

Padlan, E.A. et al., "A Possible Procedure for Reducing the Immunogenicity of Antibody Variable Domains While Preserving Their Ligand-Binding Properties", Molecular Immunology, vol. 28, No. 4/5, pp. 489-498 (1991).

Pain, D. et al., "Preparation of Protein A-Peroxidase Monoconjugate Using a Heterobifunctional Reagent, and Its Use in Enzyme Immunoassays", Journal of Immunological Methods, vol. 40, pp. 219-230 (1981).

Papahadjopoulos, D. et al., "Cochleate Lipid Cylinders: Formation by Fusion of Unilamellar Lipid Vesicles", Biochimica et Biophysica Acta, vol. 394, pp. 483-491 (1975).

Patten, P.A. et al., "Applications of DNA shuffling to pharmaceuticals and vaccines", Current Opinion in Biotechnology, vol. 8, pp. 724-733 (1997).

Persic, L. et al., "An integrated vector system for the eukaryotic expression of antibodies or their fragments after selection from phage display libraries"; Gene, vol. 187, pp. 9-18 (1997).

Pinckard, R.N. et al., "Factors Influencing the Immune Response: I. Effects of the Physical State of the Antigen and of Lymphoreticular Cell Proliferation on the Response to Intravenous Injection of Bovine Serum Albumin in Rabbits", Clin. Exp. Immunol., vol. 2, pp. 331-341 (1967).

Pinna, L.A., "Casein kinase 2: an 'eminence grise' in cellular recognition?", Biochimica et Biophysica Acta, vol. 1054, pp. 267-284 (1990).

Pitard, V. et al., "Production and characterization of monoclonal antibodies against the leukemia inhibitory factor low affinity receptor, gp190", Journal of Immunological Methods, vol. 205, pp. 177-190 (1997).

Pittelkow, M.R. et al., "New Techniques for the In Vitro Culture of Human Skin Keratinocytes and Perspectives on Their Use for Grafting of Patients With Extensive Burns", Mayo Clinic Proceedings, vol. 61, pp. 771-777 (1986).

Pless, D.D. et al., "Enzymatic conversion of proteins to glycoproteins", Proc. Natl. Acad. Sci. USA, vol. 74, No. 1, pp. 134-138 (1977).

Prat, M. et al., "Agonistic monoclonal antibodies against the Met receptor dissect the biological responses to HGF", Journal of Cell Science, vol. 111, pp. 237-247 (1998).

Presta, L.G., "Antibody engineering", Current Opinion in Structural Biology, vol. 2, pp. 593-596 (1992).

Proudfoot, N.J., "Transcriptional interference and termination between duplicated α-globin gene constructs suggests a novel mechanism for gene regulation", Nature, vol. 322, pp. 562-565 (1986).

Quaglia, M. et al., "Target Analogue Imprinted Polymers with Affinity for Folic Acid and Related Compounds", J. Am. Chem. Soc., vol. 123, No. 10, pp. 2146-2154 (2001).

Rachkov, A. et al., "Towards molecularly imprinted polymers selective to peptides and proteins. The epitope approach", Biochimica et Biophysica Acta, vol. 1544, pp. 255-266 (2001).

Radrizzani, M. et al., "Oligobodies: Bench Made Synthetic Antibodies", Medicina (Buenos Aires), vol. 59, No. 6, pp. 753-758 (1999).

Rattan, S.I.S. et al., "Protein Synthesis, Posttranslational Modifications, and Aging", Annals New York Academy of Sciences, vol. 663, pp. 48-62 (1992).

Rheinwald, J.G., Chapter 15: "Serial Cultivation of Normal Human Epidermal Keratinocytes", Methods in Cell Biology, vol. 21A, pp. 229-254 (1980).

Riechmann, L. et al., "Reshaping human antibodies for therapy", Nature, vol. 332, pp. 323-327 (1988).

Robbins, D.C. et al., "Antibodies to Covalent Aggregates of Insulin in Blood of Insulin-Using Diabetic Patients", Diabetes, vol. 36, pp. 838-841 (1987).

Roguska, M.A. et al., "Humanization of murine monoclonal antibodies through variable domain resurfacing", Proc. Natl. Acad. Sci. USA, vol. 91, pp. 969-973 (1994).

Ron, D. et al., "Expression of Biologically Active Recombinant Keratinocyte Growth Factor", The Journal of Biological Chemistry, vol. 268, No. 4, pp. 2984-2988 (1993).

Rosenfeld, M.A. et al., "Adenovirus-Mediated Transfer of a Recombinant α1-Antitrypsin Gene to the Lung Epithelium in Vivo", Science, vol. 252, pp. 431-434 (1991).

Rosenfeld, M.A. et al., "In Vivo Transfer of the Human Cystic Fibrosis Transmembrane Conductance Regulator Gene to the Airway Epithelium", Cell, vol. 68, pp. 143-155 (1992).

Rüther et al., "Easy identification of cDNA clones", The EMBO Journal, vol. 2, No. 10, pp. 1791-1794 (1983).

Saiki, R.K. et al., "Primer-Directed Enzymatic Amplification of DNA with a Thermostable DNA Polymerase", Science, vol. 239, pp. 487-491 (1988).

Salmons, B. et al., "Targeting of Retroviral Vectors for Gene Therapy", Human Gene Therapy, vol. 4, pp. 129-141 (1993).

Sambrook, J. et al., Molecular Cloning: A Laboratory Manual, Second Edition, Cold Spring Harbor Laboratory Press, publ., pp. xi-xxxviii (table of contents) (1989).

Sambrook, J. et al., Chapter 9: "Analysis and Cloning of Eukaryotic Genomic DNA", Molecular Cloning: A Laboratory Manual, vol. 2, Second Edition, Cold Spring Harbor Laboratory Press, publ., pp. 9.1-9.62 (1989).

Sambrook, J. et al., Chapter 11: "Synthetic Oligonucleotide Probes", Molecular Cloning: A Laboratory Manual, vol. 2, Second Edition, Cold Spring Harbor Laboratory Press, publ., pp. 11.1-11.61 (1989).

Santerre, R.F. et al., "Expression of prokaryotic genes for hygromycin B and G418 resistance as dominant-selection markers in mouse L cells", Gene, vol. 30, pp. 147-156 (1984).

Santodonato, L. et al., "Cure of Mice with Established Metastatic Friend Leukemia Cell Tumors by a Combined Therapy with Tumor Cells Expressing Both Interferon-α1 and Herpes Simplex Thymidine Kinase Followed by Ganciclovir", Human Gene Therapy, vol. 7, pp. 1-10 (1996).

Santodonato, L. et al., "Local and systemic antitumor response after combined therapy of mouse metastatic tumors with tumor cells expressing IFN-α and HSVtk: perspectives for the generation of cancer vaccines", Gene Therapy, vol. 4, pp. 1246-1255 (1997).

Sarin, P.S. et al., "Inhibition of acquired immunodeficiency syndrome virus by oligodeoxynucleoside methylphosphonates", Proc. Natl. Acad. Sci. USA, vol. 85, pp. 7448-7451 (1988).

Sarver, N. et al., "Ribozymes as Potential Anti-HIV-1 Therapeutic Agents", Science, vol. 247, pp. 1222-1225 (1990).

Satsangi, J. et al., "Two stage genome-wide search in inflammatory bowel disease provides evidence for susceptibility loci on chromosomes 3, 7 and 12", Nature Genetics, vol. 14, pp. 199-202 (1996).

Saudek, C.D. et al., "A Preliminary Trial of the Programmable Implantable Medication System for Insulin Delivery", The New England Journal of Medicine, vol. 321, No. 9, pp. 574-579 (1989).

Sawai, H. et al., "Direct Production of the Fab Fragment Derived From the Sperm Immobilizing Antibody Using Polymerase Chain Reaction and cDNA Expression Vectors", American Journal of Reproductive Immunology, vol. 34, pp. 26-34 (1995).

Schaefer-Ridder, M. et al., "Liposomes as Gene Carriers: Efficient Transformation of Mouse L Cells by Thymidine Kinase Gene", Science, vol. 215, pp. 166-168 (1982).

Schwartz, A.R. et al., "Clinical Evaluation of Live, Oral Types 1, 2, and 5 Adenovirus Vaccines", American Review of Respiratory Disease, vol. 109, pp. 233-238 (1974).

Sefton, M.V., "Implantable Pumps", CRC Critical Reviews in Biomedical Engineering, vol. 14, No. 3, pp. 201-240 (1987).

Seifter, S. et al., "Analysis for Protein Modifications and Nonprotein Cofactors", Methods in Enzymology, vol. 182, pp. 626-646 (1990).

Shu, L. et al., "Secretion of a single-gene-encoded immunoglobulin from myeloma cells", Proc. Natl. Acad. Sci. USA, vol. 90, pp. 7995-7999 (1993).

Skerra, A. et al., "Assembly of a Fucntional Immunoglobulin F$_v$ Fragment in *Escherichia coli*", Science, vol. 240, pp. 1038-1041 (1988).

Smith, D.B. et al., "Single-step purification of polypeptides expressed in *Escherichia coli* as fusions with glutathione S-transferase", Gene, vol. 67, pp. 31-40 (1988).

Smith, D.W., ed., Biocomputing: Informatics and Genome Projects, Academic Press, Inc., publ., pp. v-ix (table of contents) (1994).

Smolen, V.F. et al., eds., Controlled Drug Bioavailability, vol. 1: Drug Product Design and Performance, John Wiley & Sons, Inc., publ., p. xiii (table of contents) (1984).

Stein, C.A. et al., "Physicochemical properties of phosphorothioate oligodeoxynucleotides", Nucleic Acids Research, vol. 16, No. 8, pp. 3209-3221 (1988).

Stemple, D.L. et al., "Isolation of a Stem Cell for Neurons and Glia from the Mammalian Neural Crest", Cell, vol. 71, pp. 973-985 (1992).

Straubinger, R.M. et al., "Liposomes as Carriers for Intracellular Delivery of Nucleic Acids", Methods in Enzymology, vol. 101, pp. 512-527 (1983).

Stribling, R. et al., "Aerosol gene delivery in vivo", Proc. Natl. Acad. Sci. USA, vol. 89, pp. 11277-11281 (1992).

Studnicka, G.M. et al., "Human-engineered monoclonal antibodies retain full specific binding activity by preserving non-CDR complementarity-modulating residues", Protein Engineering, vol. 7, No. 6, pp. 805-814 (1994).

Suresh, M.R. et al., "Bispecific Monoclonal Antibodies from Hybrid Hybridomas", Methods in Enzymology, vol. 121, pp. 210-228 (1986).

Sutcliffe, J.G. et al., "Antibodies That React with Predetermined Sites on Proteins", Science, vol. 219, pp. 660-666 (1983).

Szoka, Jr., F. et al., "Procedure for preparation of liposomes with large internal aqueous space and high capture by reverse-phase evaporation", Proc. Natl. Acad. Sci. USA, vol. 75, No. 9, pp. 4194-4198 (1978).

Szybalska, E.H. et al., "Genetics of Human Cell Lines, IV. DNA-Mediated Heritable Transformation of a Biochemical Trait", Proc. Natl. Acad. Sci. USA, vol. 48, pp. 2026-2034 (1962).

Takahashi, T. et al., "Human Fas ligand: gene structure, chromosomal location and species specificity", International Immunology, vol. 6, No. 10, pp. 1567-1574 (1994).

Takeda, S.-I. et al., "Construction of chimaeric processed immunoglobulin genes containing mouse variable and human constant region sequences", Nature, vol. 314, pp. 452-454 (1985).

Thompson, J.D. et al., "CLUSTAL W: improving the sensitivity of progressive multiple sequence alignment through sequence weighting, position-specific gap penalties and weight matrix choice", Nucleic Acids Research, vol. 22, No. 22, pp. 4673-4680 (1994).

Thorpe, P.E., "Antibody Carriers of Cytotoxic Agents in Cancer Therapy: A Review", Monoclonal Antibodies '84: Biological and Clinical Applications, Proceedings of the International Symposium on Monoclonal Antibodies '84, Florence, Italy, Oct. 16-19, 1984, Editrice Kurtis s.r.l., publ., Pinchera, A. et al., eds., pp. 475-506 (1985).

Thorpe, P.E. et al., "The Preparation and Cytotoxic Properties of Antibody-Toxin Conjugates", Immunological Rev., vol. 62, pp. 119-158 (1982).

TIBTECH, vol. 11, No. 5, pp. 155-215 (1993).

Tolstoshev, P., "Gene Therapy, Concepts, Current Trials and Future Directions", Annu. Rev. Pharmacol. Toxicol., vol. 32, pp. 573-596 (1993).

Tonukari, N.J. et al., "The *Cochliobolus carbonum SNF1* Gene Is Required for Cell Wall-Degrading Enzyme Expression and Virulence on Maize", The Plant Cell, vol. 12, pp. 237-247 (2000).

Towler, D.A. et al., "The Biology and Enzymology of Eukaryotic Protein Acylation", Ann. Rev. Biochem., vol. 57, pp. 69-99 (1988).

Traunecker, A. et al., "Bispecific single chain molecules (Janusins) target cytotoxic lymphocytes on HIV infected cells", The EMBO Journal, vol. 10, No. 12, pp. 3655-3659 (1991).

Traunecker, A. et al., "Soluble CD4 molecules neutralize human immunodeficiency virus type 1", Nature, vol. 331, pp. 84-88 (1988).

Treat, J., "Liposome Encapsulated Doxorubicin: Preliminary Results of Phase I and Phase II Trials", Liposomes in the Therapy of Infectious Diseases and Cancer, Proceedings of a Ciba-Geigy-Squibb-UCLA Colloquium, Lake Tahoe, CA, Feb. 16-20, 1988, Alan R. Liss, Inc., publ., Lopez-Berestein, G. et al., eds., pp. 353-365 (1989).

Tschopp, J.F. et al., "Expression of the *lacZ* gene from two methanol-regulated promoters in *Pichia pastoris*", Nucleic Acids Research, vol. 15, No. 9, pp. 3859-3876 (1987).

Tutt, A. et al., "Trispecific F(ab')$_3$ Derivatives that Use Cooperative Signaling Via the TCR/CD3 Complex and CD2 to Activate and Redirect Resting Cytotoxic T Cells", The Journal of Immunology, vol. 147, No. 1, pp. 60-69 (1991).

Twyman, R.E. et al., "Glutamate Receptor Antibodies Activate a Subset of Receptors and Reveal an Agonist Binding Site", Neuron, vol. 14, pp. 755-762 (1995).

van der Krol, A.R. et al., "Modulation of Eukaryotic Gene Expression by Complementary RNA or DNA Sequences", BioTechniques, vol. 6, No. 10, pp. 958-976 (1988).

Van Heeke, G. et al., "Expression of Human Asparagine Synthetase in *Escherichia coli*", The Journal of Biological Chemistry, vol. 264, No. 10, pp. 5503-5509 (1989).

Vaughan, T.J. et al., "Human Antibodies with Sub-nanomolar Affinities Isolated from a Large Non-immunizied Phage Display Library", Nature Biotechnology, vol. 14, pp. 309-314 (1996).

Verhoeyen, M. et al., "Reshaping Human Antibodies: Grafting an Antilysozyme Activity", Science, vol. 239, pp. 1534-1536 (1988).

Verma, R.S. et al., Human Chromosomes: Manual of Basic Techniques, Pergamon Press, Inc., publ., pp. vii-ix (table of contents) (1989).

Vié, H. et al., "Human fusion proteins between interleukin 2 and IgM heavy chain are cytotoxic for cells expressing the interleukin 2 receptor", Proc. Natl. Acad. Sci. USA, vol. 89, pp. 11337-11341 (1992).

von Heijne, G., "A new method for predicting signal sequence cleavage sites", Nucleic Acids Research, vol. 14, No. 11, pp. 4683-4690 (1986).

von Heijne, G., Sequence Analysis in Molecular Biology: Treasure Trove or Trivial Pursuit, Academic Press, Inc., publ., pp. vii-ix (table of contents) (1987).

Wagner, M.J. et al., "Nucleotide sequence of the thymidine kinase gene of herpes simplex virus type 1", Proc. Natl. Acad. Sci. USA, vol. 78, No. 3, pp. 1441-1445 (1981).

Wagner, R.W., "Gene inhibition using oligodeoxynucleotides", Nature, vol. 372, pp. 333-335 (1994).

Wahl, R.L. et al., "Improved Radioimaging and Tumor Localization with Monoclonal F(ab')$_2$", The Journal of Nuclear Medicine, vol. 24, No. 4, pp. 316-325 (1983).

Walsh, C.E. et al., "Gene Therapy for Human Hemoglobinopathies", Proc. Soc. Exp. Biol. Med., vol. 204, pp. 289-300 (1993).

Wands, J.R. et al., "High Affinity Monoclonal Antibodies to Hepatitis B Surface Antigen (HB$_s$Ag) Produced by Somatic Cell Hybrids", Gastroenterology, vol. 80, No. 2, pp. 225-232 (1981).

Wang, Q. et al., "A packaging cell line for propagation of recombinant adenovirus vectors containing two lethal gene-region deletions", Gene Therapy, vol. 2, pp. 775-783 (1995).

Ward, E.S. et al., "Binding activities of a repertoire of single immunoglobulin variable domains secreted from *Escherichia coli*", Nature, vol. 341, pp. 544-546 (1989).

Wigler, M. et al., "Transfer of Purified Herpes Virus Thymidine Kinase Gene to Cultured Mouse Cells", Cell, vol. 11, pp. 223-232 (1977).

Wilson, I.A. et al., "The Structure of an Antigenic Determinant in a Protein", Cell, vol. 37, pp. 767-778 (1984).

Wilson, J.M., "Vehicles for gene therapy", Nature, vol. 365, pp. 691-692 (1993).

Wilson, T. et al., "The Introduction of Poliovirus RNA into Cells via Lipid Vesicles (Liposomes)", Cell, vol. 17, pp. 77-84 (1979).

Wold, F., "Posttranslational Protein Modifications: Perspectives and Prospectives", Posttranslational Covalent Modifications of Proteins, Academic Press, Inc., publ., Johnson, B.C., ed., pp. 1-12 (1983).

Woodgett, J.R. et al., "Substrate specificity of protein kinase C: Use of synthetic peptides corresponding to physiological sites as probes for substrate recognition requirements", Eur. J. Biochem., vol. 161, pp. 177-184 (1986).

Wu, G.Y. et al., "Delivery systems for gene therapy", Biotherapy, vol. 3, pp. 87-95 (1991).

Wu, G.Y. et al., "Receptor-mediated in Vitro Gene Transformation by a Soluble DNA Carrier System", The Journal of Biological Chemistry, vol. 262, No. 10, pp. 4429-4432 (1987).

Yamamoto, T. et al., "Identification of a Functional Promoter in the Long Terminal Repeat of Rous Sarcoma Virus", Cell, vol. 22, pp. 787-797 (1980).

Yang, Y. et al., "Inactivation of E2a in recombinant adenoviruses improves the prospect for gene therapy in cystic fibrosis", Nature Genetics, vol. 7, pp. 362-369 (1994).

Ye, L. et al., "Towards the development of molecularly imprinted artificial receptors for the screening of estrogenic chemicals", The Analyst, vol. 126, pp. 760-765 (2001).

Yen, C.-L.E. et al., "Identification of a gene encoding MGAT1, a monoacylglycerol acyltransferase", Proc. Natl. Acad. Sci. USA, vol. 99, No. 13, pp. 8512-8517 (2002).

Yoon, D.-Y. et al., "Antibodies to Domains II and III of the IL-1 Receptor Accessory Protein Inhibit IL-1β Activity But Not Binding: Regulation of IL-1 Responses Is Via Type I Receptor, Not the Accessory Protein", The Journal of Immunology, vol. 160, 3170-3179 (1998).

Zhang, J.F. et al., "Gene therapy with an adeno-associated virus carrying an interferon gene results in tumor growth suppression and regression", Cancer Gene Therapy, vol. 3, No. 1, pp. 31-38 (1996).

Zheng, X.X. et al., "Administration of Noncytolytic IL-10/Fc in Murine Models of Lipopolysaccharide-Induced Septic Shock and Allogeneic Islet Transplantation", The Journal of Immunology, vol. 154, pp. 5590-5600 (1995).

Zhi, J. et al., "Review of Limited Systemic Absorption of Orlistat, a Lipase Inhibitor, in Healthy Human Volunteers", J. Clin. Pharmacol., vol. 35, pp. 1103-1108 (1995).

Zhu, Z. et al., "Inhibition of Vascular Endothelial Growth Factor-induced Receptor Activation with Anti-Kinase Insert Domain-containing Receptor Single-Chain Antibodies from a Phage Display Library", Cancer Research, vol. 58, pp. 3209-3214 (1998).

Zijlstra, M. et al., "Germ-line transmission of a disrupted $\beta_2$-microglobulin gene produced by homologous recombination in embryonic stem cells", Nature, vol. 342, pp. 435-438 (1989).

Zimmermann, J., "Refining the Toolbox for HTS", Genetic Engineering News, vol. 20, No. 8, pp. 13, 40, 69 (2000).

Zola, H., Chapter 6: "Using Monoclonal Antibodies: Soluble Antigens", Monoclonal Antibodies: A Manual of Techniques, CRC Press, Inc., publ., pp. 147-158 (1987).

Zon, G., "Oligonucleotide Analogues as Potential Chemotherapeutic Agents", Pharmaceutical Research, vol. 5, No. 9, pp. 539-549 (1988).

Zurfluh, L.L. et al., "Auxin-induced changes in the patterns of protein synthesis in soybean hypocotyl", Proc. Natl. Acad. Sci. USA, vol. 77, No. 1, pp. 357-361 (1980).

U.S. Appl. No. 03/170,691, filed Sep. 11, 2003, Gimeno, et al.

Cao, J., et al., "Cloning and Functional Characterization of a Mouse Intestinal Acyl-CoA:Monoacylglycerol Acyltransferase, MGAT2", J. Biol. Chem., vol. 278, pp. 13860-13866 (2003).

Cheng, D., et al., "Identification of Acyl Coenzyme A:Monoacylglycerol Acyltransferase 3, an Intestinal Specific Enzyme Implicated in Dietary Fat Absorption", J. Biol. Chem., No. 278, pp. 13611-13614 (2003).

Gimeno, et al., "Human diacylglycerol acyltransferase 2 (DGAT2) cDNA, 60489", Database Genbank Online, XP002903911, Database Accession No. (AAD56887), (2003).

Gimeno, et al., "Human diacylglycerol acyltransferase 2 (DGAT2), 60489", Database Genbank Online, XP002903912, Database Accession No. (AAE377787), (2003).

Logan, et al., "Human 60489 protein", Database Genbank Online, XP002903913, Database accession No. AAE37357, (2003).

Tang et al., "Nucleic acids encoding polypeptides with cytokine-like activities, useful in diagnosis and gene therapy", Database Genbank Online, XP002903910, Database Accession No. (AAK53395) (2001).

Wilson, R., et al., "Toward a complete human genome sequence", Database Protein (Online), XP002903908, Database Accession No. Q9UDW7 (2000).

* cited by examiner

Fig. 1A

```
  1  CACTCACACACCTACGGACACACGCTACTCTGGGAGGTGATTTGCGACTTAGCCAGGCCC    60

61  CCAAAGCTGGGCTCCTGTAGGGAGAAAGTCTGCCCAGGTCCACATCCAAGCCTTCATCGT   120

121  TTGTCCTCCGGGTTCTGGGATCCTGCTGGAAGAGGGGAGCTTCTGCAATGGGAGTTGCCA   180
  1                                                  M  G  V  A     5

181  CAACCCTGCAGCCCCCAACCACTTCCAAAACCTTGCAGAAGCAGCATCTAGAAGCAGTGG   240
  6   T  L  Q  P  P  T  T  S  K  T  L  Q  K  Q  H  L  E  A  V  G    25

241  GCGCCTACCAATATGTGCTCACTTTCCTCTTCATGGGCCCTTTCTTCTCCCTTCTTGTCT   300
 26   A  Y  Q  Y  V  L  T  F  L  F  M  G  P  F  F  S  L  L  V  F    45

301  TTGTCCTCCTCTTCACGTCACTCTGGCCCTTCTCTGTTTTTTACTTGGTGTGGCTCTATG   360
 46   V  L  L  F  T  S  L  W  P  F  S  V  F  Y  L  V  W  L  Y  V    65

361  TGGACTGGGACACACCCAACCAAGGTGGAAGGCGTTCGGAGTGGATAAGGAACCGGGCAA   420
 66   W  D  W  D  T  P  N  Q  G  G  R  R  S  E  W  I  R  N  R  A  I  85

421  TTTGGAGACAACTAAGGGATTATTATCCTGTCAAGCTGGTGAAAACAGCAGAGCTGCCCC   480
 86   W  R  Q  L  R  D  Y  Y  P  V  K  L  V  K  T  A  E  L  P  P   105

481  CGGATCGGAACTACGTGCTGGGCGCCCACCCTCATGGGATCATGTGTACAGGCTTCCTCT   540
106   D  R  N  Y  V  L  G  A  H  P  H  G  I  M  C  T  G  F  L  C   125

541  GTAATTTCTCCACCGAGAGCAATGGCTTCTCCCAGCTCTTCCCGGGGCTCCGGCCCTGGT   600
126   N  F  S  T  E  S  N  G  F  S  Q  L  F  P  G  L  R  P  W  L   145

601  TAGCCGTGCTGGCTGGCCTCTTCTACCTCCCGGTCTATCGCGACTACATCATGTCCTTTG   660
146   A  V  L  A  G  L  F  Y  L  P  V  Y  R  D  Y  I  M  S  F  G   165

661  GACTCTGTCCGGTGAGCCGCCAGAGCCTGGACTTCATCCTGTCCCAGCCCCAGCTCGGGC   720
166   L  C  P  V  S  R  Q  S  L  D  F  I  L  S  Q  P  Q  L  G  Q   185

721  AGGCCGTGGTCATCATGGTGGGGGGTGCGCACGAGGCCCTGTATTCAGTCCCCGGGGAGC   780
186   A  V  V  I  M  V  G  G  A  H  E  A  L  Y  S  V  P  G  E  H   205

781  ACTGCCTTACGCTCCAGAAGCGCAAAGGCTTCGTGCGCCTGGCGCTGAGGCACGGGGCGT   840
206   C  L  T  L  Q  K  R  K  G  F  V  R  L  A  L  R  H  G  A  S   225

841  CCCTGGTGCCCGTGTACTCCTTTGGGGAGAATGACATCTTTAGACTTAAGGCTTTTGCCA   900
226   L  V  P  V  Y  S  F  G  E  N  D  I  F  R  L  K  A  F  A  T   245

901  CAGGCTCCTGGCAGCATTGGTGCCAGCTCACCTTCAAGAAGCTCATGGGCTTCTCTCCTT   960
246   G  S  W  Q  H  W  C  Q  L  T  F  K  K  L  M  G  F  S  P  C   265

961  GCATCTTCTGGGGTCGCGGTCTCTTCTCAGCCACCTCCTGGGGCCTGCTGCCCTTTGCTG  1020
266   I  F  W  G  R  G  L  F  S  A  T  S  W  G  L  L  P  F  A  V   285
```

Fig. 1B

```
1021  TGCCCATCACCACTGTGGTGGGCCGCCCCATCCCCGTCCCCCAGCGCCTCCACCCCACCG  1080
 286    P  I  T  T  V  V  G  R  P  I  P  V  P  Q  R  L  H  P  T  E   305

1081  AGGAGGAAGTCAATCACTATCACGCCCTCTACATGACGGCCCTGGAGCAGCTCTTCGAGG  1140
 306    E  E  V  N  H  Y  H  A  L  Y  M  T  A  L  E  Q  L  F  E  E   325

1141  AGCACAAGGAAAGCTGTGGGGTCCCCGCTTCCACCTGCCTCACCTTCATCTAGGCCTGGC  1200
 326    H  K  E  S  C  G  V  P  A  S  T  C  L  T  F  I              341

1201  CGCGGCCTTTCGCTGAGCCCCTGAGCCCAAGGCACTGAGACCTCCACCCACTGTGGACTC  1260

1261  CATGCCTCCAATAAAAGGTAGTTCTGGGCCCAGCGCAGTGCCTCGTGCCTGTGATCCCAG  1320

1321  CACTTTGGGAGGCCAGGGTGGGAGGATCGTTTGAGCCCAGGAGTTGAAGACCAGCCTGGG  1380

1381  CAACACAGTGAGACTTCATTTCTACAAAAAAAAAAAAAAA  1420
```

Fig.2: Alignment of Predicted Human
MGAT3 with its Homologues

```
                  1                                                50
MGAT3     (1)     ---------------------------------------------MGV
MGAT1     (1)     -------------------------------------------------
DGAT2     (1)     MKTLIAAYSGVLRGERQAEADRSQRSHGGPALSREGSGRWGTGSSILSAL 51                                               100
MGAT3     (4)     ATTLQPPTTSKTLQKQH LEAVGAY QYVLTFL FMGPFFSLLVFVLLF TSLW
MGAT1     (1)     -MKVEFAP LN-IQLARR LQTVAVL QWVLSFL TGPMSIGIT VMLIIHN-YL
DGAT2     (51)    QDLFSVTW LNRSKVEKQ LQVISVL QWVLSFL VLGVACSAILMYIFC TDCW 101                                              150
MGAT3     (54)    PFSVFYLVWLYVDWDTPNQ GGRRS EWIRNRAIWRQLRDYPVKLVKTAEL
MGAT1     (48)    FLYIPYLMWLYFDWHTPER GGRRS SWIKNWTLWKHFKDYFPIHLIKTQDL
DGAT2     (101)   LIAVLYFTWLVFDWNTPKK GGRRS QWVRNWAVWRYFRDYFPIQLVKTHNL 151                                              200
MGAT3     (104)   PPDRNYVLGAHPHGIMCTGFLCNFSTESNGFSQLFPGLRPWLAVLAGLFY
MGAT1     (98)    DPSHNYIFGFHPHGIMAVGAFGNFSVNYSDFKDLFPGFTSYLHVLPLWFW
DGAT2     (151)   LTTRNYIFGYHPHGIMGLGAFCNFSTEATEVSKKFPGIRPYLATLAGNFR 201                                              250
MGAT3     (154)   LPVYRDYIMSFGLCPVSRQSLDFILSQPQLGQAVVIMVGGAHEALYSVPG
MGAT1     (148)   CPVFREYVMSVGLVSVSKKSVSYMVSKEGGGNISVIVLGGAKESLDAHPG
DGAT2     (201)   MPVLREYLMSGGICPVSRDTIDYLLSKNGSGNAIIIVWGGAAESLSSMPG 251                                              300
MGAT3     (204)   EHCLTLQKRKGFVRLALRHGASLVPVYSFGENDIFRLKAFATGSWQHWCQ
MGAT1     (198)   KFTLFIRQRKGFVKIALTHGASLVPVVSFGENELFKQTDNPEGSWIRTVQ
DGAT2     (251)   KNAVTLRNRKGFVKLALRHGADLVPIYSFGENEVYKQVIFEEGSWGRWVQ 301                                              350
MGAT3     (254)   LTFKKLMGFSPCIFWGRGLFSATSWGLLPFAVPITTVVGRPIPVPQRLHP
MGAT1     (248)   NKLQKIMGFALPLFHARGVFQYN-FGLMTYRKAIHTVVGRPIPVRQTLNP
DGAT2     (301)   KKFQKYIGFAPCIFHGRGLFSSDTWGLVPYSKPITTVVGEPITIPKLEHP 351                       388
MGAT3     (304)   TEEEVNHYHALYMTALEQLFEEHKESCGVPASTCLTFI
MGAT1     (297)   TQEQTEELHQTYMEELRKLFEEHKGKYGIPEHETLVLK
DGAT2     (351)   TQQDIDLYHTMYMEALVKLFDKHKTKFGLPETEVLEVN
```

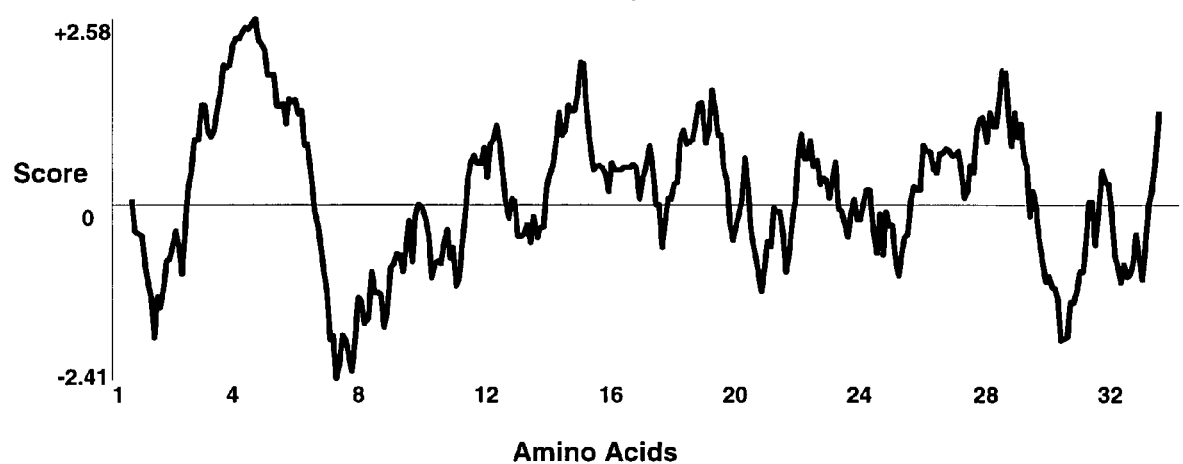
Fig.3 Hydrophobicity Analysis of MGAT3

Fig. 4 Expression of Recombinant MGAT3
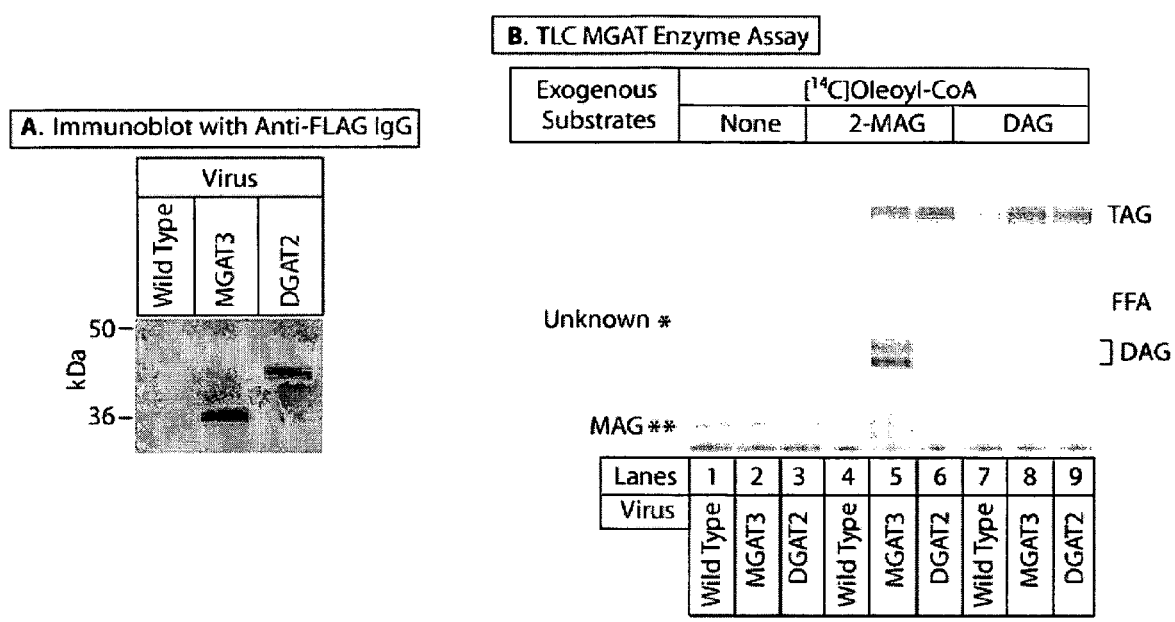

Fig.5 Time Course of Expression
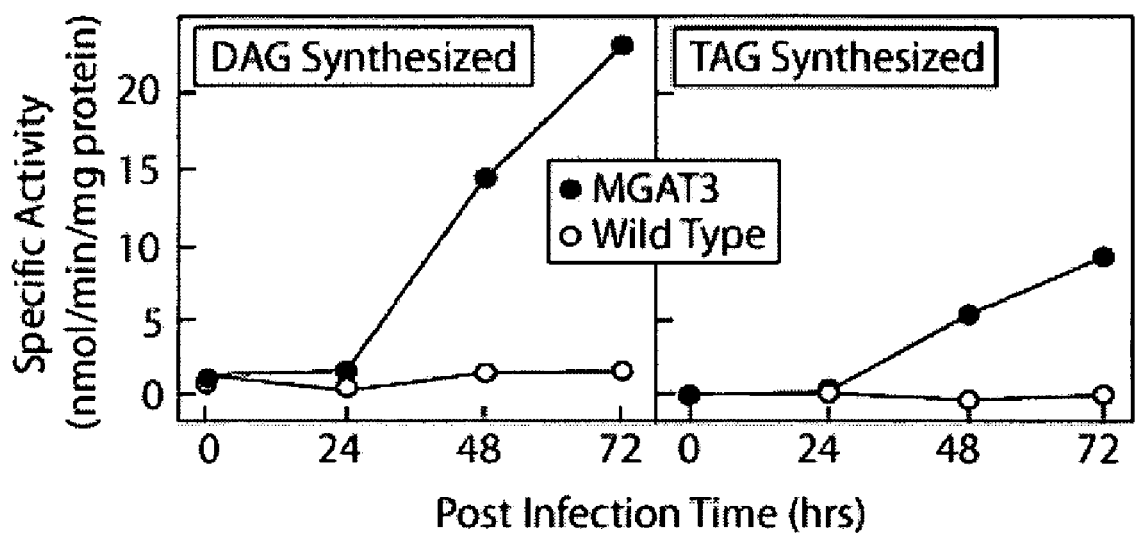

Fig.6 Substrate Concentration Curve
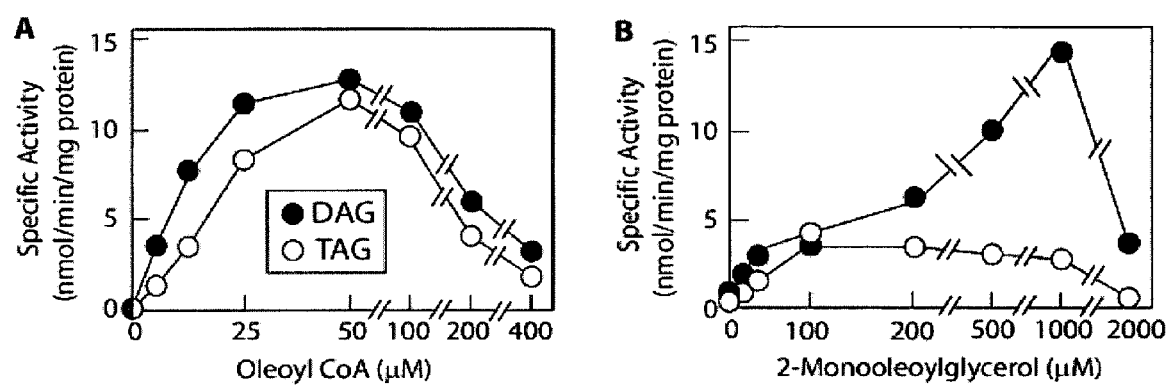

Fig. 7 Substrate Specificity
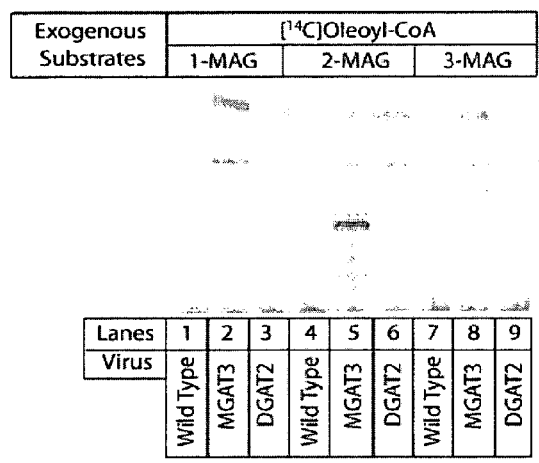
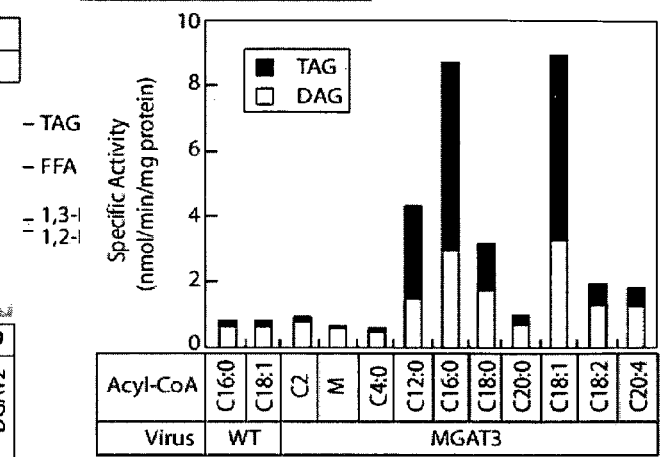

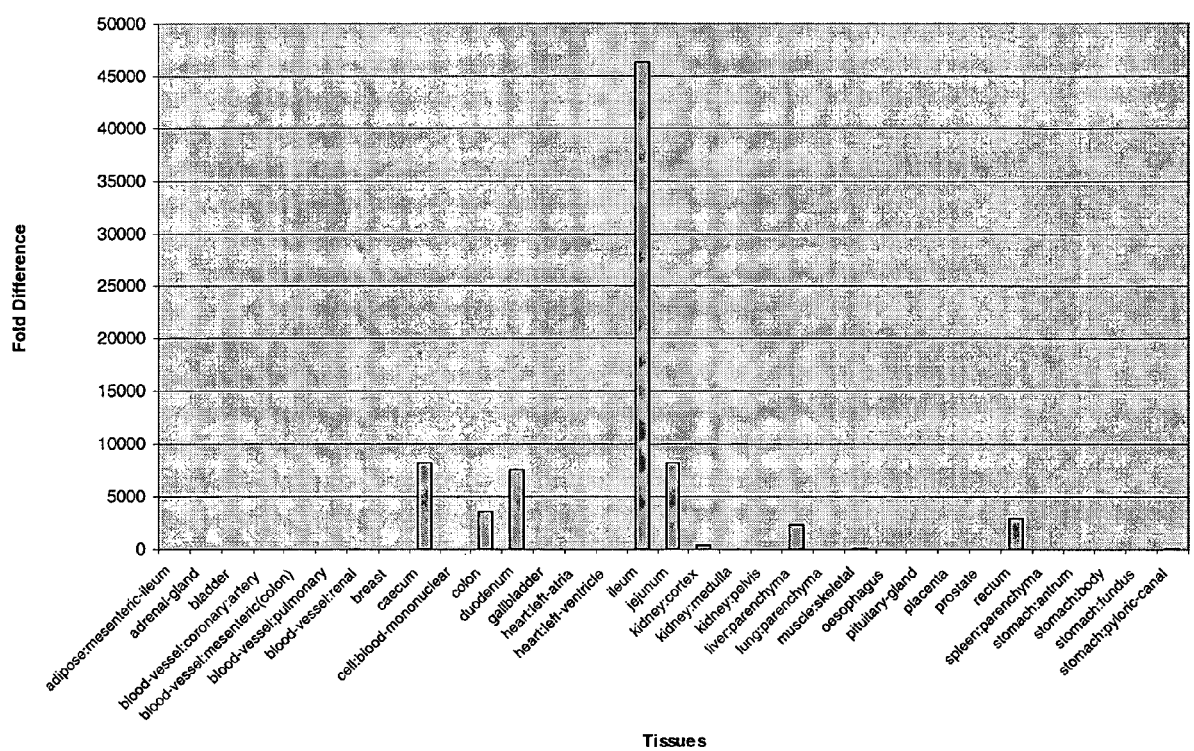
Fig.8 Relative Expression of MGAT3 in Normal Tissues

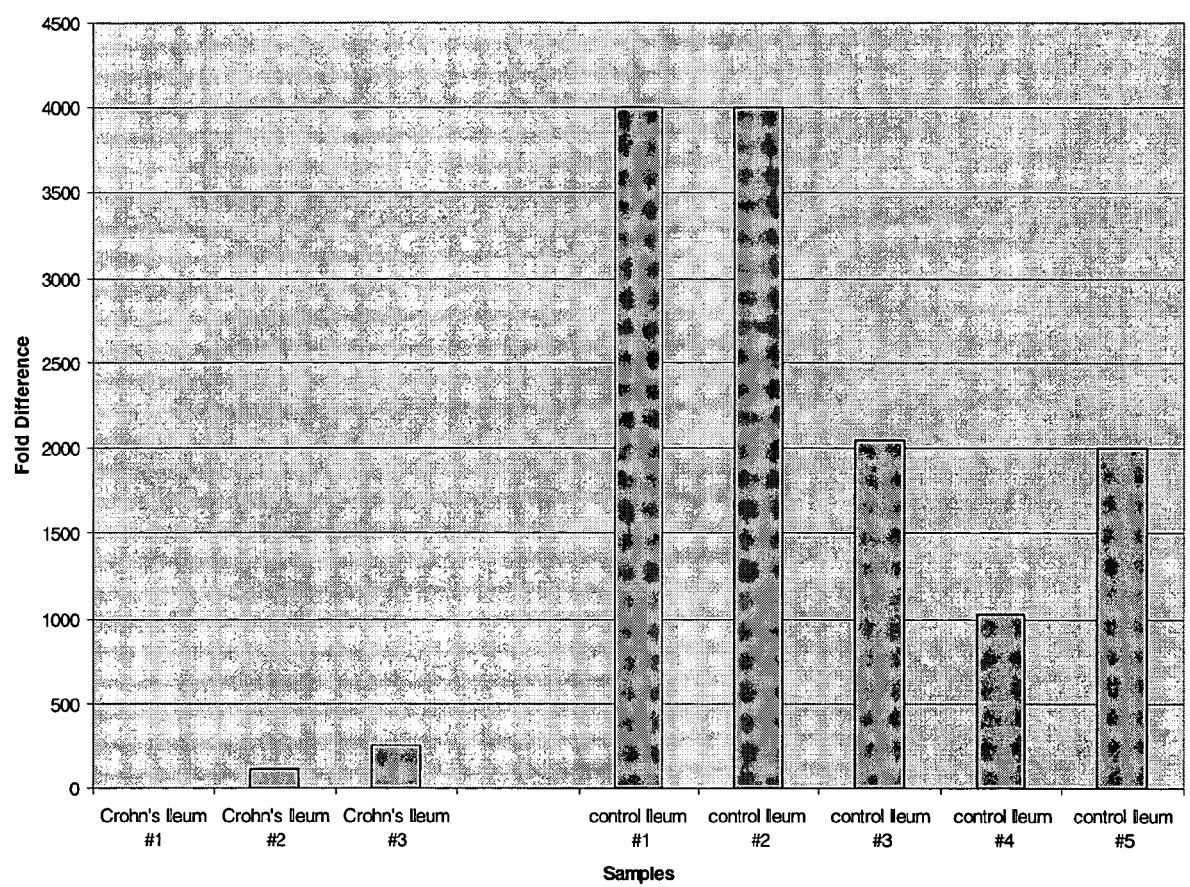
Fig.9 Relative expression of MGAT3 in Crohn's and control Ileum

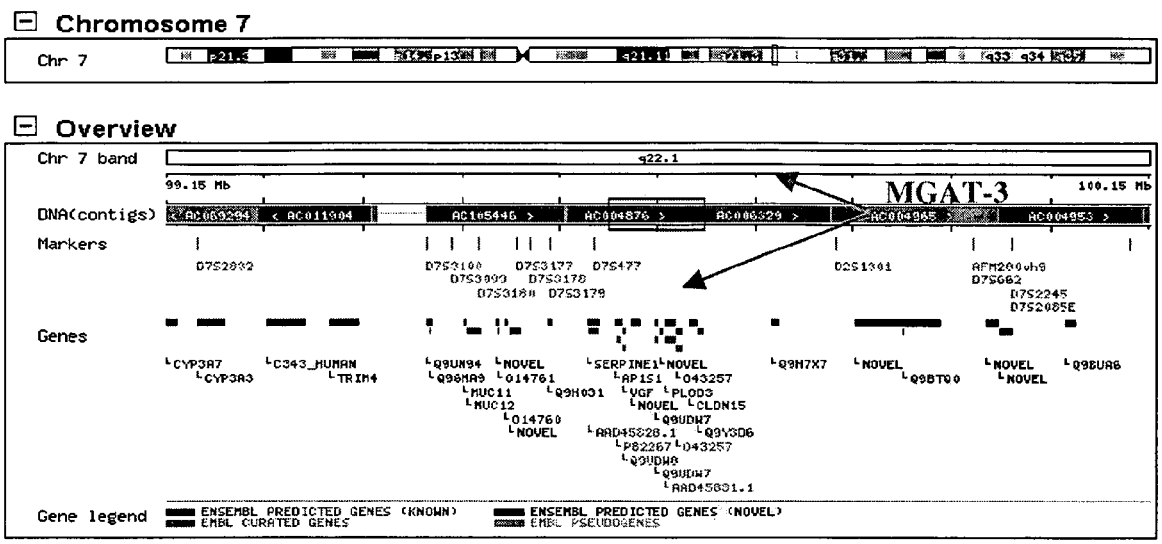
Fig.10 MGAT3 Gene is Located on Chromosome 7q22.1

SEQUENCE LISTING

<160> NUMBER OF SEQ ID NOS: 25

<210> SEQ ID NO 1
<211> LENGTH: 1420
<212> TYPE: DNA
<213> ORGANISM: Homo Sapiens

<400> SEQUENCE: 1

```
cactcacaca cctacggaca cacgctactc tgggaggtga tttgcgactt agccaggccc      60
ccaaagctgg gctcctgtag ggagaaagtc tgcccaggtc cacatccaag ccttcatcgt     120
ttgtcctccg ggttctggga tcctgctgga agaggggagc ttctgcaatg ggagttgcca     180
caaccctgca gcccccaacc acttccaaaa ccttgcagaa gcagcatcta gaagcagtgg     240
gcgcctacca atatgtgctc actttcctct tcatgggccc tttcttctcc cttcttgtct     300
ttgtcctcct cttcacgtca ctctggccct tctctgtttt ttacttggtg tggctctatg     360
tggactggga cacacccaac caaggtggaa ggcgttcgga gtggataagg aaccgggcaa     420
tttggagaca actaagggat tattatcctg tcaagctggt gaaaacagca gagctgcccc     480
cggatcggaa ctacgtgctg ggcgcccacc ctcatgggat catgtgtaca ggcttcctct     540
gtaatttctc caccgagagc aatggcttct cccagctctt cccggggctc cggccctggt     600
tagccgtgct ggctggcctc ttctacctcc cggtctatcg cgactacatc atgtccttg     660 gactctgtcc ggtgagccgc cagagcctgg acttcatcct gtcccagccc cagctcgggc     720
aggccgtggt catcatggtg gggggtgcgc acgaggccct gtattcagtc cccggggagc     780
actgccttac gctccagaag cgcaaaggct tcgtgcgcct ggcgctgagg cacggggcgt     840
ccctggtgcc cgtgtactcc tttggggaga atgacatctt tagacttaag gcttttgcca     900
caggctcctg gcagcattgg tgccagctca ccttcaagaa gctcatgggc ttctctcctt     960
```

```
gcatcttctg gggtcgcggt ctcttctcag ccacctcctg gggcctgctg cccttttgctg    1020 tgcccatcac cactgtggtg ggccgcccca tccccgtccc ccagcgcctc caccccaccg     1080
aggaggaagt caatcactat cacgccctct acatgacggc cctggagcag ctcttcgagg    1140
agcacaagga aagctgtggg gtccccgctt ccacctgcct caccttcatc taggcctggc    1200
cgcggccttt cgctgagccc ctgagcccaa ggcactgaga cctccaccca ctgtggactc    1260
catgcctcca ataaaaggta gttctgggcc cagcgcagtg cctcgtgcct gtgatcccag    1320
cactttggga ggccagggtg ggaggatcgt ttgagcccag gagttgaaga ccagcctggg    1380
caacacagtg agacttcatt tctacaaaaa aaaaaaaaaa                          1420
```

<210> SEQ ID NO 2
<211> LENGTH: 341
<212> TYPE: PRT
<213> ORGANISM: Homo Sapiens

<400> SEQUENCE: 2

```
Met Gly Val Ala Thr Thr Leu Gln Pro Pro Thr Thr Ser Lys Thr Leu
1               5                   10                  15

Gln Lys Gln His Leu Glu Ala Val Gly Ala Tyr Gln Tyr Val Leu Thr
            20                  25                  30

Phe Leu Phe Met Gly Pro Phe Ser Leu Leu Val Phe Val Leu Leu
        35                  40                  45

Phe Thr Ser Leu Trp Pro Phe Ser Val Phe Tyr Leu Val Trp Leu Tyr
    50                  55                  60

Val Asp Trp Asp Thr Pro Asn Gln Gly Gly Arg Arg Ser Glu Trp Ile
65                  70                  75                  80

Arg Asn Arg Ala Ile Trp Arg Gln Leu Arg Asp Tyr Tyr Pro Val Lys
                85                  90                  95

Leu Val Lys Thr Ala Glu Leu Pro Pro Asp Arg Asn Tyr Val Leu Gly
            100                 105                 110

Ala His Pro His Gly Ile Met Cys Thr Gly Phe Leu Cys Asn Phe Ser
        115                 120                 125

Thr Glu Ser Asn Gly Phe Ser Gln Leu Phe Pro Gly Leu Arg Pro Trp
    130                 135                 140

Leu Ala Val Leu Ala Gly Leu Phe Tyr Leu Pro Val Tyr Arg Asp Tyr
145                 150                 155                 160

Ile Met Ser Phe Gly Leu Cys Pro Val Ser Arg Gln Ser Leu Asp Phe
                165                 170                 175

Ile Leu Ser Gln Pro Gln Leu Gly Gln Ala Val Val Ile Met Val Gly
            180                 185                 190

Gly Ala His Glu Ala Leu Tyr Ser Val Pro Gly Glu His Cys Leu Thr
        195                 200                 205

Leu Gln Lys Arg Lys Gly Phe Val Arg Leu Ala Leu Arg His Gly Ala
    210                 215                 220

Ser Leu Val Pro Val Tyr Ser Phe Gly Glu Asn Asp Ile Phe Arg Leu
225                 230                 235                 240

Lys Ala Phe Ala Thr Gly Ser Trp Gln His Trp Cys Gln Leu Thr Phe
                245                 250                 255

Lys Lys Leu Met Gly Phe Ser Pro Cys Ile Phe Trp Gly Arg Gly Leu
            260                 265                 270

Phe Ser Ala Thr Ser Trp Gly Leu Leu Pro Phe Ala Val Pro Ile Thr
        275                 280                 285
```

```
Thr Val Val Gly Arg Pro Ile Pro Val Pro Gln Arg Leu His Pro Thr
    290                 295                 300

Glu Glu Glu Val Asn His Tyr His Ala Leu Tyr Met Thr Ala Leu Glu
305                 310                 315                 320

Gln Leu Phe Glu Glu His Lys Glu Ser Cys Gly Val Pro Ala Ser Thr
                325                 330                 335

Cys Leu Thr Phe Ile
            340

<210> SEQ ID NO 3
<211> LENGTH: 14
<212> TYPE: PRT
<213> ORGANISM: Homo Sapiens

<400> SEQUENCE: 3

Thr Gly Phe Leu Cys Asn Phe Ser Thr Glu Ser Asn Gly Phe
1               5                   10

<210> SEQ ID NO 4
<211> LENGTH: 14
<212> TYPE: PRT
<213> ORGANISM: Homo Sapiens

<400> SEQUENCE: 4

Leu Val Pro Val Tyr Ser Phe Gly Glu Asn Asp Ile Phe Arg
1               5                   10

<210> SEQ ID NO 5
<211> LENGTH: 14
<212> TYPE: PRT
<213> ORGANISM: Homo Sapiens

<400> SEQUENCE: 5

Gln Arg Leu His Pro Thr Glu Glu Glu Val Asn His Tyr His
1               5                   10

<210> SEQ ID NO 6
<211> LENGTH: 14
<212> TYPE: PRT
<213> ORGANISM: Homo Sapiens

<400> SEQUENCE: 6

His Ala Leu Tyr Met Thr Ala Leu Glu Gln Leu Phe Glu Glu
1               5                   10

<210> SEQ ID NO 7
<211> LENGTH: 12
<212> TYPE: PRT
<213> ORGANISM: Homo Sapiens

<400> SEQUENCE: 7

Met Gly Val Ala Thr Thr Leu Gln Pro Pro Thr Thr
1               5                   10

<210> SEQ ID NO 8
<211> LENGTH: 16
<212> TYPE: PRT
<213> ORGANISM: Homo Sapiens

<400> SEQUENCE: 8

Asp Thr Pro Asn Gln Gly Gly Arg Arg Ser Glu Trp Ile Arg Asn Arg
1               5                   10                  15
```

<210> SEQ ID NO 9
<211> LENGTH: 16
<212> TYPE: PRT
<213> ORGANISM: Homo Sapiens

<400> SEQUENCE: 9

Gly Ala His Pro His Gly Ile Met Cys Thr Gly Phe Leu Cys Asn Phe
1               5                   10                  15

<210> SEQ ID NO 10
<211> LENGTH: 16
<212> TYPE: PRT
<213> ORGANISM: Homo Sapiens

<400> SEQUENCE: 10

Val Ile Met Val Gly Gly Ala His Glu Ala Leu Tyr Ser Val Pro Gly
1               5                   10                  15

<210> SEQ ID NO 11
<211> LENGTH: 16
<212> TYPE: PRT
<213> ORGANISM: Homo Sapiens

<400> SEQUENCE: 11

Ile Phe Trp Gly Arg Gly Leu Phe Ser Ala Thr Ser Trp Gly Leu Leu
1               5                   10                  15

<210> SEQ ID NO 12
<211> LENGTH: 16
<212> TYPE: PRT
<213> ORGANISM: Homo Sapiens

<400> SEQUENCE: 12

His Lys Glu Ser Cys Gly Val Pro Ala Ser Thr Cys Leu Thr Phe Ile
1               5                   10                  15

<210> SEQ ID NO 13
<211> LENGTH: 13
<212> TYPE: PRT
<213> ORGANISM: Homo Sapiens

<400> SEQUENCE: 13

Leu Gln Pro Pro Thr Thr Ser Lys Thr Leu Gln Lys Gln
1               5                   10

<210> SEQ ID NO 14
<211> LENGTH: 13
<212> TYPE: PRT
<213> ORGANISM: Homo Sapiens

<400> SEQUENCE: 14

His Trp Cys Gln Leu Thr Phe Lys Lys Leu Met Gly Phe
1               5                   10

<210> SEQ ID NO 15
<211> LENGTH: 80
<212> TYPE: DNA
<213> ORGANISM: Homo Sapiens

<400> SEQUENCE: 15
gcccactgct tctagatgct gcttctgcaa ggttttggaa gtggttgggg gctgcagggt    60
tgtggcaact cccattgcag                                                80

<210> SEQ ID NO 16

```
<211> LENGTH: 20
<212> TYPE: DNA
<213> ORGANISM: Homo Sapiens

<400> SEQUENCE: 16
gagcttctgc aatgggagtt                                              20

<210> SEQ ID NO 17
<211> LENGTH: 20
<212> TYPE: DNA
<213> ORGANISM: Homo Sapiens

<400> SEQUENCE: 17
tgagcacata ttggtaggcg                                              20

<210> SEQ ID NO 18
<211> LENGTH: 23
<212> TYPE: DNA
<213> ORGANISM: Homo Sapiens

<400> SEQUENCE: 18
actctggccc ttctctgttt ttt                                          23

<210> SEQ ID NO 19
<211> LENGTH: 19
<212> TYPE: DNA
<213> ORGANISM: Homo Sapiens

<400> SEQUENCE: 19
aacgccttcc accttggtt                                               19

<210> SEQ ID NO 20
<211> LENGTH: 27
<212> TYPE: DNA
<213> ORGANISM: Homo Sapiens

<400> SEQUENCE: 20
tcccagtcca catagagcca caccaag                                      27

<210> SEQ ID NO 21
<211> LENGTH: 10
<212> TYPE: PRT
<213> ORGANISM: Homo Sapiens

<400> SEQUENCE: 21

Met Gly Asp Tyr Lys Asp Asp Asp Asp Gly
1               5                   10

<210> SEQ ID NO 22
<211> LENGTH: 388
<212> TYPE: PRT
<213> ORGANISM: Homo Sapiens

<400> SEQUENCE: 22

Met Lys Thr Leu Ile Ala Ala Tyr Ser Gly Val Leu Arg Gly Glu Arg
1               5                   10                  15

Gln Ala Glu Ala Asp Arg Ser Gln Arg Ser His Gly Gly Pro Ala Leu
            20                  25                  30

Ser Arg Glu Gly Ser Gly Arg Trp Gly Thr Gly Ser Ser Ile Leu Ser
        35                  40                  45

Ala Leu Gln Asp Leu Phe Ser Val Thr Trp Leu Asn Arg Ser Lys Val
    50                  55                  60
```

```
Glu Lys Gln Leu Gln Val Ile Ser Val Leu Gln Trp Val Leu Ser Phe
 65                  70                  75                  80

Leu Val Leu Gly Val Ala Cys Ser Ala Ile Leu Met Tyr Ile Phe Cys
                 85                  90                  95

Thr Asp Cys Trp Leu Ile Ala Val Leu Tyr Phe Thr Trp Leu Val Phe
            100                 105                 110

Asp Trp Asn Thr Pro Lys Lys Gly Gly Arg Arg Ser Gln Trp Val Arg
            115                 120                 125

Asn Trp Ala Val Trp Arg Tyr Phe Arg Asp Tyr Phe Pro Ile Gln Leu
        130                 135                 140

Val Lys Thr His Asn Leu Leu Thr Thr Arg Asn Tyr Ile Phe Gly Tyr
145                 150                 155                 160

His Pro His Gly Ile Met Gly Leu Gly Ala Phe Cys Asn Phe Ser Thr
                165                 170                 175

Glu Ala Thr Glu Val Ser Lys Lys Phe Pro Gly Ile Arg Pro Tyr Leu
            180                 185                 190

Ala Thr Leu Ala Gly Asn Phe Arg Met Pro Val Leu Arg Glu Tyr Leu
        195                 200                 205

Met Ser Gly Gly Ile Cys Pro Val Ser Arg Asp Thr Ile Asp Tyr Leu
    210                 215                 220

Leu Ser Lys Asn Gly Ser Gly Asn Ala Ile Ile Ile Val Val Gly Gly
225                 230                 235                 240

Ala Ala Glu Ser Leu Ser Ser Met Pro Gly Lys Asn Ala Val Thr Leu
                245                 250                 255

Arg Asn Arg Lys Gly Phe Val Lys Leu Ala Leu Arg His Gly Ala Asp
            260                 265                 270

Leu Val Pro Ile Tyr Ser Phe Gly Glu Asn Glu Val Tyr Lys Gln Val
        275                 280                 285

Ile Phe Glu Glu Gly Ser Trp Gly Arg Trp Val Gln Lys Lys Phe Gln
    290                 295                 300

Lys Tyr Ile Gly Phe Ala Pro Cys Ile Phe His Gly Arg Gly Leu Phe
305                 310                 315                 320

Ser Ser Asp Thr Trp Gly Leu Val Pro Tyr Ser Lys Pro Ile Thr Thr
                325                 330                 335

Val Val Gly Glu Pro Ile Thr Ile Pro Lys Leu Glu His Pro Thr Gln
            340                 345                 350

Gln Asp Ile Asp Leu Tyr His Thr Met Tyr Met Glu Ala Leu Val Lys
        355                 360                 365

Leu Phe Asp Lys His Lys Thr Lys Phe Gly Leu Pro Glu Thr Glu Val
    370                 375                 380

Leu Glu Val Asn
385

<210> SEQ ID NO 23
<211> LENGTH: 334
<212> TYPE: PRT
<213> ORGANISM: Homo Sapiens

<400> SEQUENCE: 23

Met Lys Val Glu Phe Ala Pro Leu Asn Ile Gln Leu Ala Arg Arg Leu
 1                   5                  10                  15

Gln Thr Val Ala Val Leu Gln Trp Val Leu Ser Phe Leu Thr Gly Pro
                 20                  25                  30

Met Ser Ile Gly Ile Thr Val Met Leu Ile Ile His Asn Tyr Leu Phe
             35                  40                  45
```

```
Leu Tyr Ile Pro Tyr Leu Met Trp Leu Tyr Phe Asp Trp His Thr Pro
    50                  55                  60

Glu Arg Gly Arg Arg Ser Ser Trp Ile Lys Asn Trp Thr Leu Trp
65                  70                  75                  80

Lys His Phe Lys Asp Tyr Phe Pro Ile His Leu Ile Lys Thr Gln Asp
                85                  90                  95

Leu Asp Pro Ser His Asn Tyr Ile Phe Gly Phe His Pro His Gly Ile
            100                 105                 110

Met Ala Val Gly Ala Phe Gly Asn Phe Ser Val Asn Tyr Ser Asp Phe
        115                 120                 125

Lys Asp Leu Phe Pro Gly Phe Thr Ser Tyr Leu His Val Leu Pro Leu
    130                 135                 140

Trp Phe Trp Cys Pro Val Phe Arg Glu Tyr Val Met Ser Val Gly Leu
145                 150                 155                 160

Val Ser Val Ser Lys Lys Ser Val Ser Tyr Met Val Ser Lys Glu Gly
                165                 170                 175

Gly Gly Asn Ile Ser Val Ile Val Leu Gly Gly Ala Lys Glu Ser Leu
            180                 185                 190

Asp Ala His Pro Gly Lys Phe Thr Leu Phe Ile Arg Gln Arg Lys Gly
        195                 200                 205

Phe Val Lys Ile Ala Leu Thr His Gly Ala Ser Leu Val Pro Val Val
    210                 215                 220

Ser Phe Gly Glu Asn Glu Leu Phe Lys Gln Thr Asp Asn Pro Glu Gly
225                 230                 235                 240

Ser Trp Ile Arg Thr Val Gln Asn Lys Leu Gln Lys Ile Met Gly Phe
                245                 250                 255

Ala Leu Pro Leu Phe His Ala Arg Gly Val Phe Gln Tyr Asn Phe Gly
            260                 265                 270

Leu Met Thr Tyr Arg Lys Ala Ile His Thr Val Val Gly Arg Pro Ile
        275                 280                 285

Pro Val Arg Gln Thr Leu Asn Pro Thr Gln Glu Gln Ile Glu Glu Leu
    290                 295                 300

His Gln Thr Tyr Met Glu Glu Leu Arg Lys Leu Phe Glu Glu His Lys
305                 310                 315                 320

Gly Lys Tyr Gly Ile Pro Glu His Glu Thr Leu Val Leu Lys
                325                 330

<210> SEQ ID NO 24
<211> LENGTH: 8
<212> TYPE: PRT
<213> ORGANISM: Homo Sapiens

<400> SEQUENCE: 24

Asp Tyr Lys Asp Asp Asp Asp Lys
1               5

<210> SEQ ID NO 25
<211> LENGTH: 14
<212> TYPE: PRT
<213> ORGANISM: Homo Sapiens

<400> SEQUENCE: 25

Asp Thr Pro Asn Gln Gly Gly Arg Arg Ser Glu Trp Ile Arg
1               5                   10
```

US 7,259,002 B2

POLYNUCLEOTIDE ENCODING A NOVEL ACYL COENZYME A, MONOACYLGLYCEROL ACYLTRANSFERASE-3 (MGAT3), AND USES THEREOF

This application claims the benefit of provisional U.S. Application Ser. No. 60/441,567, filed Jan. 21, 2003, which is incorporated herein by reference in its entirety.

FIELD OF THE INVENTION

The present invention provides novel polynucleotides encoding monoacylglycerol acyltransferase-3 ("MGAT3") polypeptides, fragments and homologues thereof. Also provided are vectors, host cells, antibodies, and recombinant and synthetic methods for producing said polypeptides. The invention further relates to diagnostic and therapeutic methods for applying these novel MGAT3 polypeptides to the diagnosis, treatment, and/or prevention of various diseases and/or disorders related to these polypeptides, particularly for the treatment of obesity. The invention further relates to screening methods for identifying agonists and antagonists of the polynucleotides and polypeptides of the present invention.

BACKGROUND OF RELATED TECHNOLOGY

Triacylglycerol (TAG), an important molecule for eukaryotic fuel storage, is synthesized by two major pathways, the glycerol 3-phosphate pathway and the monacylglycerol pathway. The glycerol 3-phosphate pathway is present in all tissues whereas the monoacylglycerol pathway is restricted to the enterocytes of the small intestine (Bell, R. M. and R. A. Coleman, *Annu. Rev. Biochem.* (1980). 49:459-87). The monoacylglyerol pathway is believed to be critical for the packaging of dietary fat into chylomicron lipoprotein particles (Levy, E., *Can. J. Physiol. Pharmacol.* (1992) 70(4): 413-9).

Acyl coenzyme A:monoacylglycerol acyltransferase ("MGAT") (EC 2.3.1.22) is an enzyme best known for its role in initiating the first step for the monoacylglycerol pathway (Lehner, R. and A. Kuksis, *Prog. Lipid Res.* (1996) 35(2):169-201). In order for insoluble dietary fat such as TAG to be absorbed by the intestine, dietary fat molecules must first be digested by pancreatic lipase into soluble free fatty acids and 2-monoacylglycerol. These products are quickly absorbed into enterocytes, within minutes of their appearance in the lumen of the small intestine, MGAT uses these molecules as substrates to form diacylglycerol (DAG). DAG is further acylated by diacylglycerol acyltransferase (DGAT) to re-form TAG. The newly formed TAG molecules are then packaged with other complex lipids such as cholesterol ester, phospholipids and small amount of protein to form round lipoprotein particles called chylomicrons. Chylomicrons, 90% of which are comprised of TAG, are quickly secreted into the lymph where they served as energy supplies for the body (Lehner, R. and A. Kuksis, supra).

Similar to other neutral lipid synthesis proteins, MGAT is an intrinsic membrane protein which to date has not been purified to homogeneity from any sources. The molecular identity of the gene encoding the intestinal MGAT has been elusive. The first cDNA clone shown to possess MGAT enzyme activity, designated MGAT1, was identified by Yen et al. (Yen, C. L., et al., *Proc. Natl. Acad. Sci. USA* (2002) 99(13):8512-7). However, MGAT1 is expressed in stomach, kidney, white adipose and brown adipose tissue, but not in small intestine. Therefore, MGAT1 cannot account for the high intestinal MGAT enzyme activity that is important for the physiology of fat absorption (Yen, C. L., et al., supra).

It is known that drugs that inhibit the absorption of dietary fat can be efficacious for obesity treatment (Zhi, J., et al. (1995) *J. Clin. Pharmacol.*, 35(11):1103-8; Lucas, K. H. and B. Kaplan-Machlis (2001) *Ann. Pharmacother.*, 35(3):314-28). However the mechanism for such drugs includes the inhibition of pancreatic lipase, which leads to the undesirable side effect of faecal leakage (Kolanowski, J. (1999) *Drug Saf.*, 20(2):119-31). An alternative approach is to allow for the digestion of fat to fatty acids in the gut, and then block the uptake or the packaging of fatty acids into chylomicron particles.

As intestinal MGAT is a critical enzyme for this pathway, there is a continuing need to identify genes responsible for MGAT intestinal enzyme activity, and therefore responsible for the absorption of dietary fat. The modulation of such genes will provide methods for the treatment of obesity. The present invention is directed to such a need.

BRIEF DESCRIPTION OF THE DRAWINGS

FIG. 1A-B shows the human MGAT3 cDNA sequence (SEQ ID NO:1) and the predicted amino acid sequence for human MGAT3 (SEQ ID NO:2). The predicted initiation codon and termination codon for the open frame is in italics. MGAT3 also includes a putative glycerol phospholipid domain from about amino acid F152 to amino acid R239, shown in bold.

FIG. 2 shows an alignment of the predicted human MGAT3 amino acid sequence (SEQ ID NO:2) with the human MGAT1 amino acid sequence (SEQ ID NO:23; GenBank Accession No. AF384163) and the human DGAT2 amino acid sequence (SEQ ID NO:22; GenBank Accession No. AF384161). The multiple sequence alignment was performed with ClustalW algorithm in VectorNTI program. Amino acids that are identical in all members are black boxed; similar residues are shaded.

FIG. 3 shows a hydrophobicity analysis of predicted human MGAT3. Analysis was performed using the Kyte and Doolittle algorithm (Kyte, J. and R. F. Doolittle (1982) *J. Mol. Biol.*, 157(1):105-32. The positive score is proportional to the degree of hydrophobicity.

FIG. 4 shows the expression of recombinant human MGAT3 in Sf9 insect cells. Sf9 cells were set up at 5×106 cells/flask in 25 cm2 flasks at Day 0. On Day 1, the cells were infected with either wild type baculovirus, MGAT3 or DGAT2 recombinant viruses respectively at MOI>3. On Day 3, cells were harvested and membrane fractions (100,000×g pellets) were prepared. A. Immunoblot with anti-FLAG IgG. Aliquots of 2 μg membrane proteins/lane were loaded on SDS-PAGE and blots were probed with anti-FLAG IgG at 2 μg/ml. B. TLC MGAT enzyme assay. Aliquots of 10 μg membrane proteins were subjected to MGAT enzyme assays at 37° C. for 6 min. For exogenous substrates, 200 μM sn-2-monooleoylglycerol and 50 μM [14C]oleoyl coenzyme A (20,000 dpm/nmol) were incubated with the membrane extracts. Lipid extracts were separated with TLC and the chromatogram was exposed to STORM Phospholmager for 12 hrs. DAG, diacylglycerol; TAG, triacylglycerol; FFA, free fatty acid; MAG, monoacylglycerol, denoted as nonspecific band **; Unknown, the other nonspecific band with unknown chemical nature, denoted as band *.

FIG. 5 shows the time course of recombinant human MGAT3 expression. Sf9 cells were setup and infected with wild type or recombinant MGAT3 viruses as in FIG. 4. Membrane extracts were prepared from the cells with various post infection times. Aliquots of membrane fractions were either subjected to A) immunoblot analysis with anti-FLAG IgG; or to B) TLC enzyme assays. For substrates, 200 μM sn-2-monooleoylglycerol and 50 μM [14C]oleoyl coenzyme A (20,000 dpm/nmol) were incubated with 10 μg membrane fractions for 6 min at 37° C. After TLC separation, the DAG and the TAG bands were cut from TLC sheets and subjected to scintillation counting. The activities were expressed as nmol/min/mg protein. Values were averages of duplicated determinations and the standard deviations were smaller than 10% of the mean.

FIG. 6 shows substrate concentration titration for recombinant human MGAT3. Sf9 cells were setup and infected with either wild type or recombinant MGAT3 viruses as in FIG. 4. After 2 days of infection, the cells were harvested, membrane fractions were prepared and aliquots of membranes were subjected to MGAT enzyme assays with various concentrations of substrates. For A, 200 μM sn-2-monooleoylglycerol and various amounts of [14C]oleoyl coenzyme A (20,000 dpm/nmol) and for B, 50 μM [14C]oleoyl coenzyme A (20,000 dpm/nmol) and various amounts of sn-2-monooleoylglycerol were incubated with 10 μg membrane fractions for 10 min at 37° C. Lipid bands corresponding to TAG and DAG were cut from TLC sheets and counted with scintillation counter. Activities were corrected values of recombinant membranes deducted by values of wild type membranes. Duplicated assays were conducted and the standard deviations were smaller than 10% of the mean.

FIG. 7 shows substrate specificities of MGAT3. Sf9 cells were setup and infected either with wild type, recombinant MGAT3 or with DGAT2 viruses as in FIG. 4. Aliquots of membrane fractions (10 μg) were subjected to MGAT assays to determine A) MAG stereoisomer specificity and B) preference of fatty acyl-CoAs. In A, 50 μM [14C]oleoyl coenzyme A (20,000 dpm/nmol) and 200 μM of sn-1-monooleoyglycerol (1-MAG), sn-2-monooleoyglycerol (2-MAG), or sn-3-monopalmitoylglycerol (3-MAG); and in B, 200 μM sn-2-[3H]monooleoylglycerol (20,000 dpm/nmol) and different acyl-CoAs at 50 μM were incubated with 10 μg membrane fractions at 37° C. for 10 min. C2, acetyl-CoA; M, malonyl-CoA; C4:0, butyryl-CoA; C12:0, lauroyl-CoA; C16:0, palmitoyl-CoA; C18:0, stearoyl-CoA; C20:0, arachidoyl-CoA; C18:1, oleoyl-CoA; C18:2, linoleoyl-CoA; C20:4, arachidonoyl-CoA.

FIG. 8 shows TaqMan™ Quantitative PCR analysis of MGAT3 in various normal human tissues.

FIG. 9 shows TaqMan™ Quantitative PCR analysis of MGAT3 expression in ileums of Crohn's disease patients as compared with normal human specimen.

FIG. 10 shows chromosomal localization of human MGAT3. The MGAT3 cDNA sequence (SEQ ID NO:1) was mapped to the human genome (NCBI human genome version 29) using Mega-Blast/Sim4 method in the Biotique Local Integration System (BLIS) program. The location of MGAT3 is indicated with red brackets.

SUMMARY OF THE INVENTION

The present invention is directed to a novel cDNA, designated monoacylglycerol acyltransferase-3 (hereinafter "MGAT3") which encodes an MGAT protein having the amino acid sequence shown in FIG. 1A-B (SEQ ID NO:2) or the amino acid sequence encoded by at least one MGAT3 cDNA clone, deposited as ATCC Deposit Numbers PTA-4454 and PTA-4803 on Jun. 12, 2002 and Nov. 14, 2002, respectively. MGAT3 has the polynucleotide sequence set forth in FIG. 1A-1B (SEQ ID NO:1) or the polynucleotide sequence of at least one MGAT3 cDNA clone, deposited as ATCC Deposit Numbers PTA-4454 and PTA-4803 on Jun. 12, 2002 and Nov. 14, 2002, respectively.

MGAT3 has been identified using bioinformatic methods and cloned using molecular techniques. MGAT3 fulfills the criteria as the MGAT that is responsible for the absorption of dietary fat. The expression profile of human MGAT3 is highly restricted to gastrointestinal tract. As prevention of fat absorption is one of the proven methods to cause weight loss, intestinal MGAT inhibition, therefore, provides an approach for anti-obesity treatment. MGAT3 is therefore an important target for the treatment of obesity and related disease states.

The present invention also includes recombinant vectors, which include the isolated nucleic acid molecules of the present invention, and to host cells containing the recombinant vectors, as well as to methods of making such vectors and host cells, in addition to their use in the production of MGAT protein or peptides using recombinant techniques. Synthetic methods for producing the polypeptides and polynucleotides of the present invention are provided. Also provided are diagnostic methods for detecting diseases, disorders, and/or conditions related to MGAT polypeptides and polynucleotides, and therapeutic methods for treating such diseases, disorders, and/or conditions. The invention further relates to screening methods for identifying binding partners of the polypeptides, particularly activators and inhibitors of the novel MGAT polypeptides of the present invention.

In one aspect, the present invention is directed to an isolated nucleic acid molecule consisting of a polynucleotide having the nucleotide sequence of SEQ ID NO:1.

In another aspect, the present invention is directed to an isolated nucleic acid molecule comprising a polynucleotide having the nucleotide sequence selected from the group consisting of: (a) a polynucleotide fragment of SEQ ID NO:1 or a polynucleotide fragment of a cDNA sequence included in one of ATCC Deposit Numbers PTA-4454 or PTA-4803, deposited on Jun. 12, 2002 and Nov. 14, 2002, respectively, which is hybridizable to SEQ ID NO:1; (b) a polynucleotide encoding a polypeptide fragment of SEQ ID NO:2 or a polypeptide fragment encoded by a cDNA sequence included in one of ATCC Deposit Numbers PTA-4454 or PTA-4803, deposited on Jun. 12, 2002 and Nov. 14, 2002, respectively, which is hybridizable to SEQ ID NO:1; (c) a polynucleotide encoding a polypeptide domain of SEQ ID NO:2 or a polypeptide domain encoded by a cDNA sequence included in one of ATCC Deposit Numbers PTA-4454 or PTA-4803, deposited on Jun. 12, 2002 and Nov. 14, 2002, respectively, which is hybridizable to SEQ ID NO:1; (d) a polynucleotide encoding a polypeptide epitope of SEQ ID NO:2 or a polypeptide epitope encoded by a cDNA sequence included in one of ATCC Deposit Numbers PTA-4454 or PTA-4803, deposited on Jun. 12, 2002 and Nov. 14, 2002, respectively, which is hybridizable to SEQ ID NO:1; (e) a polynucleotide which represents the complimentary sequence (antisense) of SEQ ID NO:1; and (f) a polynucleotide capable of hybridizing under stringent conditions to any one of the polynucleotides specified in (a)-(e), wherein said polynucleotide does not hybridize under stringent conditions to a nucleic acid molecule having a nucleotide sequence of only A residues or of only T residues.

In another aspect, the present invention is directed to any of the nucleic acid molecules described above, wherein the polynucleotide fragment consists of a nucleotide sequence encoding MGAT3.

In another aspect, the present invention is directed to a recombinant vector comprising any of the isolated nucleic acid molecule described above.

In another aspect, the present invention is directed to a recombinant host cell comprising any recombinant vector described above.

In another aspect, the present invention is directed to an isolated polypeptide comprising an amino acid sequence selected from the group consisting of: (a) a polypeptide fragment of SEQ ID NO:2 or an encoded sequence included in one of ATCC Deposit Numbers PTA-4454 or PTA-4803, deposited on Jun. 12, 2002 and Nov. 14, 2002, respectively; (b) a polypeptide domain of SEQ ID NO:2 or an encoded sequence included in one of ATCC Deposit Numbers PTA-4454 or PTA-4803, deposited on Jun. 12, 2002 and Nov. 14, 2002, respectively; (c) a polypeptide epitope of SEQ ID NO:2 or an encoded sequence included in one of ATCC Deposit Numbers PTA-4454 or PTA-4803, deposited on Jun. 12, 2002 and Nov. 14, 2002, respectively; and (d) a full length protein of SEQ ID NO:2 or an encoded sequence included in one of ATCC Deposit Numbers PTA-4454 or PTA-4803, deposited on Jun. 12, 2002 and Nov. 14, 2002, respectively.

In another aspect, the present invention is directed to an isolated polypeptide described above, wherein the full length protein comprises sequential amino acid deletions from either the C-terminus or the N-terminus.

In another aspect, the present invention is directed to an isolated antibody that binds specifically to an isolated polypeptide described above.

In another aspect, the present invention is directed to a recombinant host cell that expresses an isolated polypeptide described above.

In another aspect, the present invention is directed to a method of making an isolated polypeptide comprising: (a) culturing a recombinant host cell described above under conditions such that the polypeptide is expressed; and (b) recovering the polypeptide. The present invention also includes a polypeptide produced by such a method.

In another aspect, the present invention is directed to a method for preventing, treating, or ameliorating a medical condition, comprising the step of administering to a mammalian subject a therapeutically effective amount of a polypeptide described above, or a modulator thereof.

In another aspect, the present invention is directed to a method for treating obesity, comprising the step of administering to an obese mammalian subject a therapeutically effective amount of a polypeptide described above, or a modulator thereof.

In another aspect, the present invention is directed to a method of diagnosing a pathological condition or a susceptibility to a pathological condition in a subject comprising: (a) determining the presence or absence of a mutation in a polynucleotide described above; and (b) diagnosing a pathological condition or a susceptibility to a pathological condition based on the presence or absence of the mutation.

In another aspect, the present invention is directed to a method of diagnosing a pathological condition or a susceptibility to a pathological condition in a subject comprising: (a) determining the presence or amount of expression of a polypeptide described above in a biological sample; and (b) diagnosing a pathological condition or a susceptibility to a pathological condition based on the presence or amount of expression of the polypeptide.

In another aspect, the present invention is directed to an isolated nucleic acid molecule consisting of a polynucleotide having a nucleotide sequence selected from the group consisting of: (a) a polynucleotide encoding a polypeptide of SEQ ID NO:2; (b) a polynucleotide encoding a polypeptide encoded by a cDNA clone contained in one of ATCC Deposit Numbers PTA-4454 or PTA-4803, deposited on Jun. 12, 2002 and Nov. 14, 2002, respectively; and (c) a polynucleotide which represents the complimentary sequence (antisense) of SEQ ID NO:1.

In another aspect, the present invention is directed to an isolated nucleic acid molecule described above, wherein the polynucleotide comprises a nucleotide sequence encoding MGAT3.

In another aspect, the present invention is directed to a recombinant vector comprising the isolated nucleic acid molecule described above.

In another aspect, the present invention is directed to a recombinant host cell comprising a recombinant vector described above.

In another aspect, the present invention is directed to an isolated polypeptide consisting of an amino acid sequence selected from the group consisting of: (a) a full length protein of SEQ ID NO:2; (b) a polypeptide encoded by a cDNA contained in one of ATCC Deposit Numbers PTA-4454 or PTA-4803, deposited on Jun. 12, 2002 and Nov. 14, 2002, respectively.

In another aspect, the present invention is directed to the method of diagnosing a pathological condition, wherein the condition is a disorder related to aberrant MGAT activity, such as obesity, and a gastrointestinal disorder, such as Crohn's disease.

In another aspect, the present invention is directed to the method of preventing, treating, or ameliorating a medical condition, wherein the condition is a disorder related to aberrant MGAT activity, such as obesity, and a gastrointestinal disorder, such as Crohn's disease.

DETAILED DESCRIPTION OF THE INVENTION

The present invention may be understood more readily by reference to the following detailed description of the preferred embodiments of the invention and the Examples included herein.

The present invention is directed to a novel cDNA, designated monoacylglycerol acyltransferase-3 (hereinafter "MGAT3") which has substantial homology to known acylglycerol acyltransferase enzymes. MGAT3 is also known as DGA-C and DGA-3. MGAT3 encodes an MGAT protein having the amino acid sequence shown in FIG. 1A-B (SEQ ID NO:2) or the amino acid sequence encoded by a MGAT3 cDNA clone, deposited as ATCC Deposit Numbers PTA-4454 and PTA-4803 on Jun. 12, 2002 and Nov. 14, 2002, respectively. MGAT3 has the polynucleotide sequence set forth in FIG. 1A-B (SEQ ID NO:1) or the polynucleotide sequence of a MGAT3 cDNA clone, deposited as ATCC Deposit Numbers PTA-4454 and PTA-4803 on Jun. 12, 2002 and Nov. 14, 2002, respectively. MGAT3 has been identified using bioinformatic methods and cloned using molecular techniques. MGAT3 fulfills the criteria as the MGAT that is responsible for the absorption of dietary fat. The expression profile of human MGAT3 is highly restricted to gastrointestinal tract. As prevention of fat absorption is one of the proven methods to cause weight loss, intestinal MGAT inhibition, therefore, provides an approach for anti-obesity treatment. MGAT3 is therefore an important target for the treatment of obesity and related disease states.

The present invention also includes recombinant vectors, which include the isolated nucleic acid molecules of the present invention, and to host cells containing the recombinant vectors, as well as to methods of making such vectors and host cells, in addition to their use in the production of MGAT protein or peptides using recombinant techniques. Synthetic methods for producing the polypeptides and polynucleotides of the present invention are provided. Also provided are diagnostic methods for detecting diseases, disorders, and/or conditions related to MGAT polypeptides and polynucleotides, and therapeutic methods for treating such diseases, disorders, and/or conditions. The invention further relates to screening methods for identifying binding partners of the polypeptides, particularly activators and inhibitors of the novel MGAT polypeptides of the present invention.

MGAT3 fulfills the criteria as the MGAT that is responsible for the absorption of dietary fat. The expression profile of human MGAT3 is highly restricted to gastrointestinal tract. Specifically, MGAT3 transcripts are found in the ileum approximately 45,000 times greater than that observed in the majority of the tissue out side of the digestive system. When recombinant MGAT3 is expressed in baculovirus insect cell system, it produces robust MGAT enzyme activity. Importantly, recombinant MGAT3 possesses superior substrate specificity for the acylation of 2-monoacylglycerol over other stereoisomers, a requirement that must be fulfilled by the authentic intestinal MGAT.

Clinically, Crohn's disease is diagnosed as an intestinal disorder that impairs the absorption of calories (Kastin, D. A. and A. L. Buchman (2002) *Curr. Opin. Clin. Nutr. Metab. Care*, 5(6):699-706). As a result, patients are retarded with growth that is followed by regional enteritis (Hendrickson, B. A., R. Gokhale, and J. H. Cho (2002) *Clin. Microbiol. Rev.*, 15(1):79-94). In the present invention, it is demonstrated that the steady-state levels of MGAT3 mRNA are significantly reduced in the ileum of Crohn's disease patients. A consequence of such a deficiency is the accumulation of free fatty acids. It is well documented that fatty acids can act as inflammatory agents in the bowel and that the dietary management of fatty acids is a therapeutic approach to the treatment of various inflammatory bowel diseases, including Crohn's (Aldhous, M. C. et al. (2001) *Proc. Nutr. Soc.*, 60(4):457-61). The loss of MGAT3 expression is concordant with these observations.

Additionally, MGAT3 maps to intestinal muc3A locus on chromosome 7q22.1. This region has previously been labeled as a susceptibility locus for both Crohn's disease and ulcerative colitis (Satsangi, J., et al. (1996) *Nat. Genet.*, 14(2): 199-202). These findings further highlight the physiological significance of MGAT3 in the intestinal fat absorption and indicate that therapeutic approaches to replace MGAT3 function may serve to correct Crohn's disease. Furthermore, monitoring the loss of MGAT3 expression may serve as a biomarker for disease progression and as a tool for early diagnosis.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

As used herein, a "polynucleotide" refers to a molecule having a nucleic acid sequence contained in SEQ ID NO:1 or the cDNA contained within a MGAT3 clone, having one of ATCC Deposit Numbers PTA-4454 or PTA-4803, deposited on Jun. 12, 2002 and Nov. 14, 2002, respectively ("deposited clones"). The MGAT3 clones were deposited with the American Type Culture Collection ("ATCC"), which is located at 10801 University Boulevard, Manassas, Va. 20110-2209, USA. The ATCC deposit made in the present invention was made pursuant to the terms of the Budapest Treaty on the international recognition of the deposit of microorganisms for purposes of patent procedure. By way of example only, the polynucleotide can contain the nucleotide sequence of the full length cDNA sequence, including the 5' and 3' untranslated sequences, the coding region, with or without a signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

A "polynucleotide" of the present invention also includes those polynucleotides capable of hybridizing, under stringent hybridization conditions, to sequences contained in SEQ ID NO:1, the complement thereof, or the cDNA within the clones deposited with the ATCC. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65 degree C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20×SSPE=3M NaCl; 0.2M NaH2PO4; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 polynucleotide-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure and Molecular Properties, 2nd Ed., T. E. Creighton, W. H. Freeman and Company, New York (1993); Posttranslational Covalent Modification of Proteins, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992).)

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention).

It is another aspect of the present invention to provide modulators of MGAT3 which can affect the function or activity of MGAT3 in a cell in which MGAT3 function or activity is to be modulated or affected. In addition, modulators of MGAT3 can affect downstream systems and molecules that are regulated by, or which interact with, MGAT3 in the cell. Modulators of MGAT3 include compounds, materials, agents, drugs, and the like, that antagonize, inhibit, reduce, block, suppress, diminish, decrease, or eliminate MGAT3 function and/or activity. Such compounds, materials, agents, drugs and the like can be collectively termed "antagonists". Alternatively, modulators of MGAT3 include compounds, materials, agents, drugs, and the like, that agonize, enhance, increase, augment, or amplify MGAT3 function in a cell. Such compounds, materials, agents, drugs and the like can be collectively termed "agonists".

As used herein the terms "modulate" or "modulates" refer to an increase or decrease in the amount, quality or effect of a particular activity, DNA, RNA, or protein. The definition of "modulate" or "modulates" as used herein is meant to encompass agonists and/or antagonists of a particular activity, DNA, RNA, or protein.

The term "organism" as referred to herein is meant to encompass any organism referenced herein, though preferably to eukaryotic organisms, more preferably to mammals, and most preferably to humans.

The polynucleotide and polypeptides of the present invention are useful as probes for the identification and isolation of full-length cDNAs and/or genomic DNA which correspond to the polynucleotides of the present invention, as probes to hybridize and discover novel, related DNA sequences, as probes for positional cloning of this or a related sequence, as probe to "subtract-out" known sequences in the process of discovering other novel polynucleotides, as probes to quantify polynucleotide expression, and as probes for microarrays.

In addition, polynucleotides and polypeptides of the present invention may comprise one, two, three, four, five, six, seven, eight, or more membrane domains.

Also, in preferred embodiments the present invention provides methods for further refining the biological function of the polynucleotides and/or polypeptides of the present invention.

Specifically, the invention provides methods for using the polynucleotides and polypeptides of the invention to identify orthologs, homologs, paralogs, variants, and/or allelic variants of the invention. Also provided are methods of using the polynucleotides and polypeptides of the invention to identify the entire coding region of the invention, non-coding regions of the invention, regulatory sequences of the invention, and secreted, mature, pro-, prepro-, forms of the invention (as applicable).

In preferred embodiments, the invention provides methods for identifying the glycosylation sites inherent in the polynucleotides and polypeptides of the invention, and the subsequent alteration, deletion, and/or addition of said sites for a number of desirable characteristics which include, but are not limited to, augmentation of protein folding, inhibition of protein aggregation, regulation of intracellular trafficking to organelles, increasing resistance to proteolysis, modulation of protein antigenicity, and mediation of intercellular adhesion.

In further preferred embodiments, methods are provided for evolving the polynucleotides and polypeptides of the present invention using molecular evolution techniques in an effort to create and identify novel variants with desired structural, functional, and/or physical characteristics.

The present invention further provides for other experimental methods and procedures currently available to derive functional assignments. These procedures include but are not limited to spotting of clones on arrays, micro-array technology, PCR based methods (e.g., quantitative PCR), anti-sense methodology, gene knockout experiments, and other procedures that could use sequence information from clones to build a primer or a hybrid partner.

Based upon the strong homology to members of the DGAT gene family, the MGAT3 polypeptide is expected to share at least some biological activity with such family members. The tissue distribution of MGAT3, in conjunction with the strong homology to the DGAT gene family and their associated functions, suggests that the MGAT3 polynucleotides and polypeptides are involved in various pathological states including inflammatory bowel diseases, including Crohn's disease.

The MGAT3 polynucleotides and polypeptides of the present invention, including agonists and/or fragments thereof, have uses that include modulating inflammation, such as in mammalian intestine. MGAT3 polynucleotides and polypeptides of the present invention, including agonists and/or fragments thereof, may be useful in diagnosing, treating, prognosing, and/or preventing gastrointestinal disorders diseases or disorders, including obesity.

The strong homology to DGAT gene family members, combined with the predominate localized expression in the intestine, suggests the MGAT3 polynucleotides and polypeptides may be useful in treating, diagnosing, prognosing, and/or preventing gastrointestinal diseases and/or disorders, which include, but are not limited to, obesity, ulcers, irritable bowel syndrome, inflammatory bowel disease, diarrhea, traveler's diarrhea, drug-related diarrhea, polyps, absorption disorders, constipation, diverticulitis, vascular disease of the intestines, intestinal obstruction, intestinal infections, ulcerative colitis, Shigellosis, cholera, Crohn's Disease, amebiasis, enteric fever, Whipple's Disease, peritonitis, intrabdominal abscesses, hereditary hemochromatosis, gastroenteritis, viral gastroenteritis, food poisoning, mesenteric ischemia, mesenteric infarction, in addition to, metabolic diseases and/or disorders. Moreover, polynucleotides and polypeptides, including fragments and/or antagonists thereof, have uses which include, directly or indirectly, treating, preventing, diagnosing, and/or prognosing susceptibility to the following, non-limiting, gastrointestinal infections: *Salmonella* infection, *E. coli* infection, *E. coli* O157:H7 infection, Shiga Toxin-producing *E. coli* infection, *Campylobacter* infection (e.g., *Campylobacter* fetus, *Campylobacter* upsaliensis, *Campylobacter* hyointestinalis, *Campylobacter* lari, *Campylobacter jejuni*, *Campylobacter* concisus, *Campylobacter* mucosalis, *Campylobacter* sputorum, *Campylobacter* rectus, *Campylobacter* curvus, *Campylobacter* sputorum, etc.), *Heliobacter* infection (e.g., *Heliobacter* cinaedi, *Heliobacter* fennelliae, etc.) *Yersinia enterocolitica* infection, *Vibrio* sp. Infection (e.g., *Vibrio* mimicus, *Vibrio* parahaemolyticus, *Vibrio* fluvialis, *Vibrio* fumissii, *Vibrio* hollisae, *Vibrio* vulnificus, *Vibrio* alginolyticus, *Vibrio* metschnikovii, *Vibrio* damsela, *Vibrio* cincinnatiensis, etc.) *Aeromonas* infection (e.g., *Aeromonas* hydrophila, *Aeromonas* sobira, *Aeromonas* caviae, etc.), Plesiomonas shigelliodes infection, Giardia infection (e.g., Giardia lamblia, etc.), Cryptosporidium infection, *Listeria* infection, Entamoeba histolytica infection, Rotavirus infection, Norwalk virus infection, *Clostridium difficile* infection, *Clostriudium perfringens* infection, *Staphylococcus* infection, *Bacillus* infection, in addition to any other gastrointestinal disease and/or disorder implicated by the causative agents listed above or elsewhere herein.

MGAT3 polynucleotides and polypeptides, including fragments and/or antagonists thereof, may have uses which include identification of modulators of MGAT3 function including antibodies (for detection or neutralization), naturally-occurring modulators and small molecule modulators. Antibodies to domains (including MGAT3 epitopes provided herein) of the MGAT3 protein could be used as diagnostic agents of gastrointestinal disorders in patients.

MGAT3 polypeptides and polynucleotides are useful for diagnosing diseases related to over or under expression of MGAT3 proteins by identifying mutations in the MGAT3 gene using MGAT3 probes, or determining MGAT3 protein or mRNA expression levels. MGAT3 polypeptides are also useful for screening for compounds, which affect activity of the protein.

The glycerol phospholipid domain of MGAT3 is believed to be critical in acyltransferase reactions. Molecular genetic manipulation of the structure of this active site domain, particularly the predicted catalytic amino acids, and of other functional domains in the DGAT gene family (e.g., active site domain binding pocket) enables the production of MGATs with tailor-made activities. Thus, the MGAT3 polypeptides, and fragments thereof, as well as any homologous product resulting from genetic manipulation of the structure, are useful for NMR-based design of modulators of MGAT3 biological activity, and DGATs, in general.

MGAT3 polypeptides and polynucleotides have additional uses which include diagnosing diseases related to the over and/or under expression of MGAT3 by identifying mutations in the MGAT3 polynucleotide sequence by using MGAT3 sequences as probes or by determining MGAT3 protein or mRNA expression levels. MGAT3 polypeptides may be useful for screening compounds that affect the activity of the protein. MGAT3 peptides can also be used for the generation of specific antibodies and as bait in yeast two hybrid screens to find proteins the specifically interact with MGAT3.

The MGAT3 polynucleotides and polypeptides, including fragments and agonists thereof, may have uses which include detecting, diagnosing, treating, ameliorating, and/or preventing diseases and disorders, such as obesity and Crohn's disease.

Although it is believed the encoded polypeptide may share at least some biological activities with DGAT family members, a number of methods of determining the exact biological function of this clone are either known in the art or are described elsewhere herein. Briefly, the function of this clone may be determined by applying microarray methodology. Nucleic acids corresponding to the MGAT3 polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from diseased intestinal tissue, as compared to, normal intestinal tissue might indicate a function in modulating intestinal function, for example.

In addition, the function of the protein may be assessed by applying quantitative PCR methodology, for example. Real time quantitative PCR would provide the capability of following the expression of the MGAT3 gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. In the case of MGAT3, a disease correlation related to MGAT3 may be made by comparing the mRNA expression level of MGAT3 in normal tissue, as compared to diseased tissue (particularly diseased intestinal tissue). Significantly higher or lower levels of MGAT3 expression in the diseased tissue suggest MGAT3 plays a role in disease progression, and antagonists against MGAT3 polypeptides would be useful therapeutically in treating, preventing, and/or ameliorating the disease. Alternatively, significantly higher or lower levels of MGAT3 expression in the diseased tissue may suggest MGAT3 plays a defensive role against disease progression, and agonists of MGAT3 polypeptides may be useful therapeutically in treating, preventing, and/or ameliorating the disease. Also encompassed by the present invention are quantitative PCR probes corresponding to the polynucleotide sequence provided as SEQ ID NO:1 (FIG. 1A-B).

The function of the protein may also be assessed through complementation assays in yeast. For example, in the case of the MGAT3, transforming yeast deficient in MGAT activity and assessing their ability to grow would provide convincing evidence the MGAT3 polypeptide has MGAT activity. Additional assay conditions and methods that may be used in assessing the function of the polynucleotides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype. Such knock-out experiments are known in the art, some of which are disclosed elsewhere herein.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter or it can be expressed at a specified time of development using an inducible and/or a developmentally regulated promoter.

In the case of MGAT3 transgenic mice or rats, if no phenotype is apparent in normal growth conditions, observing the organism under diseased conditions may lead to understanding the function of the gene. Therefore, the application of antisense and/or sense methodology to the creation of transgenic mice or rats to refine the biological function of the polypeptide is encompassed by the present invention.

In preferred embodiments, the following N-terminal MGAT3 deletion polypeptides are encompassed by the present invention: M1-I341, G2-I341, V3-I341, A4-I341, T5-I341, T6-I341, L7-I341, Q8-I341, P9-I341, P10-I341, T11-I341, T12-I341, S13-I341, K14-I341, T15-I341, L16-I341, Q17-I341, K18-I341, Q19-I341, H20-I341, L21-I341, E22-I341, A23-I341, V24-I341, G25-I341, A26-I341, Y27-I341, Q28-I341, Y29-I341, V30-I341, L31-I341, T32-I341, F33-I341, L34-I341, F35-I341, M36-I341, G37-I341, P38-I341, F39-I341, F40-I341, S41-I341, L42-I341, L43-I341, V44-I341, F45-I341, V46-I341, L47-I341, L48-I341, F49-I341, T50-I341, S51-I341, L52-I341, W53-I341, P54-I341, F55-I341, S56-I341, V57-I341, F58-I341, Y59-I341, L60-I341, V61-I341, W62-I341, L63-I341, Y64-I341, V65-I341, D66-I341, W67-I341, D68-I341, T69-I341, P70-I341, N71-I341, Q72-I341, G73-I341, G74-I341, R75-I341, R76-I341, S77-I341, E78-I341, W79-I341, I80-I341, R81-I341, N82-I341, R83-I341, A84-I341, I85-I341, W86-I341, R87-I341, Q88-I341, L89-I341, R90-I341, D91-I341, Y92-I341, Y93-I341, P94-I341, V95-I341, K96-I341, L97-I341, V98-I341, K99-I341, T100-I341, A101-I341, E102-I341, L103-I341, P104-I341, P105-I341, D106-I341, R107-I341, N108-I341, Y109-I341, V110-I341, L111-I341, G112-I341, A113-I341, H114-I341, P115-I341, H116-I341, G117-I341, I118-I341, M119-I341, C120-I341, T121-I341, G122-I341, F123-I341, L124-I341, C125-I341, N126-I341, F127-I341, S128-I341, T129-I341, E130-I341, S131-I341, N132-I341, G133-I341, F134-I341, S135-I341, Q136-I341, L137-I341, F138-I341, P139-I341, G140-I341, L141-I341, R142-I341, P143-I341, W144-I341, L145-I341, A146-I341, V147-I341, L148-I341, A149-I341, G150-I341, L151-I341, F152-I341, Y153-I341, L154-I341, P155-I341, V156-I341, Y157-I341, R158-I341, D159-I341, Y160-I341, I161-I341, M162-I341, S163-I341, F164-I341, G165-I341, L166-I341, C167-I341, P168-I341, V169-I341, S170-I341, R171-I341, Q172-I341, S173-I341, L174-I341, D175-I341, F176-I341, I177-I341, L178-I341, S179-I341, Q180-I341, P181-I341, Q182-I341, L183-I341, G184-I341, Q185-I341, A186-I341, V187-I341, V188-I341, I189-I341, M190-I341, V191-I341, G192-I341, G193-I341, A194-I341, H195-I341, E196-I341, A197-I341, L198-I341, Y199-I341, S200-I341, V201-I341, P202-I341, G203-I341, E204-I341, H205-I341, C206-I341, L207-I341, T208-I341, L209-I341, Q210-I341, K211-I341, R212-I341, K213-I341, G214-I341, F215-I341, V216-I341, R217-I341, L218-I341, A219-I341, L220-I341, R221-I341, H222-I341, G223-I341, A224-I341, S225-I341, L226-I341, V227-I341, P228-I341, V229-I341, Y230-I341, S231-I341, F232-I341, G233-I341, E234-I341, N235-I341, D236-I341, I237-I341, F238-I341, R239-I341, L240-I341, K241-I341, A242-I341, F243-I341, A244-I341, T245-I341, G246-I341, S247-I341, W248-I341, Q249-I341, H250-I341, W251-I341, C252-I341, Q253-I341, L254-I341, T255-I341, F256-I341, K257-I341, K258-I341, L259-I341, M260-I341, G261-I341, F262-I341, S263-I341, P264-I341, C265-I341, I266-I341, F267-I341, W268-I341, G269-I341, R270-I341, G271-I341, L272-I341, F273-I341, S274-I341, A275-I341, T276-I341, S277-I341, W278-I341, G279-I341, L280-I341, L281-I341, P282-I341, F283-I341, A284-I341, V285-I341, P286-I341, I287-I341, T288-I341, T289-I341, V290-I341, V291-I341, G292-I341, R293-I341, P294-I341, I295-I341, P296-I341, V297-I341, P298-I341, Q299-I341, R300-I341, L301-I341, H302-I341, P303-I341, T304-I341, E305-I341, E306-I341, E307-I341, V308-

I341, N309-I341, H310-I341, Y311-I341, H312-I341, A313-I341, L314-I341, Y315-I341, M316-I341, T317-I341, A318-I341, L319-I341, E320-I341, Q321-I341, L322-I341, F323-I341, E324-I341, E325-I341, H326-I341, K327-I341, E328-I341, S329-I341, C330-I341, G331-I341, V332-I341, P333-I341, A334-I341, and/or S335-I341 of SEQ ID NO:2.

Polynucleotide sequences encoding these polypeptides are also provided. The present invention also encompasses the use of these N-terminal MGAT3 deletion polypeptides as immunogenic and/or antigenic epitopes as described elsewhere herein.

In preferred embodiments, the following C-terminal MGAT3 deletion polypeptides are encompassed by the present invention: M1-I341, M1-F340, M1-T339, M1-L338, M1-C337, M1-T336, M1-S335, M1-A334, M1-P333, M1-V332, M1-G331, M1-C330, M1-S329, M1-E328, M1-K327, M1-H326, M1-E325, M1-E324, M1-F323, M1-L322, M1-Q321, M1-E320, M1-L319, M1-A318, M1-T317, M1-M316, M1-Y315, M1-L314, M1-A313, M1-H312, M1-Y311, M1-H310, M1-N309, M1-V308, M1-E307, M1-E306, M1-E305, M1-T304, M1-P303, M1-H302, M1-L301, M1-R300, M1-Q299, M1-P298, M1-V297, M1-P296, M1-I295, M1-P294, M1-R293, M1-G292, M1-V291, M1-V290, M1-T289, M1-T288, M1-I287, M1-P286, M1-V285, M1-A284, M1-F283, M1-P282, M1-L281, M1-L280, M1-G279, M1-W278, M1-S277, M1-T276, M1-A275, M1-S274, M1-F273, M1-L272, M1-G271, M1-R270, M1-G269, M1-W268, M1-F267, M1-I266, M1-C265, M1-P264, M1-S263, M1-F262, M1-G261, M1-M260, M1-L259, M1-K258, M1-K257, M1-F256, M1-T255, M1-L254, M1-Q253, M1-C252, M1-W251, M1-H250, M1-Q249, M1-W248, M1-S247, M1-G246, M1-T245, M1-A244, M1-F243, M1-A242, M1-K241, M1-L240, M1-R239, M1-F238, M1-I237, M1-D236, M1-N235, M1-E234, M1-G233, M1-F232, M1-S231, M1-Y230, M1-V229, M1-P228, M1-V227, M1-L226, M1-S225, M1-A224, M1-G223, M1-H222, M1-R221, M1-L220, M1-A219, M1-L218, M1-R217, M1-V216, M1-F215, M1-G214, M1-K213, M1-R212, M1-K211, M1-Q210, M1-L209, M1-T208, M1-L207, M1-C206, M1-H205, M1-E204, M1-G203, M1-P202, M1-V201, M1-S200, M1-Y199, M1-L198, M1-A197, M1-E196, M1-H195, M1-A194, M1-G193, M1-G192, M1-V191, M1-M190, M1-189, M1-V188, M1-V187, M1-A186, M1-Q185, M1-G184, M1-L183, M1-Q182, M1-P181, M1-Q180, M1-S179, M1-L178, M1-I177, M1-F176, M1-D175, M1-L174, M1-S173, M1-Q172, M1-R171, M1-S170, M1-V169, M1-P168, M1-C167, M1-L166, M1-G165, M1-F164, M1-S163, M1-M162, M1-I161, M1-Y160, M1-D159, M1-R158, M1-Y157, M1-V156, M1-P155, M1-L154, M1-Y153, M1-F152, M1-L151, M1-G150, M1-A149, M1-L148, M1-V147, M1-A146, M1-L145, M1-W144, M1-P143, M1-R142, M1-L141, M1-G140, M1-P139, M1-F138, M1-L137, M1-Q136, M1-S135, M1-F134, M1-G133, M1-N132, M1-S131, M1-E130, M1-T129, M1-S128, M1-F127, M1-N126, M1-C125, M1-L124, M1-F123, M1-G122, M1-T121, M1-C120, M1-M119, M1-I118, M1-G117, M1-H116, M1-P115, M1-H114, M1-A113, M1-G112, M1-L111, M1-V110, M1-Y109, M1-N108, M1-R107, M1-D106, M1-P105, M1-P104, M1-L103, M1-E102, M1-A101, M1-T100, M1-K99, M1-V98, M1-L97, M1-K96, M1-V95, M1-P94, M1-Y93, M1-Y92, M1-D91, M1-R90, M1-L89, M1-Q88, M1-R87, M1-W86, M1-185, M1-A84, M1-R83, M1-N82, M1-R81, M1-I80, M1-W79, M1-E78, M1-S77, M1-R76, M1-R75, M1-G74, M1-G73, M1-Q72, M1-N71, M1-P70, M1-T69, M1-D68, M1-W67, M1-D66, M1-V65, M1-Y64, M1-L63, M1-W62, M1-V61, M1-L60, M1-Y59, M1-F58, M1-V57, M1-S56, M1-F55, M1-P54, M1-W53, M1-L52, M1-S51, M1-T50, M1-F49, M1-L48, M1-L47, M1-V46, M1-F45, M1-V44, M1-L43, M1-L42, M1-S41, M1-F40, M1-F39, M1-P38, M1-G37, M1-M36, M1-F35, M1-L34, M1-F33, M1-T32, M1-L31, M1-V30, M1-Y29, M1-Q28, M1-Y27, M1-A26, M1-G25, M1-V24, M1-A23, M1-E22, M1-L21, M1-H20, M1-Q19, M1-K18, M1-Q17, M1-L16, M1-T15, M1-K14, M1-S13, M1-T12, M1-T11, M1-P10, M1-P9, M1-Q8, and/or M1-L7 of SEQ ID NO:2.

Polynucleotide sequences encoding these polypeptides are also provided. The present invention also encompasses the use of these C-terminal MGAT3 deletion polypeptides as immunogenic and/or antigenic epitopes as described elsewhere herein.

Alternatively, preferred polypeptides of the present invention may comprise polypeptide sequences corresponding to, for example, internal regions of the MGAT3 polypeptide (e.g., any combination of both N- and C-terminal MGAT3 polypeptide deletions) of SEQ ID NO:2. For example, internal regions could be defined by the equation: amino acid NX to amino acid CX, wherein NX refers to any N-terminal deletion polypeptide amino acid of MGAT3 (SEQ ID NO:2), and where CX refers to any C-terminal deletion polypeptide amino acid of MGAT (SEQ ID NO:2). Polynucleotides encoding these polypeptides are also provided. The present invention also encompasses the use of these polypeptides as an immunogenic and/or antigenic epitope as described elsewhere herein.

The MGAT3 polypeptides of the present invention have been shown to comprise one amidation site according to the Motif algorithm (Genetics Computer Group, Inc.). The precursor of hormones and other active peptides which are C-terminally amidated is always directly followed by a glycine residue which provides the amide group, and most often by at least two consecutive basic residues (Arg or Lys) which generally function as an active peptide precursor cleavage site. Although all amino acids can be amidated, neutral hydrophobic residues such as Val or Phe are good substrates, while charged residues such as Asp or Arg are much less reactive. A consensus pattern for amidation sites is the following: xG(R,K)(R,K), wherein "x" represents the amidation site. Additional information relating to Asparagine glycosylation may be found in reference to the following publications, which are hereby incorporated by reference herein: Kreil G. (1984) *Meth. Enzymol.* 106:218-223; and Bradbury A. F., Smyth D. G. (1987) *Biosci. Rep.* 7:907-916.

In preferred embodiments, the following amidation site polypeptide is encompassed by the present invention: DTP-NQGGRRSEWIR (SEQ ID NO:25). Polynucleotides encoding these polypeptides are also provided. The present invention also encompasses the use of this MGAT3 amidation site polypeptide as an immunogenic and/or antigenic epitope as described elsewhere herein.

The MGAT3 polypeptides of the present invention were determined to comprise several phosphorylation sites based upon the Motif algorithm (Genetics Computer Group, Inc.). The phosphorylation of such sites may regulate some biological activity of the MGAT3 polypeptide. For example, phosphorylation at specific sites may be involved in regulating the proteins ability to associate or bind to other molecules (e.g., proteins, ligands, substrates, DNA, etc.).

The MGAT3 polypeptide was predicted to comprise two PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: (S,T)$_x$(R,K), where S or T represents the site of phosphorylation and 'x' an intervening amino acid residue.

Additional information regarding PKC phosphorylation sites can be found in Woodget J. R., et al. (1986) *Eur. J. Biochem.* 161:177-184, and Kishimoto A., et al. (1985) *J. Biol. Chem.* 260:12492-12499; which are hereby incorporated by reference herein. In preferred embodiments, the following PKC phosphorylation site polypeptides are encompassed by the present invention: LQPPTTSKTLQKQ (SEQ ID NO:13), and/or HWCQLTFKKLMGF (SEQ ID NO:14). Polynucleotides encoding these polypeptides are also provided. The present invention also encompasses the use of these MGAT3 PKC phosphorylation site polypeptides as immunogenic and/or antigenic epitopes as described elsewhere herein.

The MGAT3 polypeptide was predicted to comprise three casein kinase II phosphorylation sites using the Motif algorithm (Genetics Computer Group, Inc.). Casein kinase II (CK-2) is a protein serine/threonine kinase whose activity is independent of cyclic nucleotides and calcium. CK-2 phosphorylates many different proteins. The substrate specificity of this enzyme can be summarized as follows: (1) Under comparable conditions Ser is favored over Thr.; (2) An acidic residue (either Asp or Glu) must be present three residues from the C-terminal of the phosphate acceptor site; (3) Additional acidic residues in positions +1, +2, +4, and +5 increase the phosphorylation rate. Most physiological substrates have at least one acidic residue in these positions; (4) Asp is preferred to Glu as the provider of acidic determinants; and (5) A basic residue at the N-terminal of the acceptor site decreases the phosphorylation rate, while an acidic one will increase it.

A consensus pattern for casein kinase II phosphorylations site is as follows: (S,T)x2(D,E), wherein 'x' represents any amino acid, and S or T is the phosphorylation site.

Additional information specific to casein kinase II phosphorylation sites may be found in reference to the following publication: Pinna L. A. (1990) *Biochim. Biophys. Acta* 1054:267-284; which is hereby incorporated herein in its entirety.

In preferred embodiments, the following casein kinase II phosphorylation site polypeptide is encompassed by the present invention: LVPVYSFGENDIFR (SEQ ID NO:4), QRLHPTEEEVNHYH (SEQ ID NO:5), and/or HALYMTALEQLFEE (SEQ ID NO:6). Polynucleotides encoding these polypeptides are also provided. The present invention also encompasses the use of this casein kinase II phosphorylation site polypeptide as an immunogenic and/or antigenic epitope as described elsewhere herein.

The MGAT3 polypeptide has been shown to comprise one glycosylation site according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

Asparagine glycosylation sites have the following consensus pattern, N-(P)(S,T)-(P), wherein N represents the glycosylation site. However, it is well known that that potential N-glycosylation sites are specific to the consensus sequence Asn-Xaa-Ser/Thr. However, the presence of the consensus tripeptide is not sufficient to conclude that an Asparagine residue is glycosylated, due to the fact that the folding of the protein plays an important role in the regulation of N-glycosylation. It has been shown that the presence of proline between Asn and Ser/Thr will inhibit N-glycosylation; this has been confirmed by a recent statistical analysis of glycosylation sites, which also shows that about 50% of the sites that have a proline C-terminal to Ser/Thr are not glycosylated. Additional information relating to Asparagine glycosylation may be found in reference to the following publications, which are hereby incorporated by reference herein: Marshall R. D. (1972) *Annu. Rev. Biochem.*, 41:673-702; Pless D. D., Lennarz W. J. (1977) *Proc. Natl. Acad. Sci.*, U.S.A. 74:134-138; Bause E. (1983) *Biochem. J.* 209:331-336; Gavel Y., von Heijne G. (1990) *Protein Eng.*, 3:433-442; and Miletich J. P., Broze G. J. Jr. (1990) *J. Biol. Chem.*, 265:11397-11404.

In preferred embodiments, the following Asparagine glycosylation site polypeptide is encompassed by the present invention: TGFLCNFSTESNGF (SEQ ID NO:3). Polynucleotides encoding this polypeptide are also provided. The present invention also encompasses the use of this MGAT3 Asparagine glycosylation site polypeptide as immunogenic and/or antigenic epitope as described elsewhere herein.

The MGAT3 polypeptide was predicted to comprise five N-myristoylation sites using the Motif algorithm (Genetics Computer Group, Inc.). An appreciable number of eukaryotic proteins are acylated by the covalent addition of myristate (a C14-saturated fatty acid) to their N-terminal residue via an amide linkage. The sequence specificity of the enzyme responsible for this modification, myristoyl CoA: protein N-myristoyl transferase (NMT), has been derived from the sequence of known N-myristoylated proteins and from studies using synthetic peptides. The specificity seems to be the following: i.) The N-terminal residue must be glycine; ii.) In position 2, uncharged residues are allowed; iii.) Charged residues, proline and large hydrophobic residues are not allowed; iv.) In positions 3 and 4, most, if not all, residues are allowed; v.) In position 5, small uncharged residues are allowed (Ala, Ser, Thr, Cys, Asn and Gly). Serine is favored; and vi.) In position 6, proline is not allowed.

A consensus pattern for N-myristoylation is as follows: G-(E,D,R,K,H,P,F,Y,W)x2(S,T,A,G,C,N)-(P), wherein 'x' represents any amino acid, and G is the N-myristoylation site.

Additional information specific to N-myristoylation sites may be found in reference to the following publication: Towler D. A., et al. (1988) *Annu. Rev. Biochem.* 57:69-99 (1988); and Grand R. J. A. (1989) *Biochem. J.* 258:625-638; which is hereby incorporated herein in its entirety.

In preferred embodiments, the following N-myristoylation site polypeptides are encompassed by the present invention: MGVATTLQPPTT (SEQ ID NO:7), DTPNQG-GRRSEWIRNR (SEQ ID NO:8), GAHPHGIMCTGFLCNF (SEQ ID NO:9), VIMVGGAHEALYSVPG (SEQ ID NO:10), IFWGRGLFSATSWGLL (SEQ ID NO:11), and/or HKESCGVPASTCLTFI (SEQ ID NO:12). Polynucleotides encoding these polypeptides are also provided. The present invention also encompasses the use of these N-myristoylation site polypeptides as immunogenic and/or antigenic epitopes as described elsewhere herein.

The present invention also encompasses immunogenic and/or antigenic epitopes of the MGAT3 polypeptide.

MGAT3 includes a putative glycerol phospholipid domain (GenBank Accession Number PS50239; Coleman, R. A., et al. (1978) *J. Biol. Chem.*, 253(20):7256-61), which is shown in bold in FIG. 1A and is preferably from about amino acid F152 to amino acid R239.

Also provided in the present invention are species homologs, allelic variants, and/or orthologs. The skilled artisan could, using procedures well-known in the art, obtain the polynucleotide sequence corresponding to full-length genes (including, but not limited to the full-length coding region), allelic variants, splice variants, orthologs, and/or species homologues of genes corresponding to SEQ ID NO:1, SEQ ID NO:2, or at least one deposited clone, relying on the sequence from the sequences disclosed herein or the clones deposited with the ATCC. For example, allelic variants and/or species homologues may be isolated and identified by making suitable probes or primers which correspond to the 5', 3', or internal regions of the sequences provided herein and screening a suitable nucleic acid source for allelic variants and/or the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the protein, or may be a part of a larger protein, such as a fusion protein. It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, can be substantially purified using techniques described herein or otherwise known in the art, such as, for example, by the one-step method described in Smith and Johnson, Gene 67:31-40 (1988). Polypeptides of the invention also can be purified from natural, synthetic or recombinant sources using protocols described herein or otherwise known in the art, such as, for example, antibodies of the invention raised against the full-length form of the protein.

The present invention encompasses polynucleotides with sequences complementary to those of the polynucleotides of the present invention disclosed herein. Such sequences may be complementary to the sequence disclosed as SEQ ID NO:1, the sequence contained in a deposit, and/or the nucleic acid sequence encoding the sequence disclosed as SEQ ID NO:2.

The present invention also encompasses polynucleotides capable of hybridizing, preferably under reduced stringency conditions, more preferably under stringent conditions, and most preferably under highly stringent conditions, to polynucleotides described herein. Examples of stringency conditions are shown in Table I below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE I

Stringency Conditions

| Stringency Condition | Polynucleotide Hybrid± | Hybrid Length (bp)‡ | Hybridization Temperature and Buffer† | Wash Temperature and Buffer† |
| --- | --- | --- | --- | --- |
| A | DNA:DNA | >or equal to 50 | 65° C.; 1xSSC - or –42° C.; 1xSSC, 50% formamide | 65° C.; 0.3xSSC |
| B | DNA:DNA | <50 | Tb*; 1xSSC | Tb*; 1xSSC |
| C | DNA:RNA | >or equal to 50 | 67° C.; 1xSSC - or –45° C.; 1xSSC, 50% formamide | 67° C.; 0.3xSSC |
| D | DNA:RNA | <50 | Td*; 1xSSC | Td*; 1xSSC |
| E | RNA:RNA | >or equal to 50 | 70° C.; 1xSSC - or –50° C.; 1xSSC, 50% formamide | 70° C.; 0.3xSSC |
| F | RNA:RNA | <50 | Tf*; 1xSSC | Tf*; 1xSSC |
| G | DNA:DNA | >or equal to 50 | 65° C.; 4xSSC - or –45° C.; 4xSSC, 50% formamide | 65° C.; 1xSSC |
| H | DNA:DNA | <50 | Th*; 4xSSC | Th*; 4xSSC |
| I | DNA:RNA | >or equal to 50 | 67° C.; 4xSSC - or –45° C.; 4xSSC, 50% formamide | 67° C.; 1xSSC |
| J | DNA:RNA | <50 | Tj*; 4xSSC | Tj*; 4xSSC |
| K | RNA:RNA | >or equal to 50 | 70° C.; 4xSSC - or –40° C.; 6xSSC, 50% formamide | 67° C.; 1xSSC |
| L | RNA:RNA | <50 | Tl*; 2xSSC | Tl*; 2xSSC |

TABLE I-continued

Stringency Conditions

| Stringency Condition | Polynucleotide Hybrid± | Hybrid Length (bp)‡ | Hybridization Temperature and Buffer† | Wash Temperature and Buffer† |
|---|---|---|---|---|
| M | DNA:DNA | >or equal to 50 | 50° C.; 4xSSC - or −40° C. 6xSSC, 50% formamide | 50° C.; 2xSSC |
| N | DNA:DNA | <50 | Tn*; 6xSSC | Tn*; 6xSSC |
| O | DNA:RNA | >or equal to 50 | 55° C.; 4xSSC - or −42° C.; 6xSSC, 50% formamide | 55° C.; 2xSSC |
| P | DNA:RNA | <50 | Tp*; 6xSSC | Tp*; 6xSSC |
| Q | RNA:RNA | >or equal to 50 | 60° C.; 4xSSC - or −45° C.; 6xSSC, 50% formamide | 60° C.; 2xSSC |
| R | RNA:RNA | <50 | Tr*; 4xSSC | Tr*; 4xSSC |

‡The "hybrid length" is the anticipated length for the hybridized region(s) of the hybridizing polynucleotides. When hybridizing a polynucleotide of unknown sequence, the hybrid length is assumed to be that of the hybridizing polynucleotide of the present invention. When polynucleotides of known sequence are hybridized, the hybrid length can be determined by aligning the sequences of the polynucleotides and identifying the region or regions of optimal sequence complementarity. Methods of aligning two or more polynucleotide sequences and/or determining the percent identity between two polynucleotide sequences are well known in the art (e.g., MegAlign program of the DNA *Star suite of programs, etc).
†SSPE (1xSSPE is 0.15M NaCl, 10 mM NaH2PO4, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete. The hydridizations and washes may additionally include 5X Denhardt's reagent, .5–1.0% SDS, 100 ug/ml denatured, fragmented salmon sperm DNA, 0.5% sodium pyrophosphate, and up to 50% formamide.
*Tb-Tr: The hybridization temperature for hybrids anticipated to be less than 50 base pairs in length should be 5–10° C. less than the melting temperature Tm of the hybrids there Tm is determined according to the following equations. For hybrids less than 18 base pairs in length, $Tm(° C.) = 2(\text{\# of A + T bases}) + 4(\text{\# of G + C bases})$. For hybrids between 18 and 49 base pairs in length, $Tm(° C.) = 81.5 + 16.6(\log_{10}[Na+]) + 0.41(\% G + C) - (600/N)$, where N is the number of bases in the hybrid, and [Na+] is the concentration of sodium ions in the hybridization buffer ([NA+] for 1xSSC = .165 M).
±The present invention encompasses the substitution of any one, or more DNA and RNA hybrid partners with either a PNA, or a modified polynucleotide. Such modified polynucleotides are known in the art and are more particularly described elsewhere herein.

Additional examples of stringency conditions for polynucleotide hybridization are provided, for example, in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M., Ausubel et al., eds, John Wiley and Sons, Inc., sections 2.10 and 6.3-6.4, which are hereby incorporated by reference herein.

Preferably, such hybridizing polynucleotides have at least 70% sequence identity (more preferably, at least 80% identity; and most preferably at least 90% or 95% identity) with the polynucleotide of the present invention to which they hybridize, where sequence identity is determined by comparing the sequences of the hybridizing polynucleotides when aligned so as to maximize overlap and identity while minimizing sequence gaps. The determination of identity is well known in the art, and described more specifically elsewhere herein.

The invention encompasses the application of PCR methodology to the polynucleotide sequences of the present invention, the clone deposited with the ATCC, and/or the cDNA encoding the polypeptides of the present invention. PCR techniques for the amplification of nucleic acids are described in U.S. Pat. No. 4,683,195 and Saiki et al. (1988) Science, 239:487-491. PCR, for example, may include the following steps, of denaturation of template nucleic acid (if double-stranded), annealing of primer to target, and polymerization. The nucleic acid probed or used as a template in the amplification reaction may be genomic DNA, cDNA, RNA, or a PNA. PCR may be used to amplify specific sequences from genomic DNA, specific RNA sequence, and/or cDNA transcribed from mRNA. References for the general use of PCR techniques, including specific method parameters, include Mullis et al. (1987) Cold Spring Harbor Symp. Quant. Biol., 51:263, Ehrlich (ed), PCR Technology, Stockton Press, NY, 1989; Ehrlich et al. (1991) Science, 252:1643-1650; and "PCR Protocols, A Guide to Methods and Applications", Eds., Innis et al., Academic Press, New York, (1990).

The present invention also encompasses mature forms of the polypeptide comprising, or alternatively consisting of, the polypeptide sequence of SEQ ID NO:2, the polypeptide encoded by the polynucleotide described as SEQ ID NO:1, and/or the polypeptide sequence encoded by a cDNA in at least one deposited clone. The present invention also encompasses polynucleotides encoding mature forms of the present invention, such as, for example the polynucleotide sequence of SEQ ID NO:1, and/or the polynucleotide sequence provided in a cDNA of at least one deposited clone.

According to the signal hypothesis, proteins secreted by eukaryotic cells have a signal or secretary leader sequence which is cleaved from the mature protein once export of the growing protein chain across the rough endoplasmic reticulum has been initiated. Most eukaryotic cells cleave secreted proteins with the same specificity. However, in some cases, cleavage of a secreted protein is not entirely uniform, which results in two or more mature species of the protein. Further, it has long been known that cleavage specificity of a secreted protein is ultimately determined by the primary structure of the complete protein, that is, it is inherent in the amino acid sequence of the polypeptide.

Methods for predicting whether a protein has a signal sequence, as well as the cleavage point for that sequence, are available. For instance, the method of McGeoch, *Virus Res.* 3:271-286 (1985), uses the information from a short N-terminal charged region and a subsequent uncharged region of the complete (uncleaved) protein. The method of von Heinje, *Nucleic Acids Res.* 14:4683-4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75-80%. (von Heinje, supra.) However, the two methods do not always produce the same predicted cleavage point(s) for a given protein.

The established method for identifying the location of signal sequences, in addition, to their cleavage sites has been the SignalP program (v1.1) developed by Henrik Nielsen et al., *Protein Engineering* 10:1-6 (1997). The program relies upon the algorithm developed by von Heinje, though provides additional parameters to increase the prediction accuracy.

More recently, a hidden Markov model has been developed (H. Neilson, et al., Ismb 1998;6:122-30), which has been incorporated into the more recent SignalP (v2.0). This new method increases the ability to identify the cleavage site by discriminating between signal peptides and uncleaved signal anchors. The present invention encompasses the application of the method disclosed therein to the prediction of the signal peptide location, including the cleavage site, to any of the polypeptide sequences of the present invention.

As one of ordinary skill would appreciate, however, cleavage sites sometimes vary from organism to organism and cannot be predicted with absolute certainty. Accordingly, the polypeptide of the present invention may contain a signal sequence. Polypeptides of the invention which comprise a signal sequence have an N-terminus beginning within 5 residues (i.e., + or −5 residues, or Preferably at the −5, −4, −3, −2, −1, +1, +2, +3, +4, or +5 residue) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. Nonetheless, the present invention provides the mature protein produced by expression of the polynucleotide sequence of SEQ ID NO:1 and/or the polynucleotide sequence contained in the cDNA of at least one deposited clone, in a mammalian cell (e.g., COS cells, as described below). These polypeptides, and the polynucleotides encoding such polypeptides, are contemplated by the present invention.

The present invention also encompasses variants (e.g., allelic variants, orthologs, etc.) of the polynucleotide sequence disclosed herein in SEQ ID NO:1, the complementary strand thereto, and/or the cDNA sequence contained in at least one deposited clone.

The present invention also encompasses variants of the polypeptide sequence, and/or fragments therein, disclosed in SEQ ID NO:2, a polypeptide encoded by the polynucleotide sequence in SEQ ID NO:1, and/or a polypeptide encoded by a cDNA in at least one deposited clone.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

Thus, one aspect of the invention provides an isolated nucleic acid molecule comprising, or alternatively consisting of, a polynucleotide having a nucleotide sequence selected from the group consisting of: (a) a nucleotide sequence encoding a MGAT3 related polypeptide having an amino acid sequence as shown in the sequence listing and described in SEQ ID NO:1 or a cDNA contained in one of ATCC Deposit Numbers PTA-4454 or PTA-4803, deposited on Jun. 12, 2002 and Nov. 14, 2002, respectively; (b) a nucleotide sequence encoding a mature MGAT3 related polypeptide having the amino acid sequence as shown in the sequence listing and described in SEQ ID NO:1 or a cDNA contained in one of ATCC Deposit Numbers PTA-4454 or PTA-4803, deposited on Jun. 12, 2002 and Nov. 14, 2002, respectively; (c) a nucleotide sequence encoding a biologically active fragment of a MGAT3 related polypeptide having an amino acid sequence shown in the sequence listing and described in SEQ ID NO:1 or a cDNA contained in one of ATCC Deposit Numbers PTA-4454 or PTA-4803, deposited on Jun. 12, 2002 and Nov. 14, 2002, respectively; (d) a nucleotide sequence encoding an antigenic fragment of a MGAT3 related polypeptide having an amino acid sequence shown in the sequence listing and described in SEQ ID NO:1 or a cDNA contained in one of ATCC Deposit Numbers PTA-4454 or PTA-4803, deposited on Jun. 12, 2002 and Nov. 14, 2002, respectively; (e) a nucleotide sequence encoding a MGAT3 related polypeptide comprising the complete amino acid sequence encoded by a human cDNA plasmid contained in SEQ ID NO:1 or a cDNA contained in one of ATCC Deposit Numbers PTA-4454 or PTA-4803, deposited on Jun. 12, 2002 and Nov. 14, 2002, respectively; (f) a nucleotide sequence encoding a mature MGAT3 related polypeptide having an amino acid sequence encoded by a human cDNA plasmid contained in SEQ ID NO:1 or a cDNA contained in one of ATCC Deposit Numbers PTA-4454 or PTA-4803, deposited on Jun. 12, 2002 and Nov. 14, 2002, respectively; (g) a nucleotide sequence encoding a biologically active fragment of a MGAT3 related polypeptide having an amino acid sequence encoded by a human cDNA plasmid contained in SEQ ID NO:1 or a cDNA contained in one of ATCC Deposit Numbers PTA-4454 or PTA-4803, deposited on Jun. 12, 2002 and Nov. 14, 2002, respectively; (h) a nucleotide sequence encoding an antigenic fragment of a MGAT3 related polypeptide having an amino acid sequence encoded by a human cDNA plasmid contained in SEQ ID NO:1 or a cDNA contained in one of ATCC Deposit Numbers PTA-4454 or PTA-4803, deposited on Jun. 12, 2002 and Nov. 14, 2002, respectively; (i) a nucleotide sequence complimentary to any of the nucleotide sequences in (a), (b), (c), (d), (e), (f), (g), or (h), above.

The present invention is also directed to polynucleotide sequences which comprise, or alternatively consist of, a polynucleotide sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above.

Polynucleotides encoded by these nucleic acid molecules are also encompassed by the invention. In another embodiment, the invention encompasses nucleic acid molecule which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides. The present invention encompasses polypeptide sequences which comprise, or alternatively consist of, an amino acid sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, the following non-limited examples, the polypeptide sequence identified as SEQ ID NO:2, the polypeptide sequence encoded by a cDNA provided in at least one deposited clone, and/or polypeptide fragments of any of the polypeptides provided herein. Polynucleotides encoded by these nucleic acid molecules are also encompassed by the invention. In another embodiment, the invention encompasses nucleic acid molecule which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

The present invention is also directed to polypeptides which comprise, or alternatively consist of, an amino acid sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, the polypeptide sequence shown in SEQ ID NO:2, a polypeptide sequence encoded by the nucleotide sequence in SEQ ID NO:1, a polypeptide sequence encoded by a cDNA in one of ATCC Deposit Numbers PTA-4454 or PTA-4803, deposited on Jun. 12, 2002 and Nov. 14, 2002, respectively, and/or polypeptide fragments of any of these polypeptides (e.g., those fragments described herein). Polynucleotides which hybridize to the complement of the nucleic acid molecules encoding these polypeptides under stringent hybridization conditions or alternatively, under lower stringency conditions, are also encompasses by the present invention, as are the polypeptides encoded by these polynucleotides.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

As a practical matter, whether any particular nucleic acid molecule or polypeptide is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673-4680, (1994)), which is based on the algorithm of Higgins, D. G., et al., Computer Applications in the Biosciences (CABIOS), 8(2):189-191, (1992). In a sequence alignment the query and subject sequences are both DNA sequences. An RNA sequence can be compared by converting U's to T's. However, the CLUSTALW algorithm automatically converts U's to T's when comparing RNA sequences to DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps: Off; Hydrophilic Residue Gap=Off; and Transition Weighting=0. The pairwise and multiple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of 5' or 3' deletions, not because of internal deletions. If only the local pairwise percent identity is required, no manual correction is needed. However, a manual correction may be applied to determine the global percent identity from a global polynucleotide alignment. Percent identity calculations based upon global polynucleotide alignments are often preferred since they reflect the percent identity between the polynucleotide molecules as a whole (i.e., including any polynucleotide overhangs, not just overlapping regions), as opposed to, only local matching polynucleotides. Manual corrections for global percent identity determinations are required since the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score may be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by CLUSTALW is not manually corrected. Once again, only bases 5' and 3' of the subject sequence which are not matched/aligned with the query sequence are manually corrected for. No other manual corrections are required for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for instance, the amino acid sequence set forth in SEQ ID NO:2 or to the amino acid sequence encoded by cDNA contained in at least one deposited clone, can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., *Nucleic Acids Research,* 2(22):4673-4680, (1994)), which is based on the algorithm of Higgins, D. G., et al., *Computer Applications in the Biosciences* (CABIOS), 8(2):189-191, (1992). In a sequence alignment the query and subject sequences are both amino acid sequences. The result of said global sequence alignment is in percent identity. Preferred parameters used in a CLUSTALW alignment of DNA sequences to calculate percent identity via pairwise alignments are: Matrix=BLOSUM, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps:Off; Hydrophilic Residue Gap=Off; and Transition Weighting=0. The pairwise and multiple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of N- or C-terminal deletions, not because of internal deletions. If only the local pairwise percent identity is required, no manual correction is needed. However, a manual correction may be applied to determine the global percent identity from a global polypeptide alignment. Percent identity calculations based upon global polypeptide alignments are often preferred since they reflect the percent identity between the polypeptide molecules as a whole (i.e., including any polypeptide overhangs, not just overlapping regions), as opposed to, only local matching polypeptides. Manual corrections for global percent identity determinations are required since the CLUSTALW program does not account for N- and C-terminal truncations of the subject sequence when calculating percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the CLUSTALW sequence alignment. This percentage is then subtracted from the percent identity, calculated by the above CLUSTALW program using the specified parameters, to arrive at a final percent identity score. This final percent identity score is what may be used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the CLUSTALW alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the CLUSTALW program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence, which are not matched/aligned with the query. In this case the percent identity calculated by CLUSTALW is not manually corrected. Once again, only residue positions outside the N- and C-terminal ends of the subject sequence, as displayed in the CLUSTALW alignment, which are not matched/aligned with the query sequence are manually corrected for. No other manual corrections are required for the purposes of the present invention.

In addition to the above method of aligning two or more polynucleotide or polypeptide sequences to arrive at a percent identity value for the aligned sequences, it may be desirable in some circumstances to use a modified version of the CLUSTALW algorithm which takes into account known structural features of the sequences to be aligned, such as for example, the SWISS-PROT designations for each sequence. The result of such a modified CLUSTALW algorithm may provide a more accurate value of the percent identity for two polynucleotide or polypeptide sequences. Support for such a modified version of CLUSTALW is provided within the CLUSTALW algorithm and would be readily appreciated to one of skill in the art of bioinformatics.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred. Polynucleotide variants can be produced for a variety of reasons, e.g., to optimize codon expression for a particular host (change codons in the mRNA to those preferred by a bacterial host such as *E. coli*).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the protein without substantial loss of biological function. The authors of Ron et al., *J. Biol. Chem*. 268: 2984-2988 (1993), reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein (Dobeli et al., (1988) *J. Biotechnology* 7:199-216).

Moreover, ample evidence demonstrates that variants often retain a biological activity similar to that of the naturally occurring protein. For example, Gayle and coworkers (*J. Biol. Chem*. (1993) 268:22105-22111) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the protein will likely be retained when less than the majority of the residues of the protein are removed from the N-terminus or C-terminus. Whether a particular polypeptide lacking N- or C-terminal residues of a protein retains such immunogenic activities can readily be determined by routine methods described herein and otherwise known in the art.

Alternatively, such N-terminus or C-terminus deletions of a polypeptide of the present invention may, in fact, result in a significant increase in one or more of the biological activities of the polypeptide(s). For example, biological activity of many polypeptides are governed by the presence of regulatory domains at either one or both termini. Such regulatory domains effectively inhibit the biological activity of such polypeptides in lieu of an activation event (e.g., binding to a cognate ligand or receptor, phosphorylation, proteolytic processing, etc.). Thus, by eliminating the regulatory domain of a polypeptide, the polypeptide may effectively be rendered biologically active in the absence of an activation event.

Thus, the invention further includes polypeptide variants that show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., *Science* 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, *Science* 244:1081-1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved.

The invention encompasses polypeptides having a lower degree of identity but having sufficient similarity so as to perform one or more of the same functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al above, such conservative substitutions are likely to be phenotypically silent. Additional guidance concerning which amino acid changes are likely to be phenotypically silent are found in Bowie et al., *Science* 247:1306-1310 (1990).

Tolerated conservative amino acid substitutions of the present invention involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

In addition, the present invention also encompasses the conservative substitutions provided in Table II below.

TABLE II

Conservative Amino Acid Substitutions

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Aside from the uses described above, such amino acid substitutions may also increase protein or peptide stability. The invention encompasses amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., β or γ amino acids.

Both identity and similarity can be readily calculated by reference to the following publications: Computational Molecular Biology, Lesk, A. M., ed., Oxford University Press, New York, 1988; Biocomputing: Informatics and Genome Projects, Smith, D. W., ed., Academic Press, New York, 1993; Informatics Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991.

In addition, the present invention also encompasses substitution of amino acids based upon the probability of an amino acid substitution resulting in conservation of function. Such probabilities are determined by aligning multiple genes with related function and assessing the relative penalty of each substitution to proper gene function. Such probabilities are often described in a matrix and are used by some algorithms (e.g., BLAST, CLUSTALW, GAP, etc.) in calculating percent similarity wherein similarity refers to the degree by which one amino acid may substitute for another amino acid without lose of function. An example of such a matrix is the PAM250 or BLOSUM62 matrix.

Aside from the canonical chemically conservative substitutions referenced above, the invention also encompasses substitutions which are typically not classified as conservative, but that may be chemically conservative under certain circumstances. Analysis of enzymatic catalysis for proteases, for example, has shown that certain amino acids within the active site of some enzymes may have highly perturbed pKa's due to the unique microenvironment of the active site. Such perturbed pKa's could enable some amino acids to substitute for other amino acids while conserving enzymatic structure and function. Examples of amino acids that are known to have amino acids with perturbed pKa's are the Glu-35 residue of Lysozyme, the Ile-16 residue of Chymotrypsin, the His-159 residue of Papain, etc. The conservation of function relates to either anomalous protonation or anomalous deprotonation of such amino acids, relative to their canonical, non-perturbed pKa. The pKa perturbation may enable these amino acids to actively participate in general acid-base catalysis due to the unique ionization environment within the enzyme active site. Thus, substituting an amino acid capable of serving as either a general acid or general base within the microenvironment of an enzyme active site or cavity, as may be the case, in the same or similar capacity as the wild-type amino acid, would effectively serve as a conservative amino substitution.

Besides conservative amino acid substitution, variants of the present invention include, but are not limited to, the following: (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., (1967) *Clin. Exp. Immunol.* 2:331-340) Robbins et al., (1987) *Diabetes* 36: 838-845; Cleland et al., (1993) *Crit. Rev. Therapeutic Drug Carrier Systems* 10:307-377).

Moreover, the invention further includes polypeptide variants created through the application of molecular evolution ("DNA Shuffling") methodology to the polynucleotide disclosed as SEQ ID NO:1, the sequence of the clone submitted in a deposit, and/or the cDNA encoding the polypeptide disclosed as SEQ ID NO:2. Such DNA Shuffling technology is known in the art.

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1-5,5-10, 5-25, 5-50, 10-50 or 50-150, conservative amino acid substitutions are preferable.

The present invention is directed to polynucleotide fragments of the polynucleotides of the invention, in addition to polypeptides encoded therein by said polynucleotides and/or fragments.

In the present invention, a "polynucleotide fragment" refers to a short polynucleotide having a nucleic acid sequence which: is a portion of that contained in at least one deposited clone, or encoding the polypeptide encoded by the cDNA in at least one deposited clone; is a portion of that shown in SEQ ID NO:1 or the complementary strand thereto, or is a portion of a polynucleotide sequence encoding the polypeptide of SEQ ID NO:2. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the cDNA sequence contained in at least one deposited clone or the nucleotide sequence shown in SEQ ID NO:1. In this context "about" includes the particularly recited value, a value larger or smaller by several (5, 4, 3, 2, or 1) nucleotides, at either terminus, or at both termini. These nucleotide fragments have uses that include, but are not limited to, as diagnostic probes and primers as discussed herein. Of course, larger fragments (e.g., 50, 150, 500, 600, 2000 nucleotides) are preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:2 falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

In a preferred embodiment, the functional activity displayed by a polypeptide encoded by a polynucleotide fragment of the invention may be one or more biological activities typically associated with the full-length polypeptide of the invention. Illustrative of these biological activities includes the fragments ability to bind to at least one of the same antibodies which bind to the full-length protein, the fragments ability to interact with at lease one of the same proteins which bind to the full-length, the fragments ability to elicit at least one of the same immune responses as the full-length protein (i.e., to cause the immune system to create antibodies specific to the same epitope, etc.), the fragments ability to bind to at least one of the same polynucleotides as the full-length protein, the fragments ability to bind to a receptor of the full-length protein, the fragments ability to bind to a ligand of the full-length protein, and the fragments ability to multimerize with the full-length protein. However, the skilled artisan would appreciate that some fragments may have biological activities which are desirable and directly inapposite to the biological activity of the full-length protein. The functional activity of polypeptides of the invention, including fragments, variants, derivatives, and analogs thereof can be determined by numerous methods available to the skilled artisan, some of which are described elsewhere herein.

The present invention encompasses polypeptides comprising, or alternatively consisting of, an epitope of the polypeptide having an amino acid sequence of SEQ ID NO:2, or an epitope of a polypeptide sequence encoded by a polynucleotide sequence contained in one of ATCC Deposit Numbers PTA-4454 or PTA-4803, deposited on Jun. 12, 2002 and Nov. 14, 2002, respectively, or encoded by a polynucleotide that hybridizes to the complement of the sequence of SEQ ID NO:1 or contained in one of ATCC Deposit Numbers PTA-4454 or PTA-4803, deposited on Jun. 12, 2002 and Nov. 14, 2002, respectively, under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., *Proc. Natl. Acad. Sci.* USA 81:3998-4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross reactivity with other antigens. Antigenic epitopes need not necessarily be immunogenic.

Fragments which function as epitopes may be produced by any conventional means. (See, e.g., Houghten, *Proc. Natl. Acad. Sci.* USA 82:5131-5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length, or longer. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., *Cell* 37:767-778 (1984); Sutcliffe et al., *Science* 219:660-666 (1983)).

Similarly, immunogenic epitopes can be used, for example, to induce antibodies according to methods well known in the art. (See, for instance, Sutcliffe et al., supra; Wilson et al., supra; Chow et al., *Proc. Natl. Acad. Sci.* USA 82:910-914; and Bittle et al., *J. Gen. Virol.* 66:2347-2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., *J. Gen. Virol.*, 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl N-hydroxysuccinimide ester (MBS), while other peptides may be coupled to carriers using a more general linking agent such as glutaraldehyde. Animals such as rabbits, rats and mice are immunized with either free or carrier coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase halflife in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., *Nature*, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., *J. Biochem.*, 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, *Proc. Natl. Acad. Sci.* USA 88:8972-897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605, 793; 5,811,238; 5,830,721; 5,834,252; and 5,837,458, and Patten et al., *Curr. Opinion Biotechnol.* 8:724-33 (1997); Harayama, *Trends Biotechnol.* 16(2):76-82 (1998); Hansson, et al., *J. Mol. Biol.* 287:265-76 (1999); and Lorenzo and Blasco, *Biotechniques* 24(2):308-13 (1998) (each of these patents and publications are hereby incorporated by reference in its entirety). In one embodiment, alteration of polynucleotides corresponding to SEQ ID NO:1 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Further polypeptides of the invention relate to antibodies and T-cell antigen receptors (TCR) which immunospecifically bind a polypeptide, polypeptide fragment, or variant of SEQ ID NO:2, and/or an epitope, of the present invention (as determined by immunoassays well known in the art for assaying specific antibody-antigen binding). Antibodies of the invention include, but are not limited to, polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) is meant to include intact molecules, as well as, antibody fragments (such as, for example, Fab and F(ab')2 fragments) which are capable of specifically binding to protein. Fab and F(ab')2 fragments lack the Fc fragment of intact antibody, clear more rapidly from the circulation of the animal or plant, and may have less non-specific tissue binding than an intact antibody (Wahl et al., J. Nucl. Med. 24:316-325 (1983)). Thus, these fragments are preferred, as well as the products of a FAB or other immunoglobulin expression library. Moreover, antibodies of the present invention include chimeric, single chain, and humanized antibodies.

Most preferably the antibodies are human antigen-binding antibody fragments of the present invention and include, but are not limited to, Fab, Fab' and F(ab')$_2$, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homologue of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologues of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10$-2 M, $10$-2 M, $5\times10$-3 M, $10$-3 M, $5\times10$-4 M, $10$-4 M, $5\times10$-5 M, $10$-5 M, $5\times10$-6 M, $10$-6M, $5\times10$-7 M, $10$7 M, $5\times10$-8 M, $10$-8 M, $5\times10$-9 M, $10$-9 M, $5\times10$-10 M, $10$-10 M, $5\times10$-11 M, $10$-11 M, $5\times10$-12 M, $10$-12 M, $5\times10$-13 M, $10$-13 M, $5\times10$-14 M, $10$-14 M, $5\times10$-15 M, or $10$-15 M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., *Blood* 92(6):1981-1988 (1998); Chen et al., *Cancer Res.* 58(16):3668-3678 (1998); Harrop et al., *J. Immunol.* 161 (4):1786-1794 (1998); Zhu al., *Cancer Res.* 58(15):3209-3214 (1998); Yoon et al., *J. Immunol.* 160(7):3170-3179 (1998); Prat et al., *J. Cell. Sci.* 111(Pt2):237-247 (1998); Pitard et al., *J. Immunol. Methods* 205(2):177-190 (1997); Liautard et al., *Ctokine* 9(4):233-241 (1997); Carlson et al., *J. Biol. Chem.* 272(17): 11295-11301 (1997); Taryman et al., *Neuron* 14(4):755-762 (1995); Muller et al., *Structure* 6(9): 1153-1167 (1998); Bartunek et al., *Cytokine* 8(1):14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art.

The antibodies of the present invention may comprise polyclonal antibodies. Methods of preparing polyclonal antibodies are known to the skilled artisan (Harlow, et al., Antibodies: A Laboratory Manual, (Cold spring Harbor Laboratory Press, $2^{nd}$ ed. (1988); and Current Protocols, Chapter 2; which are hereby incorporated herein by reference in its entirety). In a preferred method, a preparation of the MGAT3 protein is prepared and purified to render it substantially free of natural contaminants. Such a preparation is then introduced into an animal in order to produce polyclonal antisera of greater specific activity. For example, a polypeptide of the invention can be administered to various host animals including, but not limited to, rabbits, mice, rats, etc. to induce the production of sera containing polyclonal antibodies specific for the antigen. The administration of the polypeptides of the present invention may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. For the purposes of the invention, "immunizing agent" may be defined as a polypeptide of the invention, including fragments, variants, and/or derivatives thereof, in addition to fusions with heterologous polypeptides and other forms of the polypeptides described herein.

Typically, the immunizing agent and/or adjuvant will be injected in the mammal by multiple subcutaneous or intraperitoneal injections, though they may also be given intramuscularly, and/or through IV). The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivitizing active chemical functional groups to both the polypeptide of the present invention and the immunogenic protein such that a covalent bond is formed, or through fusion-protein based methodology, or other methods known to the skilled artisan. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present invention may comprise monoclonal antibodies. Monoclonal antibodies may be prepared using hybridoma methods, such as those described by Kohler and Milstein, *Nature*, 256:495 (1975) and U.S. Pat. No. 4,376,110, by Harlow, et al., Antibodies: A Laboratory Manual, (Cold spring Harbor Laboratory Press, $2^{nd}$ ed. (1988), by Hammerling, et al., Monoclonal Antibodies and T-Cell Hybridomas (Elsevier, N.Y., pp. 563-681 (1981); Köhler et al., *Eur. J. Immunol.* 6:511 (1976); Köhler et al., *Eur. J. Immunol.* 6:292 (1976), or other methods known to the artisan. Other examples of methods which may be employed for producing monoclonal antibodies includes, but are not limited to, the human B-cell hybridoma technique (Kosbor et al., 1983, *Immunology Today* 4:72; Cole et al., 1983, *Proc. Natl. Acad. Sci.* USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include polypeptides of the present invention or a fusion protein thereof. Preferably, the immunizing agent consists of an MGAT3 polypeptide or, more preferably, with a MGAT3 polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. More preferred are the parent myeloma cell line (SP20) as provided by the ATCC. As inferred throughout the specification, human myeloma and mouse-human heteromyeloma cell lines also have been described for the production of human monoclonal antibodies (Kozbor, *J. Immunol.*, 133:3001 (1984); Brodeur et al., Monoclonal Antibody Production Techniques and Applications, Marcel Dekker, Inc., New York, (1987) pp. 51-63).

The culture medium in which the hybridoma cells are cultured can then be assayed for the presence of monoclonal antibodies directed against the polypeptides of the present invention. Preferably, the binding specificity of monoclonal antibodies produced by the hybridoma cells is determined by immunoprecipitation or by an in vitro binding assay, such as radioimmunoassay (RIA) or enzyme-linked immunoabsorbant assay (ELISA). Such techniques are known in the art and within the skill of the artisan. The binding affinity of the monoclonal antibody can, for example, be determined by the Scatchard analysis of Munson and Pollart, Anal. Biochem., 107:220 (1980).

After the desired hybridoma cells are identified, the clones may be subcloned by limiting dilution procedures and grown by standard methods (Goding, supra, and/or according to Wands et al. (Gastroenteroloy 80:225-232 (1981)). Suitable culture media for this purpose include, for example, Dulbecco's Modified Eagle's Medium and RPM1-1640. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hydridomas. For example, the monoclonal antibodies may be made by recombinant DNA methods, such as those described in U.S. Pat. No. 4, 816, 567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). The hybridoma cells of the invention serve as a preferred source of such DNA. Once isolated, the DNA may be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples described herein. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., Gene 187 9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., *BioTechniques* 12(6):864-869 (1992); and Sawai et al., AJRI 34:26-34 (1995); and Better et al., *Science* 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., Science 240:1038-1040 (1988).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, *Science* 229:1202 (1985); Oi et al., *BioTechniques* 4:214 (1986); Gillies et al., (1989) *J. Immunol. Methods* 125:191-202; Cabilly et al., Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985); U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28(4/5):489-498 (1991); Studnicka et al., *Protein Engineering* 7(6):805-814 (1994); Roguska. et al., *PNAS* 91:969-973 (1994)), and chain shuffling (U.S. Pat. No. 5,565,332). Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., *Nature*, 321:522-525 (1986); Reichmann et al., *Nature*, 332:323-327 (1988); Verhoeyen et al., *Science*, 239:1534-1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., *Nature*, 321:522-525 (1986); Riechmann et al., *Nature* 332:323-329 (1988)1 and Presta, *Curr. Op. Struct. Biol.*, 2:593-596 (1992).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. The techniques of Cole et al., and Boerder et al., are also available for the preparation of human monoclonal antibodies (Cole et al., Monoclonal Antibodies and Cancer Therapy, Alan R. Riss, (1985); and Boerner et al. *J. Immunol.*, 147(1):86-95, (1991)).

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and creation of an antibody repertoire. This approach is described, for example, in U.S. Pat. Nos. 5,545,807; 5,545,806; 5,569,825; 5,625,126; 5,633,425; 5,661,106, and in the following scientific publications: Marks et al., *Biotechnol.*, 10:779-783 (1992); Lonberg et al., *Nature* 368:856-859 (1994); Fishwild et al., *Nature Biotechnol.*, 14:845-51 (1996); Neuberger, *Nature Biotechnol.*, 14:826 (1996); Lonberg and Huszer, *Intern. Rev. Immunol.*, 13:65-93 (1995).

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/technology* 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, *FASEB J.* 7(5):437-444; (1989) and Nissinoff, *J. Immunol.* 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Such anti-idiotypic antibodies capable of binding to the MGAT3 polypeptide can be produced in a two-step procedure. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

The antibodies of the present invention may be bispecific antibodies. Bispecific antibodies are monoclonal, Preferably human or humanized, antibodies that have binding specificities for at least two different antigens. In the present invention, one of the binding specificities may be directed towards a polypeptide of the present invention, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, *Nature*, 305:537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh et al., *Meth. In Enzym.*, 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980), and for the treatment of HIV infection (WO 91/00360; WO 92/20373; and EP03089). It is contemplated that the antibodies may be prepared in vitro using known methods in synthetic protein chemistry, including those involving crosslinking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., *BioTechniques* 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242:1038-1041 (1988)).

More preferably, a clone encoding an antibody of the present invention may be obtained according to the method described in the Example section herein.

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., E. coli, B. subtilis) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., *EMBO J.* 2:1791 (1983)), in which the antibody coding sequence may be ligated individually into the vector in frame with the lac Z coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non essential region of the viral genome (e.g., region E1 or E3) will result in a recombinant virus that is viable and capable of expressing the antibody molecule in infected hosts. (e.g., see Logan & Shenk, *Proc. Natl. Acad. Sci.* USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci.* USA 48:202 (1992)), and adenine phosphoribosyltransferase (Lowy et al., *Cell* 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., *Natl. Acad. Sci.* USA 77:357 (1980); O'Hare et al., *Proc. Natl. Acad. Sci.* USA 78:1527 (1981)); gpt, which confers resistance to mycophenolic acid (Mulligan & Berg, *Proc. Natl. Acad. Sci.* USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, *Science* 260: 926-932 (1993); and Morgan and Anderson, *Ann. Rev. Biochem.* 62:191-217 (1993); May, 1993, TIB TECH 11(5):

155-215); and hygro, which confers resistance to hygromycin (Santerre et al., *Gene* 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., *J. Mol. Biol.* 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, *Nature* 322:52 (1986); Kohler, *Proc. Natl. Acad. Sci.* USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., *Immunol. Lett.* 39:91-99 (1994); U.S. Pat. No. 5,474,981; Gillies et al., *PNAS* 89:1428-1432 (1992); Fell et al., *J. Immunol.* 146:2446-2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., *Proc. Natl. Acad. Sci.* USA 88:10535-10539 (1991); Zheng et al., *J. Immunol.* 154:5590-5600 (1995); and Vil et al., *Proc. Natl. Acad. Sci.* USA 89:11337-11341(1992) (said references incorporated by reference in their entireties).

As discussed, supra, the polypeptides corresponding to a polypeptide, polypeptide fragment, or a variant of SEQ ID NO:2 may be fused or conjugated to the above antibody portions to increase the in vivo half life of the polypeptides or for use in immunoassays using methods known in the art. Further, the polypeptides corresponding to SEQ ID NO:2 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., *Nature* 331:84-86 (1988). The polypeptides of the present invention fused or conjugated to an antibody having disulfide linked dimeric structures (due to the IgG) may also be more efficient in binding and neutralizing other molecules, than the monomeric secreted protein or protein fragment alone. (Fountoulakis et al., *J. Biochem.* 270:3958-3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., *J. Molecular Recognition* 8:52-58 (1995); Johanson et al., *J. Biol. Chem.* 270:9459-9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci.* USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., *Int. Immunol.*, 6:1567-1574 (1994)), VEGI (See, International Publication No. WO 99/23105), a thrombotic agent or an anti angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

The present invention also encompasses the creation of synthetic antibodies directed against the polypeptides of the present invention. One example of synthetic antibodies is described in Radrizzani, M., et al., *Medicina*, (Aires), 59(6): 753-8, (1999)). Recently, a new class of synthetic antibodies has been described and are referred to as molecularly imprinted polymers (MIPs) (Semorex, Inc.). Antibodies, peptides, and enzymes are often used as molecular recognition elements in chemical and biological sensors. However, their lack of stability and signal transduction mechanisms limits their use as sensing devices. Molecularly imprinted polymers (MIPs) are capable of mimicking the function of biological receptors but with less stability constraints. Such polymers provide high sensitivity and selectivity while maintaining excellent thermal and mechanical stability. MIPs have the ability to bind to small molecules and to target molecules such as organics and proteins' with equal or greater potency than that of natural antibodies.

These "super" MIPs have higher affinities for their target and thus require lower concentrations for efficacious binding.

During synthesis, the MIPs are imprinted so as to have complementary size, shape, charge and functional groups of the selected target by using the target molecule itself (such as a polypeptide, antibody, etc.), or a substance having a very similar structure, as its "print" or "template." MIPs can be derivatized with the same reagents afforded to antibodies. For example, fluorescent 'super' MIPs can be coated onto beads or wells for use in highly sensitive separations or assays, or for use in high throughput screening of proteins.

Moreover, MIPs based upon the structure of the polypeptide(s) of the present invention may be useful in screening for compounds that bind to the polypeptide(s) of the invention. Such a MIP would serve the role of a synthetic "receptor" by mimicking the native architecture of the polypeptide. In fact, the ability of a MIP to serve the role of a synthetic receptor has already been demonstrated for the estrogen receptor (Ye, L., Yu, Y., Mosbach, K, *Analyst.*, 126(6):760-5, (2001); Dickert, F, L., Hayden, O., Halikias, K, P, *Analyst.*, 126(6):766-71, (2001)). A synthetic receptor may either be mimicked in its entirety (e.g., as the entire protein), or mimicked as a series of short peptides corresponding to the protein (Rachkov, A., Minoura, N, *Biochim Biophys, Acta.*, 1544(1-2):255-66, (2001)). Such a synthetic receptor MIPs may be employed in any one or more of the screening methods described elsewhere herein.

MIPs have also been shown to be useful in "sensing" the presence of its mimicked molecule (Cheng, Z., Wang, E., Yang, X, *Biosens, Bioelectron.*, 16(3):179-85, (2001); Jenkins, A, L., Yin, R., Jensen, J. L, *Analyst.*, 126(6):798-802, (2001); Jenkins, A, L., Yin, R., Jensen, J. L, *Analyst.*, 126(6):798-802, (2001)). For example, a MIP designed using a polypeptide of the present invention may be used in assays designed to identify, and potentially quantitate, the level of said polypeptide in a sample. Such a MIP may be used as a substitute for any component described in the assays, or kits, provided herein (e.g., ELISA, etc.).

A number of methods may be employed to create MIPs to a specific receptor, ligand, polypeptide, peptide, organic molecule. Several preferred methods are described by Esteban et al in *J. Anal, Chem.*, 370(7):795-802, (2001), which is hereby incorporated herein by reference in its entirety in addition to any references cited therein. Additional methods are known in the art and are encompassed by the present invention, such as for example, Hart, B, R., Shea, K, J. *J. Am. Chem, Soc.*, 123(9):2072-3, (2001); and Quaglia, M., Chenon, K., Hall, A, J., De, Lorenzi, E., Sellergren, B, *J. Am. Chem, Soc.*, 123(10):2146-54, (2001); which are hereby incorporated by reference in their entirety herein.

Antibodies of the present invention have various utilities. For example, such antibodies may be used in diagnostic assays to detect the presence or quantification of the polypeptides of the invention in a sample. Such a diagnostic assay may be comprised of at least two steps. The first, subjecting a sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (e.g., See Arenkov P, et al., *Anal Biochem.*, 278(2):123-131 (2000)), or a chromatography column, etc. And a second step involving the quantification of antibody bound to the substrate. Alternatively, the method may additionally involve a first step of attaching the antibody, either covalently, electrostatically, or reversibly, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp147-158). The antibodies used in the diagnostic assays can be labeled with a detectable moiety. The detectable moiety should be capable of producing, either directly or indirectly, a detectable signal. For example, the detectable moiety may be a radioisotope, such as $^2H$, $^{14}C$, $^{32}P$, or $^{125}I$, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., Nature, 144:945 (1962); Dafvid et al., Biochem., 13:1014 (1974); Pain et al., J. Immunol. Metho., 40:219(1981); and Nygren, J. Histochem. And Cytochem., 30:407 (1982).

Antibodies directed against the polypeptides of the present invention are useful for the affinity purification of such polypeptides from recombinant cell culture or natural sources. In this process, the antibodies against a particular polypeptide are immobilized on a suitable support, such as a Sephadex resin or filter paper, using methods well known in the art. The immobilized antibody then is contacted with a sample containing the polypeptides to be purified, and thereafter the support is washed with a suitable solvent that will remove substantially all the material in the sample except for the desired polypeptides, which are bound to the immobilized antibody. Finally, the support is washed with another suitable solvent that will release the desired polypeptide from the antibody.

Antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell*, 96:737-49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Antibodies directed against polypeptides of the present invention are useful for inhibiting allergic reactions in animals. For example, by administering a therapeutically acceptable dose of an antibody, or antibodies, of the present invention, or a cocktail of the present antibodies, or in combination with other antibodies of varying sources, the animal may not elicit an allergic response to antigens.

Likewise, one could envision cloning the gene encoding an antibody directed against a polypeptide of the present invention, said polypeptide having the potential to elicit an allergic and/or immune response in an organism, and transforming the organism with said antibody gene such that it is expressed (e.g., constitutively, inducibly, etc.) in the organism. Thus, the organism would effectively become resistant to an allergic response resulting from the ingestion or presence of such an immune/allergic reactive polypeptide. Moreover, such a use of the antibodies of the present invention may have particular utility in preventing and/or ameliorating autoimmune diseases and/or disorders, as such conditions are typically a result of antibodies being directed against endogenous proteins. For example, in the instance where the polypeptide of the present invention is responsible for modulating the immune response to auto-antigens, transforming the organism and/or individual with a construct comprising any of the promoters disclosed herein or otherwise known in the art, in addition, to a polynucleotide encoding the antibody directed against the polypeptide of the present invention could effective inhibit the organisms immune system from eliciting an immune response to the auto-antigen(s). Detailed descriptions of therapeutic and/or gene therapy applications of the present invention are provided elsewhere herein.

Alternatively, antibodies of the present invention could be produced in a plant (e.g., cloning the gene of the antibody directed against a polypeptide of the present invention, and transforming a plant with a suitable vector comprising said gene for constitutive expression of the antibody within the plant), and the plant subsequently ingested by an animal, thereby conferring temporary immunity to the animal for the specific antigen the antibody is directed towards (See, for example, U.S. Pat. Nos. 5,914,123 and 6,034,298).

In another embodiment, antibodies of the present invention, preferably polyclonal antibodies, more preferably monoclonal antibodies, and most preferably single-chain antibodies, can be used as a means of inhibiting gene expression of a particular gene, or genes, in a human, mammal, and/or other organism. See, for example, International Publication Number WO 00/05391, published Feb. 3, 2000, to Dow Agrosciences LLC. The application of such methods for the antibodies of the present invention are known in the art, and are more particularly described elsewhere herein.

In yet another embodiment, antibodies of the present invention may be useful for multimerizing the polypeptides of the present invention. For example, certain proteins may confer enhanced biological activity when present in a multimeric state (i.e., such enhanced activity may be due to the increased effective concentration of such proteins whereby more protein is available in a localized location).

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, *Proc. Natl. Acad. Sci. USA* 86:8932-8935 (1989); Zijlstra et al., *Nature* 342:435-438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, *J. Biol. Chem.* 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, *Proc. Natl. Acad. Sci.* USA 86:8932-8935 (1989); Zijlstra et al., Nature 342:435-438 (1989)).

In a specific embodiment, viral vectors that contains nucleic acid sequences encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., *J. Clin. Invest.* 93:644-651 (1994); Kiem et al., *Blood* 83:1467-1473 (1994); Salmons and Gunzberg, *Human Gene Therapy* 4:129-141 (1993); and Grossman and Wilson, *Curr. Opin. in Genetics and Devel.* 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499-503 (1993) present a review of adenovirus-based gene therapy. Bout et al., *Human Gene Therapy* 5:3-10 (1994) demonstrated the use of adenovirus vectors to transfer genes to the respiratory epithelia of rhesus monkeys. Other instances of the use of adenoviruses in gene therapy can be found in Rosenfeld et al., *Science* 252:431-434 (1991); Rosenfeld et al., *Cell* 68:143-155 (1992); Mastrangeli et al., *J. Clin. Invest.* 91:225-234 (1993); PCT Publication WO94/12649; and Wang, et al., Gene Therapy 2:775-783 (1995). In a preferred embodiment, adenovirus vectors are used.

Adeno-associated virus (AAV) has also been proposed for use in gene therapy (Walsh et al., *Proc. Soc. Exp. Biol. Med.* 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, *Meth. Enzymol.* 217:599-618 (1993); Cohen et al., *Meth. Enzymol.* 217:618-644 (1993); Cline, *Pharmac. Ther.* 29:69-92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, *Cell* 71:973-985 (1992); Rheinwald, *Meth. Cell Bio.* 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

The invention provides methods of treatment, inhibition and prophylaxis by administration to a subject of an effective amount of a compound or pharmaceutical composition of the invention, such as an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, *J. Biol. Chem.* 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, *Science* 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC *Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., *Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (*Science* 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., *Proc. Natl. Acad. Sci.* USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging with Antibodies

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., *J. Cell. Biol.* 101:976-985 (1985); Jalkanen, et al., *J. Cell. Biol.* 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($125I$, $121I$), carbon ($14C$), sulfur ($35S$), tritium ($3H$), indium ($112In$), and technetium ($99Tc$); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface bound recombinant antigens, and a reporter-labeled anti-human antibody for detecting surface-bound anti-antigen antibody.

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because certain proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Peptide moieties may be added to the polypeptide to facilitate purification. Such regions may be removed prior to final preparation of the polypeptide. Similarly, peptide cleavage sites can be introduced in-between such peptide moieties, which could additionally be subjected to protease activity to remove said peptide(s) from the protein of the present invention. The addition of peptide moieties, including peptide cleavage sites, to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., *Nature* 331: 84-86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958-3964 (1995).)

Similarly, EP-A-O 464 533 (Canadian counterpart 2045869) discloses fusion proteins comprising various portions of the constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., *J. Molecular Recognition* 8:52-58 (1995); K. Johanson et al., *J. Biol. Chem.* 270:9459-9471 (1995).)

Moreover, the polypeptides of the present invention can be fused to marker sequences (also referred to as "tags"). Due to the availability of antibodies specific to such "tags", purification of the fused polypeptide of the invention, and/or its identification is significantly facilitated since antibodies specific to the polypeptides of the invention are not required. Such purification may be in the form of an affinity purification whereby an anti-tag antibody or another type of affinity matrix (e.g., anti-tag antibody attached to the matrix of a flow-thru column) that binds to the epitope tag is present. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci.* USA 86:821-824 (1989), for instance, hexa-histidine provides for convenient purification of the fusion protein. Another peptide tag useful for purification, the "HA" tag, corresponds to an epitope derived from the influenza hemagglutinin protein. (Wilson et al., *Cell* 37:767 (1984)).

The skilled artisan would acknowledge the existence of other "tags" which could be readily substituted for the tags referred to supra for purification and/or identification of polypeptides of the present invention (Jones C., et al., *J Chromatogr A*. 707(1):3-22 (1995)). For example, the c-myc tag and the 8F9, 3C7, 6E10, G4m B7 and 9E10 antibodies thereto (Evan et al., *Molecular and Cellular Biology* 5:3610-3616 (1985)); the Herpes Simplex virus glycoprotein D (gD) tag and its antibody(Paborsky et al., *Protein Engineering*, 3(6):547-553 (1990), the Flag-peptide—i.e., the octapeptide sequence DYKDDDDK (SEQ ID NO:24), (Hopp et al., *Biotech*. 6:1204-1210 (1988); the KT3 epitope peptide (Martin et al., *Science*, 255:192-194 (1992)); a-tubulin epitope peptide (Skinner et al., *J. Biol. Chem*., 266:15136-15166, (1991)); the T7 gene 10 protein peptide tag (Lutz-Freyermuth et al., *Proc. Natl. Sci.* USA, 87:6363-6397 (1990)), the FITC epitope (Zymed, Inc.), the GFP epitope (Zymed, Inc.), and the Rhodamine epitope (Zymed, Inc.).

The present invention also encompasses the attachment of up to nine codons encoding a repeating series of up to nine arginine amino acids to the coding region of a polynucleotide of the present invention. The invention also encompasses chemically derivitizing a polypeptide of the present invention with a repeating series of up to nine arginine amino acids. Such a tag, when attached to a polypeptide, has recently been shown to serve as a universal pass, allowing compounds access to the interior of cells without additional derivitization or manipulation (Wender, P., et al., unpublished data).

Protein fusions involving polypeptides of the present invention, including fragments and/or variants thereof, can be used for the following, non-limiting examples, subcellular localization of proteins, determination of protein-protein interactions via immunoprecipitation, purification of proteins via affinity chromatography, functional and/or structural characterization of protein. The present invention also encompasses the application of hapten specific antibodies for any of the uses referenced above for epitope fusion proteins. For example, the polypeptides of the present invention could be chemically derivatized to attach hapten molecules (e.g., DNP, (Zymed, Inc.)). Due to the availability of monoclonal antibodies specific to such haptens, the protein could be readily purified using immunoprecipation, for example.

Polypeptides of the present invention, including fragments and/or variants thereof, in addition to, antibodies directed against such polypeptides, fragments, and/or variants, may be fused to any of a number of known, and yet to be determined, toxins, such as ricin, saporin (Mashiba H, et al., Ann. N.Y. Acad. Sci. 1999;886:233-5), or HC toxin (Tonukari N J, et al., Plant Cell. 2000 Feb. 12(2):237-248), for example. Such fusions could be used to deliver the toxins to desired tissues for which a ligand or a protein capable of binding to the polypeptides of the invention exists.

The invention encompasses the fusion of antibodies directed against polypeptides of the present invention, including variants and fragments thereof, to said toxins for delivering the toxin to specific locations in a cell, to specific tissues, and/or to specific species. Such bifunctional antibodies are known in the art, though a review describing additional advantageous fusions, including citations for methods of production, can be found in P. J. Hudson, Curr. Opp. In. Imm. 11:548-557, (1999); this publication, in addition to the references cited therein, are hereby incorporated by reference in their entirety herein. In this context, the term "toxin" may be expanded to include any heterologous protein, a small molecule, radionucleotides, cytotoxic drugs, liposomes, adhesion molecules, glycoproteins, ligands, cell or tissue-specific ligands, enzymes, of bioactive agents, biological response modifiers, anti-fungal agents, hormones, steroids, vitamins, peptides, peptide analogs, anti-allergenic agents, anti-tubercular agents, anti-viral agents, antibiotics, anti-protozoan agents, chelates, radioactive particles, radioactive ions, X-ray contrast agents, monoclonal antibodies, polyclonal antibodies and genetic material. In view of the present disclosure, one skilled in the art could determine whether any particular "toxin" could be used in the compounds of the present invention. Examples of suitable "toxins" listed above are exemplary only and are not intended to limit the "toxins" that may be used in the present invention.

Thus, any of these above fusions can be engineered using the polynucleotides or the polypeptides of the present invention.

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells (e.g., Saccharomyces cerevisiae or Pichia pastoris (ATCC Accession No. 201178)); insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PA0815 (all available from Invitrogen, Carlsbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast *Pichia pastoris* is used to express the polypeptide of the present invention in a eukaryotic system. *Pichia pastoris* is a methylotrophic yeast which can metabolize methanol as its sole carbon source. A main step in the methanol metabolization pathway is the oxidation of methanol to formaldehyde using $O_2$. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for $O_2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis, S. B., et al., *Mol. Cell. Biol*. 5:1111-21 (1985); Koutz, P. J, et al., *Yeast* 5:167-77 (1989); Tschopp, J. F., et al., *Nucl. Acids Res*. 15:3859-76 (1987). Thus, a heterologous coding sequence, such as, for example, a polynucleotide of the present invention, under the transcriptional regulation of all or part of the AOX1 regulatory sequence is expressed at exceptionally high levels in *Pichia* yeast grown in the presence of methanol.

In one example, the plasmid vector pPIC9K is used to express DNA encoding a polypeptide of the invention, as set forth herein, in a *Pichea* yeast system essentially as described in "*Pichia* Protocols: Methods in Molecular Biology," D. R. Higgins and J. Cregg, eds. The Humana Press, Totowa, N.J., 1998. This expression vector allows expression and secretion of a protein of the invention by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG, as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., *Proc. Natl. Acad. Sci*. USA 86:8932-8935 (1989); and Zijlstra et al., *Nature* 342:435-438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W. H. Freeman & Co., N.Y., and Hunkapiller et al., Nature, 310:105-111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, omithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein, the addition of epitope tagged peptide fragments (e.g., FLAG, HA, GST, thioredoxin, maltose binding protein, etc.), attachment of affinity tags such as biotin and/or streptavidin, the covalent attachment of chemical moieties to the amino acid backbone, N- or C-terminal processing of the polypeptides ends (e.g., proteolytic processing), deletion of the N-terminal methionine residue, etc.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The invention further encompasses chemical derivitization of the polypeptides of the present invention, preferably where the chemical is a hydrophilic polymer residue. Exemplary hydrophilic polymers, including derivatives, may be those that include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including the salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates.

The molecular weight of the hydrophilic polymers may vary, and is generally about 50 to about 5,000,000, with polymers having a molecular weight of about 100 to about 50,000 being preferred. The polymers may be branched or unbranched. More preferred polymers have a molecular weight of about 150 to about 10,000, with molecular weights of 200 to about 8,000 being even more preferred.

For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

Additional preferred polymers which may be used to derivatize polypeptides of the invention, include, for example, poly(ethylene glycol) (PEG), poly(vinylpyrrolidine), polyoxomers, polysorbate and poly(vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, will be readily apparent to one skilled in the art based on the present disclosure. Generally, the polymers used may include polymers that can be attached to the polypeptides of the invention via alkylation or acylation reactions.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As with the various polymers exemplified above, it is contemplated that the polymeric residues may contain functional groups in addition, for example, to those typically involved in linking the polymeric residues to the polypeptides of the present invention. Such functionalities include, for example, carboxyl, amine, hydroxy and thiol groups. These functional groups on the polymeric residues can be further reacted, if desired, with materials that are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins, and nucleosides.

In addition to residues of hydrophilic polymers, the chemical used to derivatize the polypeptides of the present invention can be a saccharide residue. Exemplary saccharides which can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure.

Generally, saccharides which may be used for derivitization include saccharides that can be attached to the polypeptides of the invention via alkylation or acylation reactions.

Moreover, the invention also encompasses derivitization of the polypeptides of the present invention, for example, with lipids (including cationic, anionic, polymerized, charged, synthetic, saturated, unsaturated, and any combination of the above, etc.). stabilizing agents.

The invention encompasses derivitization of the polypeptides of the present invention, for example, with compounds that may serve a stabilizing function (e.g., to increase the polypeptides half-life in solution, to make the polypeptides more water soluble, to increase the polypeptides hydrophilic or hydrophobic character, etc.). Polymers useful as stabilizing materials may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin, polyalginates, and polylactide-coglycolide polymers. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, hydroxyapatites, fluoroapatite polymers, polyethylenes (such as, for example, polyethylene glycol (including for example, the class of compounds referred to as Pluronics.RTM., commercially available from BASF, Parsippany, N.J.), polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of derivatized polypeptides of the invention which employ polymers as stabilizing compounds will be readily apparent to one skilled in the art, in view of the present disclosure, when coupled with information known in the art, such as that described and referred to in Unger, U.S. Pat. No. 5,205,290, the disclosure of which is hereby incorporated by reference herein in its entirety.

Moreover, the invention encompasses additional modifications of the polypeptides of the present invention. Such additional modifications are known in the art, and are specifically provided, in addition to methods of derivitization, etc., in U.S. Pat. No. 6,028,066, which is hereby incorporated in its entirety herein.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:2 or encoded by the cDNA contained in at least one deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by at least one deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, osteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (*FEBS Letters* 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide sequence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more intermolecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques into liposomes (see, e.g., U.S. Pat. No. 5,478,925, which is herein incorporated by reference in its entirety).

In addition, the polynucleotide insert of the present invention could be operatively linked to "artificial" or chimeric promoters and transcription factors. Specifically, the artificial promoter could comprise, or alternatively consist, of any combination of cis-acting DNA sequence elements that are recognized by trans-acting transcription factors. Preferably, the cis acting DNA sequence elements and trans-acting transcription factors are operable in mammals. Further, the trans-acting transcription factors of such "artificial" promoters could also be "artificial" or chimeric in design themselves and could act as activators or repressors to said "artificial" promoter.

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15-25 bp) from the sequences shown in SEQ ID NO:1. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:1 will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000-4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. Disease mapping data are known in the art. Assuming 1 megabase mapping resolution and one gene per 20 kb, a cDNA precisely localized to a chromosomal region associated with the disease could be one of 50-500 potential causative genes.

Thus, once coinheritance is established, differences in the polynucleotide and the corresponding gene between affected and unaffected organisms can be examined. First, visible structural alterations in the chromosomes, such as deletions or translocations, are examined in chromosome spreads or by PCR. If no structural alterations exist, the presence of point mutations are ascertained. Mutations observed in some or all affected organisms, but not in normal organisms, indicates that the mutation may cause the disease. However, complete sequencing of the polypeptide and the corresponding gene from several normal organisms is required to distinguish the mutation from a polymorphism. If a new polymorphism is identified, this polymorphic polypeptide can be used for further linkage analysis.

Furthermore, increased or decreased expression of the gene in affected organisms as compared to unaffected organisms can be assessed using polynucleotides of the present invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an organism and comparing the measured gene expression level with a standard level of polynucleotide expression level, whereby an increase or decrease in the gene expression level compared to the standard is indicative of a disorder.

By "measuring the expression level of a polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of organisms not having a disorder. As will be appreciated in the art, once a standard polypeptide level or mRNA level is known, it can be used repeatedly as a standard for comparison.

By "biological sample" is intended any biological sample obtained from an organism, body fluids, cell line, tissue culture, or other source which contains the polypeptide of the present invention or mRNA. As indicated, biological samples include body fluids (such as the following non-limiting examples, sputum, amniotic fluid, urine, saliva, breast milk, secretions, interstitial fluid, blood, serum, spinal fluid, etc.) which contain the polypeptide of the present invention, and other tissue sources found to express the polypeptide of the present invention. Methods for obtaining tissue biopsies and body fluids from organisms are well known in the art. Where the biological sample is to include mRNA, a tissue biopsy is the preferred source.

The method(s) provided above may Preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including proliferative diseases and conditions. Such a method is described in U.S. Pat. Nos. 5,858,659 and 5,856,104. The U.S. patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, *Science* 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, *Nature* 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the stronger binding characteristics of PNA:DNA hybrids. In addition, it is more likely that single base mismatches can be determined with PNA/DNA hybridization because a single mismatch in a PNA/DNA 15-mer lowers the melting point (T.sub.m) by 8°-20° C., vs. 4°-16° C. for the DNA/DNA 15-mer duplex. Also, the absence of charge groups in PNA means that hybridization can be done at low ionic strengths and reduce possible interference by salt during the analysis.

In addition to the foregoing, a polynucleotide can be used to control gene expression through triple helix formation or antisense DNA or RNA. Antisense techniques are discussed, for example, in Okano, *J. Neurochem.* 56: 560 (1991); "Oligodeoxynucleotides as Antisense Inhibitors of Gene Expression, CRC Press, Boca Raton, Fla. (1988). Triple helix formation is discussed in, for instance Lee et al., *Nucleic Acids Research* 6: 3073 (1979); Cooney et al., *Science* 241: 456 (1988); and Dervan et al., *Science* 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., *Nucl. Acids Res.* 6:3073 (1979); Cooney et al., *Science* 241:456 (1988); and Dervan et al., *Science* 251:1360 (1991)) or to the mRNA itself (antisense—Okano, *J. Neurochem.* 56:560 (1991); Oligodeoxynucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

The present invention encompasses the addition of a nuclear localization signal, operably linked to the 5' end, 3' end, or any location therein, to any of the oligonucleotides, antisense oligonucleotides, triple helix oligonucleotides, ribozymes, PNA oligonucleotides, and/or polynucleotides, of the present invention. See, for example, G. Cutrona, et al., *Nat. Biotech.*, 18:300-303, (2000); which is hereby incorporated herein by reference.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell. In one example, polynucleotide sequences of the present invention may be used to construct chimeric RNA/DNA oligonucleotides corresponding to said sequences, specifically designed to induce host cell mismatch repair mechanisms in an organism upon systemic injection, for example (Bartlett, R. J., et al., *Nat. Biotech*, 18:615-622 (2000), which is hereby incorporated by reference herein in its entirety). Such RNA/DNA oligonucleotides could be designed to correct genetic defects in certain host strains, and/or to introduce desired phenotypes in the host (e.g., introduction of a specific polymorphism within an endogenous gene corresponding to a polynucleotide of the present invention that may ameliorate and/or prevent a disease symptom and/or disorder, etc.). Alternatively, the polynucleotide sequence of the present invention may be used to construct duplex oligonucleotides corresponding to said sequence, specifically designed to correct genetic defects in certain host strains, and/or to introduce desired phenotypes into the host (e.g., introduction of a specific polymorphism within an endogenous gene corresponding to a polynucleotide of the present invention that may ameliorate and/or prevent a disease symptom and/or disorder, etc). Such methods of using duplex oligonucleotides are known in the art and are encompassed by the present invention (see EP1007712, which is hereby incorporated by reference herein in its entirety).

The polynucleotides are also useful for identifying organisms from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an organisms genome. These sequences can be used to prepare PCR primers for amplifying and isolating such selected DNA, which can then be sequenced. Using this technique, organisms can be identified because each organism will have a unique set of DNA sequences. Once an unique ID database is established for an organism, positive identification of that organism, living or dead, can be made from extremely small tissue samples. Similarly, polynucleotides of the present invention can be used as polymorphic markers, in addition to, the identification of transformed or non-transformed cells and/or tissues.

There is also a need for reagents capable of identifying the source of a particular tissue. Such need arises, for example, when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination. Moreover, as mentioned above, such reagents can be used to screen and/or identify transformed and non-transformed cells and/or tissues.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods.

(Jalkanen, M., et al., *J. Cell. Biol.* 101:976-985 (1985); Jalkanen, M., et al., *J. Cell. Biol.* 105:3087-3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99 mTc), and fluorescent labels, such as fluorescein and rhodamine, and biotin.

In addition to assaying protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Similarly, antibodies directed to a polypeptide of the present invention can also be used to treat, prevent, and/or diagnose disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Another aspect of the present invention is to gene therapy methods for treating or preventing disorders, diseases and conditions. The gene therapy methods relate to the introduction of nucleic acid (DNA, RNA and antisense DNA or RNA) sequences into an animal to achieve expression of a polypeptide of the present invention. This method requires a polynucleotide which codes for a polypeptide of the invention that operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a polynucleotide of the invention ex vivo, with the engineered cells then being provided to a patient to be treated with the polypeptide. Such methods are well-known in the art. For example, see Belldegrun et al., *J. Natl. Cancer Inst.*, 85:207-216 (1993); Ferrantini et al., *Cancer Research*, 53:107-1112 (1993); Ferrantini et al., *J. Immunology* 153: 4604-4615 (1994); Kaido, T., et al., *Int. J. Cancer* 60: 221-229 (1995); Ogura et al., *Cancer Research* 50: 5102-5106 (1990); Santodonato, et al., *Human Gene Therapy* 7:1-10 (1996); Santodonato, et al., *Gene Therapy* 4:1246-1255 (1997); and Zhang, et al., *Cancer Gene Therapy* 3: 31-38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the polynucleotide constructs can be delivered by any method that delivers injectable materials to the cells of an animal, such as, injection into the interstitial space of tissues (heart, muscle, skin, lung, liver, and the like). The polynucleotide constructs may be delivered in a pharmaceutically acceptable liquid or aqueous carrier.

In one embodiment, the polynucleotide of the invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotides of the invention can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The polynucleotide vector constructs of the invention used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of polynucleotide sequence of the invention. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for the polynucleotides of the invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct of the invention can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the polynucleotide constructs of the invention are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., *Proc. Natl. Acad. Sci.* USA, 84:7413-7416 (1987), which is herein incorporated by reference); mRNA (Malone et al., *Proc. Natl. Acad. Sci.* USA, 86:6077-6081 (1989), which is herein incorporated by reference); and purified transcription factors (Debs et al., *J. Biol. Chem.*, 265:10189-10192 (1990), which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., *Proc. Natl. Acad. Sci.* USA, 84:7413-7416 (1987), which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication NO: WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., Felgner et al., Proc. Natl. Acad. Sci. USA, 84:7413-7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 351 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., *Methods of Immunology*, 101:512-527 (1983), which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., *Biochim. Biophys.* Acta, 394:483 (1975); Wilson et al., *Cell*, 17:77 (1979)); ether injection (Deamer et al., *Biochim. Biophys. Acta*, 443:629 (1976); Ostro et al., *Biochem. Biophys. Res. Commun.*, 76:836 (1977); Fraley et al., *Proc. Natl. Acad. Sci.* USA, 76:3348 (1979)); detergent dialysis (Enoch et al., *Proc. Natl. Acad. Sci.* USA, 76:145 (1979)); and reverse-phase evaporation (REV) (Fraley et al., *J. Biol. Chem.*, 255:10431 (1980); Szoka et al., *Proc. Natl. Acad. Sci.* USA, 75:145 (1978); Schaefer-Ridder et al., *Science*, 215:166 (1982)), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding polypeptides of the invention. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14×, VT-19-17-H2, RCRE, RCRIP, GP+E-86, GP+envAm12, and DAN cell lines as described in Miller, Human Gene Therapy, 1:5-14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding polypeptides of the invention. Such retroviral vector particles then may be employed, to transduce eukaryotic cells, either in vitro or in vivo. The transduced eukaryotic cells will express polypeptides of the invention.

In certain other embodiments, cells are engineered, ex vivo or in vivo, with polynucleotides of the invention contained in an adenovirus vector. Adenovirus can be manipulated such that it encodes and expresses polypeptides of the invention, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz et al., *Am. Rev. Respir. Dis.*, 109:233-238 (1974)). Finally, adenovirus mediated gene transfer has been demonstrated in a number of instances including transfer of alpha-1-antitrypsin and CFTR to the lungs of cotton rats (Rosenfeld et al., *Science*, 252:431-434 (1991); Rosenfeld et al., *Cell*, 68:143-155 (1992)). Furthermore, extensive studies to attempt to establish adenovirus as a causative agent in human cancer were uniformly negative (Green et al. *Proc. Natl. Acad. Sci.* USA, 76:6606 (1979)).

Suitable adenoviral vectors useful in the present invention are described, for example, in Kozarsky and Wilson, *Curr. Opin. Genet. Devel.*, 3:499-503 (1993); Rosenfeld et al., *Cell*, 68:143-155 (1992); Engelhardt et al., *Human Genet. Ther.*, 4:759-769 (1993); Yang et al., *Nature Genet.*, 7:362-369 (1994); Wilson et al., *Nature*, 365:691-692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, *Curr. Topics in Microbiol. Immunol.*, 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354, 678, 5,436,146, 5,474,935, 5,478,745, and 5,589,377.

For example, an appropriate AAV vector for use in the present invention will include all the sequences necessary for DNA replication, encapsidation, and host-cell integration. The polynucleotide construct containing polynucleotides of the invention is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct of the invention. These viral particles are then used to transduce eukaryotic cells, either ex vivo or in vivo. The transduced cells will contain the polynucleotide construct integrated into its genome, and will express the desired gene product.

Another method of gene therapy involves operably associating heterologous control regions and endogenous polynucleotide sequences (e.g. encoding the polypeptide sequence of interest) via homologous recombination (see, e.g., U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932-8935 (1989); and Zijlstra et al., *Nature*, 342:435-438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

The polynucleotides encoding polypeptides of the present invention may be administered along with other polynucleotides encoding angiogenic proteins. Angiogenic proteins include, but are not limited to, acidic and basic fibroblast growth factors, VEGF-1, VEGF-2 (VEGF-C), VEGF-3 (VEGF-B), epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding a polypeptide of the invention contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers. (Kaneda et al., *Science*, 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., *Proc. Natl. Acad. Sci.* USA, 189:11277-11281 (1992), which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian. Therapeutic compositions of the present invention can be administered to any animal, preferably to mammals and birds. Preferred mammals include humans, dogs, cats, mice, rats, rabbits sheep, cattle, horses and pigs, with humans being particularly preferred.

The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

The human MGAT3 polypeptides and/or peptides of the present invention, or immunogenic fragments or oligopeptides thereof, can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the ion channel protein and the agent being tested can be measured. Thus, the present invention provides a method for screening or assessing a plurality of compounds for their specific binding affinity with a MGAT3 polypeptide, or a bindable peptide fragment, of this invention, comprising providing a plurality of compounds, combining the MGAT3 polypeptide, or a bindable peptide fragment, with each of a plurality of compounds for a time sufficient to allow binding under suitable conditions and detecting binding of the MGAT3 polypeptide or peptide to each of the plurality of test compounds, thereby identifying the compounds that specifically bind to the MGAT3 polypeptide or peptide.

Methods of identifying compounds that modulate the activity of the novel human MGAT3 polypeptides and/or peptides are provided by the present invention and comprise combining a potential or candidate compound or drug modulator of MGAT3 biological activity with an MGAT3 polypeptide or peptide, for example, the MGAT3 amino acid sequence as set forth in SEQ ID NO:2, and measuring an effect of the candidate compound or drug modulator on the biological activity of the MGAT3 polypeptide or peptide. Such measurable effects include, for example, physical binding interaction; the ability to cleave a suitable substrate; effects on native and cloned MGAT3-expressing cell line; and effects of modulators or other MGAT3-mediated physiological measures.

Another method of identifying compounds that modulate the biological activity of the novel MGAT3 polypeptides of the present invention comprises combining a potential or candidate compound or drug modulator of MGAT3 biological activity with a host cell that expresses the MGAT3 polypeptide and measuring an effect of the candidate compound or drug modulator on the biological activity of the MGAT3 polypeptide. The host cell can also be capable of being induced to express the MGAT3 polypeptide, e.g., via inducible expression. Physiological effects of a given modulator candidate on the MGAT3 polypeptide can also be measured. Thus, cellular assays for particular MGAT3 modulators may be either direct measurement or quantification of the physical biological activity of the MGAT3 polypeptide, or they may be measurement or quantification of a physiological effect. Such methods preferably employ a MGAT3 polypeptide as described herein, or an overexpressed recombinant MGAT3 polypeptide in suitable host cells containing an expression vector as described herein, wherein the MGAT3 polypeptide is expressed, overexpressed, or undergoes upregulated expression.

Another aspect of the present invention embraces a method of screening for a compound that is capable of modulating the biological activity of a MGAT3 polypeptide, comprising providing a host cell containing an expression vector harboring a nucleic acid sequence encoding a MGAT3 polypeptide, or a functional peptide or portion thereof, determining the biological activity of the expressed MGAT3 polypeptide in the absence of a modulator compound; contacting the cell with the modulator compound and determining the biological activity of the expressed MGAT3 polypeptide in the presence of the modulator compound. In such a method, a difference between the activity of the MGAT3 polypeptide in the presence of the modulator compound and in the absence of the modulator compound indicates a modulating effect of the compound.

Essentially any chemical compound can be employed as a potential modulator or ligand in the assays according to the present invention. Compounds tested as MGAT3 modulators can be any small chemical compound, or biological entity (e.g., protein, sugar, nucleic acid, lipid). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies are particularly envisioned for the detection of modulators of the novel MGAT3 polynucleotides and polypeptides described herein. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, *Int. J. Pept. Prot. Res.*, 37:487-493; and Houghton et al., 1991, *Nature*, 354:84-88). Other chemistries for generating chemical diversity libraries can also be used. Nonlimiting examples of chemical diversity library chemistries include, peptoids (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, *Proc. Natl. Acad. Sci. USA*, 90:6909-6913), vinylogous polypeptides (Hagihara et al., 1992, *J. Amer. Chem. Soc.*, 114:6568), nonpeptidal peptidomimetics with glucose scaffolding (Hirschmann et al., 1992, *J. Amer. Chem. Soc.*, 114:9217-9218), analogous organic synthesis of small compound libraries (Chen et al., 1994, *J. Amer. Chem. Soc.*, 116:2661), oligocarbamates (Cho et al., 1993, *Science*, 261: 1303), and/or peptidyl phosphonates (Campbell et al., 1994, *J. Org. Chem.*, 59:658), nucleic acid libraries (see Ausubel, Berger and Sambrook, all supra), peptide nucleic acid libraries (U.S. Pat. No. 5,539,083), antibody libraries (e.g., Vaughn et al., 1996, *Nature Biotechnology*, 14(3):309-314) and PCT/US96/10287), carbohydrate libraries (e.g., Liang et al., 1996, *Science*, 274-1520-1522) and U.S. Pat. No. 5,593, 853), small organic molecule libraries (e.g., benzodiazepines, Baum *C&EN*, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

In one embodiment, the invention provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000-20,000 different compounds are possible using the described integrated systems.

In another of its aspects, the present invention encompasses screening and small molecule (e.g., drug) detection assays which involve the detection or identification of small molecules that can bind to a given protein, i.e., a MGAT3 polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, Gen. Eng. News, 20(8)). The assay allows the detection of small molecules (e.g., drugs, ligands) that bind to expressed, and preferably purified, ion channel polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify a MGAT3 polypeptide or peptide to measure a biological binding or ligand binding activity, the source may be a whole cell lysate that can be prepared by successive freeze-thaw cycles (e.g., one to three) in the presence of standard protease inhibitors. The MGAT3 polypeptide may be partially or completely purified by standard protein purification methods, e.g., affinity chromatography using specific antibody described infra, or by ligands specific for an epitope tag engineered into the recombinant MGAT3 polypeptide molecule, also as described herein. Binding activity can then be measured as described.

Compounds which are identified according to the methods provided herein, and which modulate or regulate the biological activity or physiology of the MGAT3 polypeptides according to the present invention are a preferred embodiment of this invention. It is contemplated that such modulatory compounds may be employed in treatment and therapeutic methods for treating a condition that is mediated by the novel MGAT3 polypeptides by administering to an individual in need of such treatment a therapeutically effective amount of the compound identified by the methods described herein.

In addition, the present invention provides methods for treating an individual in need of such treatment for a disease, disorder, or condition that is mediated by the MGAT3 polypeptides of the invention, comprising administering to the individual a therapeutically effective amount of the MGAT3-modulating compound identified by a method provided herein.

In specific embodiments, antagonists according to the present invention are nucleic acids corresponding to the sequences contained in SEQ ID NO:1, or the complementary strand thereof, and/or to nucleotide sequences contained in at least one deposited clone. In one embodiment, antisense sequence is generated internally by the organism, in another embodiment, the antisense sequence is separately administered (see, for example, O'Connor, Neurochem., 56:560 (1991). Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, Neurochem., 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research, 6:3073 (1979); Cooney et al., Science, 241:456 (1988); and Dervan et al., Science, 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2× ligation buffer (20 mM TRIS HCl pH 7.5, 10 mM MgCl2, 10 mM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide. Antisense oligonucleotides may be single or double stranded. Double stranded RNA's may be designed based upon the teachings of Paddison et al., Proc. Nat. Acad. Sci., 99:1443-1448 (2002); and International Publication Nos. WO 01/29058, and WO 99/32619; which are hereby incorporated herein by reference.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense nucleic acid of the invention. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding a polypeptide of the invention, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature, 29:304-310 (1981), the promoter contained in the 3' long terminal repeat of Rous sarcoma virus (Yamamoto et al., Cell, 22:787-797 (1980), the herpes thymidine promoter (Wagner et al., Proc. Natl. Acad. Sci. U.S.A., 78:1441-1445 (1981), the regulatory sequences of the metallothionein gene (Brinster et al., Nature, 296:39-42 (1982)), etc.

The antisense nucleic acids of the invention comprise a sequence complementary to at least a portion of an RNA transcript of a gene of interest. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded antisense nucleic acids of the invention, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., *Nature*, 372: 333-335 (1994). Thus, oligonucleotides complementary to either the 5'- or 3'-non-translated, non-coding regions of a polynucleotide sequence of the invention could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., *Proc. Natl. Acad. Sci.* U.S.A. 86:6553-6556 (1989); Lemaitre et al., *Proc. Natl. Acad. Sci.*, 84:648-652 (1987); PCT Publication NO: WO88/09810, published Dec. 15, 1988) or the blood-brain barrier (see, e.g., PCT Publication NO: WO89/10134, published Apr. 25, 1988), hybridization-triggered cleavage agents. (See, e.g., Krol et al., *BioTechniques*, 6:958-976 (1988)) or intercalating agents. (See, e.g., Zon, *Pharm. Res.*, 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., *Nucl. Acids Res.*, 15:6625-6641 (1987)). The oligonucleotide is a 2-O-methylribonucleotide (Inoue et al., *Nucl. Acids Res.*, 15:6131-6148 (1987)), or a chimeric RNA-DNA analogue (Inoue et al., *FEBS Lett.* 215:327-330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (*Nucl. Acids Res.*, 16:3209 (1988)), methylphosphonate oligonucleotides can be prepared by use of controlled pore glass polymer supports (Sarin et al., *Proc. Natl. Acad. Sci.* U.S.A., 85:7448-7451 (1988)), etc.

While antisense nucleotides complementary to the coding region sequence of the invention could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science, 247:1222-1225 (1990). While ribozymes that cleave mRNA at site specific recognition sequences can be used to destroy mRNAs corresponding to the polynucleotides of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature, 334:585-591 (1988). There are numerous potential hammerhead ribozyme cleavage sites within each nucleotide sequence disclosed in the sequence listing. Preferably, the ribozyme is engineered so that the cleavage recognition site is located near the 5' end of the mRNA corresponding to the polynucleotides of the invention; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express the polynucleotides of the invention in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat, prevent, and/or diagnose the diseases described herein.

Thus, the invention provides a method of treating or preventing diseases, disorders, and/or conditions, including but not limited to the diseases, disorders, and/or conditions listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

The following sections sets forth the materials and methods utilized in the present invention.

MATERIALS AND METHODS

A. Identification of Human MGAT3 by Bioinformatics Analysis

A comprehensive BLAST search was conducted using *Saccharomyces Cerevisiae* ScDGAT2 sequence (Accession No. YOR245C; Lardizabal, K. D., et al. (2001) *J. Biol. Chem.*, 276(42):38862-9) against the human genome sequence. The resultant sequences were used to capture the existing EST. The EST information and Genscan program were then used to predict the coding sequence of the candidate genes. These candidates were further filtered using the following criteria: The gene product 1) must be novel; 2) must code for a 30-40 kDa protein; 3) should contain at least one transmembrane region, but does not contain a signal sequence; 4) must have high degree of amino acid sequence conservation with ScDGAT2. The tissue expression patterns for the candidate genes fulfilling all these criteria were profiled using TaqManTM quantitative PCR.

One of the candidate genes which was found to express highly in the intestine, as shown in FIG. 8, designated MGAT3, was chosen for further study. For sequence comparison between MGAT3 and its related proteins, the percentage of sequence identity and similarity was calculated with Gap in GCG program. The multiple sequence alignment was performed with ClustalW algorithm in Vector NTI program.

For mapping of human MGAT3 chromosome localization, the MGAT3 cDNA sequence (SEQ ID NO:1) was mapped to the human genome (NCBI human genome version 29) using Mega-Blast/Sim4 method in the Biotique Local Integration System (BLIS) program.

B. Cloning of Human MGAT3 cDNA

Using the predicted sequences from the bioinformatics analysis, an antisense oligo, designated Oligo A, with biotin on the 5' end was designed with the following sequence: 5'-biotin-GCCCACTGCTTCTAGATGCTGCTTCTG-CAAGGTTTTGGAAGTGGTTGGGGG CTGCAGGGT-TGTGGCAACTCCCATTGCAG-3' (SEQ ID NO:15). To enrich single strand cDNAs that hybridize with this sequence, an aliquot of 0.2 ng of Oligo A was mixed with 6 μg mixture of several single-stranded covalently closed circular cDNA libraries (Life Technologies, Rockville, Md.) in 50% formamide. The mixture was heated to 95° C. for 2 min and hybridized in 50% formamide, 0.75 M NaCl, 0.02 M NaPO4, pH 7.2, 2.5 mM EDTA, 0.1% SDS at 42° C. for 26 hours. The Oligo A/cDNA hybrids were incubated with streptavidin magnetic in high ionic salt buffer containing 10 mM Tris-HCl, pH 7.5, 0.5 M NaCl, 11 mM EDTA, pH 8.0 at 42° C. for 60 min with agitation every 5 min. The beads were separated from the solution with a magnet and were washed three times in 200 μl of 0.1×SSPE, 0.1% SDS at 45° C. The enriched single stranded cDNAs were released from Oligo A/streptavidin magnetic bead complex by incubation with 0.1 N NaOH for 10 min. The released single cDNAs were ethanol precipitated and converted into double strands by PCR with the following pair of oligos:

```
Forward:
5'-GAGCTTCTGCAATGGGAGTT-3'    (SEQ ID NO:16)

Reverse:
5'-TGAGCACATATTGGTAGGCG-3'    (SEQ ID NO:17)
```

The double stranded cDNAs were then transformed into *E. coli* DH12S cells. The transformants with the right predicted size were sequenced. One of the clones, designated human MGAT3, whose sequence fidelity confirmed by the comparison with human genomic sequence and predicted to contain the entire open reading frame, was chosen for further study.

C. TaqMan™ Quantitative PCR Analysis of Human MGAT3

Total RNA was isolated using the TriZol protocol (Invitrogen) and quantified by OD260. For all the experiments described, rRNA 18s and 28s bands were assessed by denaturing gel electrophoresis to ensure the RNA integrity. For real time PCR, primers and probes were obtained from ABI. The human MGAT3 sequence was first aligned with related genes found in GenBank to identity regions of significant sequence divergence. Human MGAT3 primers and probes were then designed using ABI Primer Express Software in order to amplify small amplicons (150 base pairs or less). All primer and probe sequences were also searched against Genbank databases to ensure the target specificity. The oligo sequences are:

```
Forward Primer:
ACTCTGGCCCTTCTCTGTTTTTT        (SEQ ID NO:18)

Reverse Primer:
AACGCCTTCCACCTTGGTT            (SEQ ID NO:19)

Probe:
TCCCAGTCCACATAGAGCCACACCAAG    (SEQ ID NO:20)
```

An aliquot of 100 ng DNase-treated total RNA was annealed to 2.5 µM of Reverse Primer in the presence of 5.5 mM MgCl2 by heating the sample to 72° C. for 2 min and then cooling to 55° C. for 30 min. MuLv reverse transcriptase (1.25 U/µl) and dNTPs (500 µM for each) were added to the reaction at 37° C. for 30 min. The sample was then heated to 90° C. for 5 min to denature the enzyme. Quantitative sequence detection was carried out on a ABI PRISM 7700 by adding to the reverse transcribed reaction mixture with 2.5 µM Forward and Reverse Primers, 2.0 µM of Probe, 500 µM dNTPs, buffer and 5U AmpliTaq Gold™. The PCR reaction was then held at 94° C. for 12 min, followed by 40 cycles of 94° C. for 15 sec and 60° C. for 30 sec. After the run was completed, the threshold cycle (Ct) of the lowest expressing tissue was used as the baseline of expression. Expression level of all other tissues were expressed as the relative abundance to that tissue by calculating the difference in Ct value. The fold of differences between the baseline and the other tissues are calculated as 2ΔCt.

D. Expression of Recombinant Human MGAT3 in Insect Cells

The predicted coding sequence of human MGAT3 was fused with an NH2-terminal FLAG epitope (MGDYKD-DDDG, (SEQ ID NO:21) epitope underlined) and expressed in *Spodoptera frugiperda* (Sf9) insect cells using Bac-to-Bac™ kit (Life Technologies) according to manufacturer's instructions. Recombinant FLAG-human-DGAT2 was expressed in the same manner as a control. Generally, cells were infected with viruses (MOI>3) for 2 days. After harvest, cells were washed with PBS, and then homogenized with a probe sonicator in Homogenization Buffer (10 mM Tris-HCl, pH 7.4, 250 mM sucrose, 1× Protease Inhibitor Cocktail [Roche]). Membrane fractions (100,000×g pellets) were stored at −80° C. until use for enzymatic assays. For immunoblot analysis, aliquots of 2 µg of membrane proteins were loaded on SDS-PAGE and probed with an anti-FLAG M2 IgG (Sigma).

E. MGAT Enzymatic Assays

MGAT activities were assayed for 5-10 min at 37° C. in a final volume of 200 µl according to a protocol modified from Coleman (Coleman, R. A. (1992) *Methods Enzymol*. 209:98-104). Each reaction contained 10 µg of membrane proteins in Assay Buffer (100 mM Tris-HCl, pH7.5, 5 mM MgCl2, 1.25 mg/ml BSA, 250 mM sucrose, 800 µM phophatidylcholine liposomes). Generally, 50 µM of acyl coenzyme A and 200 µM sn-2-monoacylglycerol (delivered in acetone, final acetone concentration <2%) were used. Reactions were started by adding protein and terminated by adding 4 ml chloroform/methanol (2/1, v/v). The extracted lipids were dried, separated by thin layer chromatography (TLC) with hexane/ethyl ether/acetic acid (85/15/0.5, v/v/v). Identities of triacylglycerol (TAG), diacylglycerol (DAG), monoacylglycerol (MAG), free fatty acid (FFA) and other lipids were verified with lipid standards (Sigma) after staining with iodine vapor. The specific enzyme activities were traced by measuring the incorporation of [14C]oleoyl-CoA (20,000 dpm/nmol) or sn-2-[3H] monooleolyglycerol (20,000 dpm/nmol). Chromatograms were also analyzed with STORM PhosphoImager.

EXAMPLE 1

Bioinformatics and cDNA Cloning of MGAT3

Using the Materials and Methods described hereinabove, the cDNA of MGAT3 was found to have the polynucleotide sequence shown in FIG. 1 and set forth in SEQ ID NO:1 and encode a 341 amino acid protein having the sequence shown in FIG. 1 and set forth in SEQ ID NO:2.

Hydrophobicity analysis (FIG. 3) suggests that the predicted MGAT3 protein contains up to 5 potential transmembrane domains but does not contain a classic signal sequence at its NH2 terminus. MGAT3 was found to be homologous to members of the DGAT2 gene family (FIG. 2). Sequence comparison indicates that MGAT3 bears 49% identity, 60% similarity to DGAT2 and 44% identity, 51% similarity to MGAT1 respectively. Hence MGAT3 is a novel member of DGAT2 gene family (for discussion of DGAT2 gene family, see Cases, S., et al. (2001) *J. Biol. Chem.*, 276(42):38870-6).

EXAMPLE 2

Expression of Recombinant Human MGAT3 in Insect Sf9 Cells

Using the Materials and Methods set forth hereinabove, recombinant human MGAT3 was expressed in insect Sf9 cells. To facilitate the detection of the MGAT3 heterologous expressed protein, a copy of FLAG epitope was fused in-frame at the NH2 terminus. Three independent strains of MGAT3 recombinant baculoviruses were established and the preliminary results showed that they all expressed the same protein. One was chosen at random for further study.

Upon infection by recombinant MGAT3 virus, Sf9 cell membrane extracts produced a band of 36 kDa on SDS-PAGE gels as detected by anti-FLAG IgG (Figure 4A, lane 2). The size of the protein is in agreement with the predicted molecular mass of human MGAT3. This band is missing in wild type virus and is different than human DGAT2 (FIG. 4, lanes 1 and 3). Aliquots of membrane extracts were used to conduct MGAT assays using radioactive [14C]oleoyl-CoA as the tracer. The TLC chromatogram shows that upon the addition of exogenous 2-monooleoylglycerol, recombinant MGAT3 membrane produced two bands corresponding to 1,2- and 1,3-diacylglycerols (DAG) (FIG. 4B, lane5). These DAG products were missing when either membranes infected with wild type or DGAT2 viruses were used (FIG. 4B, lanes 4 and 6).

Both exogenously added MGAT3 and DGAT2 membranes produced triacylglycerol (TAG) band (FIG. 4B, lanes 5 and 6). However, wild type virus failed to produce any TAG labeled band (FIG. 4B, lane 4). The possible explanation is that the endogenous insect cell membrane protein contains background level of MGAT activity whose DAG product can be used by recombinant DGAT2 as a substrate to form TAG. To test the possibility that MGAT3 also has DGAT activity, in lanes 7 to 9 (FIG. 4B), exogenous DAG was assayed directly. Indeed, similar to DGAT2, MGAT3 membrane was able to acylate DAG to form TAG directly.

To assess the recombinant MGAT3 activity quantitatively, labeled DAG and TAG bands were cut from TLC sheets and subjected to liquid scintillation counting (FIG. 5B). Concomitant with the appearance of MGAT3 specific band detected with anti-FLAG IgG (FIG. 5A), the specific activities expressed in the Sf9 cell-membranes rise to as high as 22.8 nmol/min/mg for DAG and 9.3 nmol/min/mg for TAG. Throughout the time course, infection of wild type virus only produced background level of activities at 0.5 nmol/min/mg for DAG and 0.2 nmol/min/mg for TAG respectively.

These results establish that MGAT3 cDNA encodes a membrane protein that contains dual MGAT and DGAT activities.

EXAMPLE 3

Characterization of Recombinant Human MGAT3 Enzymatic Features

Using the Materials and Methods hereinabove, enzymatic features of recombinant human MGAT3 were characterized. To optimize MGAT assay conditions for recombinant human MGAT3, substrate concentrations were titrated (FIG. 6). The optimal concentration for oleoyl-CoA is 50 μM (FIG. 6A) and the optimal concentration for 2-monooleoylglycerol is 200 μM. When the concentration of 2-monooleoylglycerol increased further, the TAG synthesis decreased although DAG synthesis kept increasing until its concentration reached 1 mM.

To assess MAG stereoisomer specificity, sn-1-monooleoylglycerol (1-MAG), sn-2-monoleoylglycerol (2-MAG) and sn-3-monopalmitoylglycerol (3-MAG) were assayed (FIG. 7A). The results indicate that MGAT3 prefers 2-MAG as the substrate (compare lane 5 to lanes 2 and 8 in FIG. 7A) to synthesize DAG. Regardless of which type of MAGs were used, the amount of TAG synthesized did not change. It is possible that the background MGAT activity possessed by the endogenous insect cell membrane does not possess stereo specificity for MAG. When the background level of DAG is produced by it is used DGAT activity encoded by MGAT3 to form TAG.

To test this possibility directly, DGAT2 virus was also used to infect Sf9 cells in parallel to compare (FIG. 7A, lanes 3, 6 and 9). Indeed, the recombinant DGAT2 membranes were able to synthesize similar amount of TAG using three different MAG stereoisomers. Furthermore, the amount of TAG synthesized by recombinant DGAT2 was comparable to that by MGAT3.

To assess the substrate optimum for acyl-CoAs, radioactive sn-2-[3H]monooleoylglycerol was used as the tracer and different acyl-CoAs were used. As shown in FIG. 7B, palmitoyl-CoA (C16:0) and oleoyl-CoA (C18:1) are the best substrates for MGAT3.

EXAMPLE 4

Tissue Expression Profile of human MGAT3

Using the Materials and Methods hereinabove, the tissue expression profile of human MGAT3 was analyzed. As shown in FIG. 8, analysis of human MGAT3 by TaqMan™ quantitative PCR reveals that this gene is selectively expressed in the digestive system. The tissue with the highest expression level is the ileum whose transcripts were found approximately 45,000 times greater than that observed in the majority of the tissues outside of the gastrointestinal tract. The tissues with the next highest expression levels make up the remaining portions of the lower GI, i.e., the jejunum, duodenum, colon, caecum and the rectum. Transcripts are notably missing from the stomach and the esophagus and trachea.

The only other non-GI related tissue to show appreciable expression is the liver. These data indicate that MGAT3 is the elusive MGAT gene whose expression accounts for the high level of intestinal MGAT enzyme activity.

The relative steady state expression levels of MGAT3 were compared in RNA isolated from Crohn's ileum verses that of normal controls (FIG. 9). These data demonstrate that the steady state levels of MGAT3 expression are significantly lower in ileum RNA from Crohn's than that isolated from normals (P=0.005).

EXAMPLE 5

Chromosome Location of Human MGAT3

MGAT3 gene is located on human chromosome 7q22.1 (FIG. 10). This region contains the susceptibility loci for both Crohn's disease and ulcerative Colitis (Satsangi, J., et al. (1996) *Nat. Genet.*, 14(2):199-202).

EXAMPLE 6

Methods for Creating N- and C-Terminal Deletion Mutants

As described elsewhere herein, the present invention encompasses the creation of N- and C-terminal deletion mutants, in addition to any combination of N- and C-terminal deletions thereof, corresponding to the MGAT3 polypeptide of the present invention. A number of methods are available to one skilled in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutant of the present invention, exemplary methods are described below.

Representative PCR amplification conditions are provided below, although the skilled artisan would appreciate that other conditions may be required for efficient amplification. A 100 ul PCR reaction mixture may be prepared using 10 ng of the template DNA (cDNA clone of MGAT3), 200 uM 4dNTPs, 1 uM primers, 0.25U Taq DNA polymerase (PE), and standard Taq DNA polymerase buffer. Typical PCR cycling condition are as follows:

20-25 cycles:45 sec, 93 degrees
2 min, 50 degrees
2 min, 72 degrees
1 cycle:10 min, 72 degrees After the final extension step of PCR, 5U Klenow Fragment may be added and incubated for 15 min at 30 degrees. Upon digestion of the fragment with the NotI and SalI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent *E. coli* cells using methods provided herein and/or otherwise known in the art.

The 5' primer sequence for amplifying any additional N-terminal deletion mutants may be determined by reference to the following formula:

(S+(X*3)) to ((S+(X*3))+25), wherein 'S' is equal to the nucleotide position of the initiating start codon of the MGAT3 gene (SEQ ID NO:1), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:1. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula:

(S+(X*3)) to ((S+(X*3))−25), wherein 'S' is equal to the nucleotide position of the initiating start codon of the MGAT3 gene (SEQ ID NO:1), and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO:1. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

While the invention has been described in connection with specific embodiments therefore, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims. All references cited herein are expressly incorporated in their entirety.

What is claimed is:

1. An isolated nucleic acid molecule comprising the polynucleotide of SEQ ID NO:1.

2. A recombinant vector comprising said isolated nucleic acid molecule of claim 1.

3. An isolated recombinant host cell comprising said recombinant vector of claim 2.

4. An isolated recombinant host cell comprising a polypeptide encoded by the isolated nucleic acid of claim 1.

5. A method of making an isolated polypeptide comprising:
    (a) culturing said recombinant host cell of claim 3 under conditions such that said polypeptide is expressed; and
    (b) recovering said polypeptide.

6. The nucleic acid molecule of claim 1 wherein the nucleic acid is included in at least one of ATCC Deposit numbers PTA-4454 or PTA-4803.

* * * * *